(12) United States Patent
Devaux et al.

(10) Patent No.: US 7,384,632 B2
(45) Date of Patent: Jun. 10, 2008

(54) AGONIST ANTI-TRK-C MONOCLONAL ANTIBODIES

(75) Inventors: Brigitte Devaux, Palo Alto, CA (US);
David L. Shelton, Oakland, CA (US);
Jo-Anne Hongo, Redwood City, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 655 days.

(21) Appl. No.: 10/312,316

(22) PCT Filed: Jun. 22, 2001

(86) PCT No.: PCT/US01/20153

§ 371 (c)(1),
(2), (4) Date: Oct. 30, 2003

(87) PCT Pub. No.: WO01/98361

PCT Pub. Date: Dec. 27, 2001

(65) Prior Publication Data

US 2004/0137513 A1    Jul. 15, 2004

Related U.S. Application Data

(60) Provisional application No. 60/238,319, filed on Oct. 5, 2000, provisional application No. 60/213,141, filed on Jun. 22, 2000.

(51) Int. Cl.
*A61K 39/00* (2006.01)
*A61K 39/395* (2006.01)
*C12P 21/08* (2006.01)

(52) U.S. Cl. ............... 424/142.1; 424/130.1; 424/141.1; 435/70.21

(58) Field of Classification Search ........................ None
See application file for complete search history.

(56) References Cited

U.S. PATENT DOCUMENTS

| | | | | |
|---|---|---|---|---|
| 5,364,769 | A | 11/1994 | Rosenthal | 435/69.1 |
| 5,766,863 | A | 6/1998 | Godowski et al. | 435/7.21 |
| 5,891,650 | A | 4/1999 | Godowski et al. | 435/7.21 |
| 6,015,552 | A | 1/2000 | Watanabe et al. | 424/85.1 |
| 6,656,465 | B2 | 12/2003 | Clary et al. | 424/130.1 |
| 2007/0036794 | A1* | 2/2007 | Devaux et al. | 424/146.1 |

FOREIGN PATENT DOCUMENTS

| | | |
|---|---|---|
| EP | 455460 | 11/1991 |
| EP | 522530 | 1/1993 |
| WO | WO 97 21732 A | 6/1997 |
| WO | WO 98 49308 A | 11/1998 |
| WO | WO 00/24415 | 5/2000 |

OTHER PUBLICATIONS

Rudikoff et al. Proc. Natl. Acad. Sci. USA 1982 vol. 79: p. 1979.*
Berkower. Curr. Opi. Biotech. 1996.7:622-628.*
Wu et al. J. Mol. Biol. (1999) 294, 151-162.*
MacCallum et al. J. Mol. Biol. 1996. 262, 732-745.*
Burgess et al. J of Cell Bio. 111:2129-2138, 1990.*
Bowie et al. Science, 1990, 247:1306-1310.*
Pawson et al. 2003, Science 300:445-452.*
Peterson et al. DNA and Cell Biol. 1998. 17: 1031-1040.*
Barbacid, *J. Neurobiol.* 25:1386-1403 [1994].
Barbarcid, *Ann. New York Acad. Sci.* 766:442-458 [1995].
Barde, Y.A. et al., *EMBO J. 1*, 549-553 [1982].
Barker, PA, *Cell Death Diff.* 5:346-356 [1998].
Belliveau et al., *J. Cell. Biol.* 136:375-388 [1997].
Berkemeir, et al., *Somat. Cell Mol. Genet.* 18(3):233-245 [1992].
Berkmeier, L.R. et al., *Neuron 7*, 857-866 [1991].
Capon et al., *Nature* 337: 525-531 [1989].
Casaccia-Bonnefil, et al., *Cell Death Diff.* 5:357-364 [1998].
Carter et al., *Bio/Technology* 10: 163-167 [1992].
Chaudhry, et al., *Muscle and Nerve* 23:189-192 [2000].
Davies et al. (*Neuron 11*, 565-574 [1993].
Davies, AM, *Curr. Biol. 10*:R198-R200 [2000].
Donovan et al., *A.J. Path.* 147:309-324 [1995].
Donovan et al., *Nature Genetics* 14:210-213 [1996].
Ernfors et al., *Proc. Natl. Acad. Sci. USA* 87, 5454-5458 (1990).
Farinas et al., *Neuron* 21:325-334 [1998].
Gao et al., *Ann. Neurol.* 38(1):30-7 [1995].
Gotz et al., *Nature* 372:266-269 [1994].
Haase et al., *J. Neurol. Sci. 160*:S97-S105 [1998].
Hallbook, F. et al., *Neuron 6*, 845-858 [1991].
Hapner, et al., *Developm. Biol.* 201:90-100 [1998].
Helgren et al., *J. Neurosci.* 17(1):372-82 [1997].
Henzel et al., *J. Chromatography* 404: 41-52 [1987].
Herrmann et al., *Mol. Biol. Cell 4*, 1205-1216 [1993].
Höhn et al., *Nature* 344, 339 [1990].
Hongo et al., *Hybridoma* 14: 253-260 [1995].
Ip et al., *Proc. Natl. Acad. Sci USA* 89, 3060-3064 [1992].
Jones and Reichardt, *Proc. Natl. Acad. Sci. USA 87*, 8060-8064 (1990).
Kabat and Wu, *J. Immunol.* 147: 1709-1719 [1991].
Kaisho et al., *FEBS Lett.* 266, 187 [1990].
Klein et al., *EMBO J. 8*, 3701-3709 [1989].
Kraemer et al., *Arteriol. Thromb. and Vasc. Biol.* 19:1041-1050 [1999].
Lai, et al., *Mol. Cell. Neurosci.* 11(1-2):64-76 [1998].

(Continued)

*Primary Examiner*—Christine J. Saoud
*Assistant Examiner*—Chang-Yu Wang
(74) *Attorney, Agent, or Firm*—Atulya Agarwal; James A. Fox; Heller Ehrman LLP

(57) ABSTRACT

The invention concerns agonist anti-trkC monoclonal antoibodies which mimic certain biological activities of NT-3, the native ligand of trkC. The invention further concerns the use of such antibodies in the prevention and/or treatment of cellular degeneration, including nerve cell damage associated with acute nervous cell system injury and chronic neurodegenerative diseases, including peripheral neuropathy.

2 Claims, 34 Drawing Sheets

OTHER PUBLICATIONS

Lamballe et al., *Cell 66*, 967-979 [1991].
Leibrock, J. et al. *Nature 341*, 149-152 [1989].
Levi-Montalcini, R. et al, P.U., *Physiol. Rev. 48*, 534-569 [1968].
Maisonpierre et al., *Science 247*, 1446 [1990].
Martin-Zanca et al., *Mol. Cell. Biol. 9*(1):24-33 [1989].
Matsudaira, *J. Biol. Chem.* 262: 10035-10038 [1987].
Meakin and Shooter, *Trends Neurosci. 15*, 323-331 [1992].
Middlemas et al., *Mol. Cell. Biol. 11*, 143-153 [1991].
Nilsson et al., *FEBS Letters 424*(3):285-90 [1998].
Raoul et al., *Curr. Op. Neurobiol. 10*:111-117 [2000].
Rodriguez-Tebar et al., *EMBO J. 11*, 917-922 [1992].
Rosenthal et al., *Neuron 4*, 767 [1990].
Ryden and Ibanez, *J. Biol. Chem. 271*:5623-5627 [1996].
Sadick et al., *Exp. Cell Res.* 234: 354-361 [1997].
Shelton et al., *J. Neurosci.* 15: 477-491 [1995].
Thoenen, H. et al., *Rev. Physiol. Biochem. Pharmacol. 109*, 145-178 [1987].
Tsoulfas et al., *Nueron* 10:975-990 [1993].
Ultsch et al., *J. Mol. Biol. 290*:149-159 (1999).
Urfer et al., *Biochem.* 36:4775-4781 [1997].
Urfer et al., *EMBO J.* 14:2795-2805 [1995].
R. Urfer et al., "*High resolution mapping of the binding site of TrkA for nerve growth factor and TrkC for neurotrophin-3 on the second immunologlobulin-like domain onf the Trk receptor*" The Journal of Biological Chemistry, vol. 273, No. 10. Mar. 6, 1998.
M. Mendez et al. "Functional transplant of megabase human immunoglobulin loci recapitulates human antibody response in mice." Nature Genetics, vol. 15, No. 2. Feb. 1997.
J. Hongo et al. "Agonist monoclonal antibodies to human trkC receptor map to epitopes overlapping with NT-3 binding site." Society for Neuroscience Abstracts, vol. 27, No. 1, 2001.

* cited by examiner

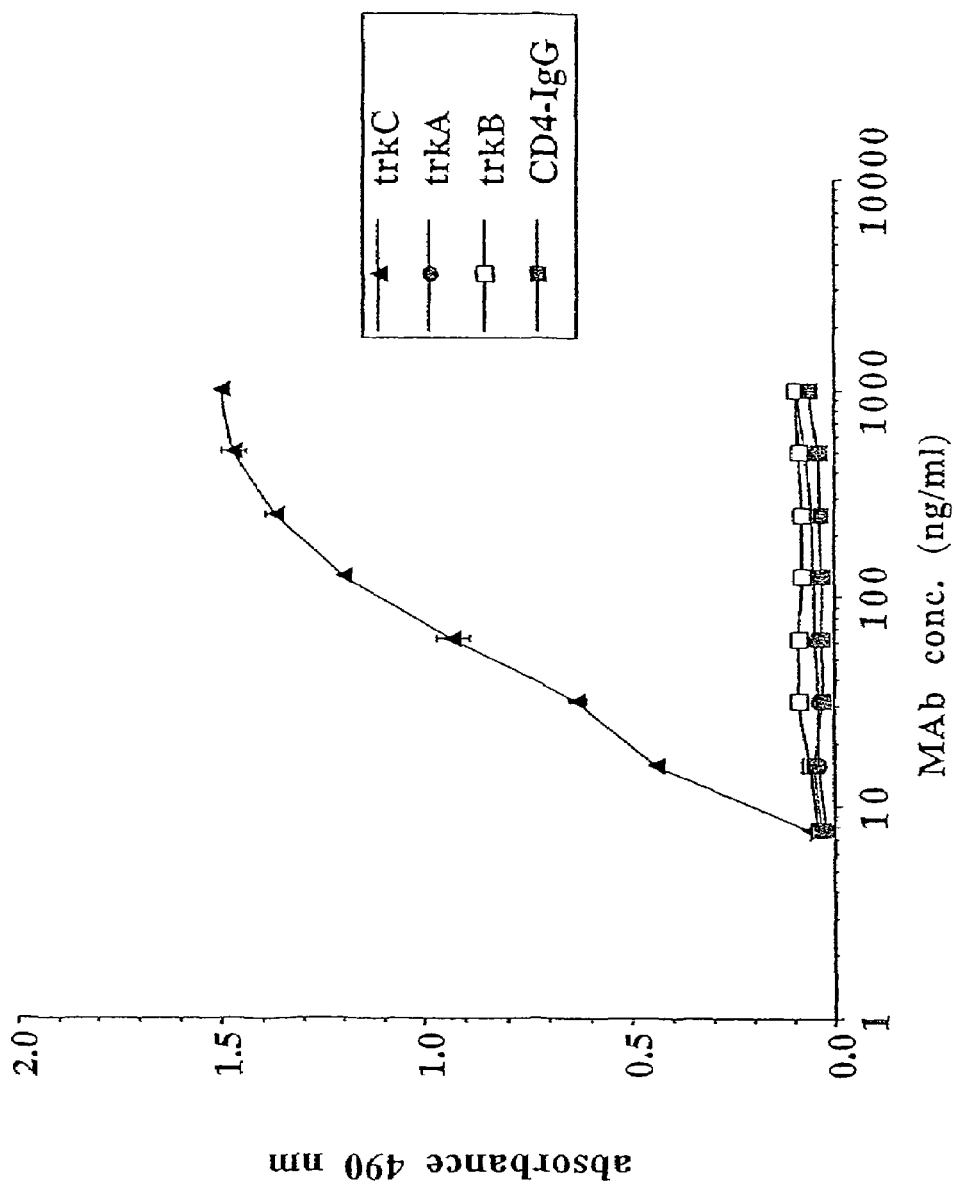

Epitope Mapping Summary

| biotin-MAb | unlabelled MAb | | | | | | | | | |
|---|---|---|---|---|---|---|---|---|---|---|
| | 2344 | 2345 | 2349 | 2.5.1 | 6.1.2 | 6.4.1 | 2248 | 2250 | 2253 | 2256 |
| 2344 | 0.02 | 0 | 0 | 0.01 | 0 | 0 | 1.52 | 0 | 0 | 0 |
| 2345 | 0.26 | 0.04 | 0.02 | 0.17 | 0.11 | 0.08 | 1.48 | 0.04 | 0.07 | 0.05 |
| 2349 | 0.09 | 0.01 | 0 | 0.06 | 0.04 | 0.03 | 1.55 | 0.02 | 0.03 | 0.02 |
| 2.5.1 | 0.06 | 0.01 | 0.01 | 0.03 | 0.03 | 0.02 | 1.54 | 0.01 | 0.02 | 0.01 |
| 6.1.2 | 0.3 | 0.24 | 0.24 | 0.27 | 0.08 | 0.12 | 1.55 | 0.2 | 0.05 | 0.23 |
| 6.4.1 | 0.2 | 0.12 | 0.1 | 0.15 | 0.06 | 0.07 | 1.56 | 0.1 | 0.03 | 0.1 |
| 2248 | 1.52 | 1.53 | 1.54 | 1.5 | 0.74 | 1.12 | 0.01 | 1.4 | 0.04 | 1.48 |
| 2250 | 0.27 | 0.1 | 0.05 | 0.21 | 0.08 | 0.07 | 1.57 | 0.01 | 0.07 | 0.21 |
| 2253 | 1.35 | 1.4 | 1.45 | 1.4 | 0.66 | 0.9 | 1.55 | 1.24 | 0 | 1.34 |
| 2256 | 0.52 | 0.15 | 0.07 | 0.38 | 0.13 | 0.12 | 1.63 | 0.01 | 0.02 | 0.02 |

| Group 1a | Group 2 | Group 3 |
|---|---|---|
| 2344 | 2248 | 2253 |
| 2345 | | |
| 2349 | | |
| 2.5.1 | | |
| 6.1.2 | | |
| 6.4.1 | | |
| 2250 | | |
| 2256 | | |

Domain mapping results are supportive of Group 1 & Group 2 division (2248 is only MAb that binds Domains 4/5; others are D5 specific)

Point mutations suggest that R285 is part of epitope of 2250, 2253 and 2256

Assay Format: gd-trkC + unlabelled MAb + biotinylated MAb + SA-HRP
    (1mg/ml)  (50mg/ml)  (1mg/ml)  (1:1k)

FIG. 5

```
                                                 ─── DOMAIN 4 ───
N- LPEISVSHVNLTVREGDNAVITCNGSGSPLPDVDWIVTGLQSINTHQTNLNWYNVH
    |
   178

AINLTLVNVTSEDNGFTLLTCIAENVVGMSNASVALTVYYPPRVVSLEEPELRLEHCIE
                                 |           •   •  •••••  •
─── DOMAIN 5 ───                266
FVVRGNPPPTLHWLHNNGQPLRESKIIHVEYYQEGEISEGCLLFNKPTHYNNGNYTLIAK
    •              •   •   •• •     •    •       ••  ••     •

NPLGTANQTINGHFLKEPFPVDEV -C
    •            ••    ••
                        |
                       381
```

Heavy chain sequences of anti-trkC agonist MAbs

CDR1 / CDR2

```
2250  : N-QVQLQQSGAELMQPGASVKISCKSTGYTFSNFWIEWVKQRPG--HGLEWIGEILPGSDNTNYNEKFKG
2253  : N-QVQLQQSGAELMQPGASVKISCKSTGYTFSNFWIEWVKQRPG--HGLEWIGEILPGSDNTNYNEKFKG
2256  : N-QVQLQQPGAELVKPGASVKLSCKASGYTFTSYWMHWVKQRPG---OGLEWIGEIYPSNGRTNYNEKFKS
6.1.2 : N-QVQLQESGPGLVKPSQTLSLTCTVSGGSISSGGYYWSWIRQHPGKGLEWIGYIYYSG-STNYNPSLKS
6.4.1 : N-QVQLQESGPGLVRPSETLSLTCTVSGG--SISTYYWNWIRQPAGKGLEWIGRIYTSG-STNYNPSLKS
2345  : N-QVQLQESGPGLVKPSQTLSLTCTVSGGSISSGGYYWSWIRQHPEKGLEWIGYIFYSG-RTYYNPSLKS
2349  : N-QVQLQESGPGLVKPSQTLSLTCTVSGGSISSGGYYYWSWIRQHPGKGLEWIGYIYYSG-STYYNPSLKS
```

CDR3

```
2250  : KATFTADTSSNTAYMQLSSLTSEDSAVYYCARKN-----RN-----YYGNYVVWGQGTLVTVSA-C
2253  : KATFTADTSSNTAYMQLSSLTSEDSAVYYCARKN-----RN-----YYGNYVVWGAGTTLTVSS-C
2256  : KATLTVDKSSSTAYMQLSSLTSEDSAVYYCARKY----YYGNSYRSWYFDVWGAGTTLTVSS-C
6.1.2 : RVTISVDTSKNQFSLKLSSVTAADTAVYYCTRDRDYDSTGDYSYYGMDVWGQGTTVTVSS-C
6.4.1 : RVTMSVDTSKNQFSLKLSSVTAADTAVYYCARDGGYSNPFD-------WGQGTLVTVSS-C
2345  : RVTISVDTSKNQFSLKLNSVTAADTAVYYCARER-IAAAGADYYNGLDVWGQGTTVTVSS-C
2349  : RLTISVDTSKNQFSLKLSSVTAADTAVYYCARER-IAAAGTDYYYNGLAVWGQGTTVTVSS-C
```

Fig. 10

Light chain sequences of anti-trkC agonist MAbs

|  | CDR1 | CDR2 |
|---|---|---|
| 2250 : | N-DIVMTQSPASLAVSLGQRATISYRASKSVSTSG---YSYMHWNQQKPGQPPRLLIYLVSNLESGVPARF |  |
| 2253 : | N-QIVLTQSPAIMSASPGEKVTITCSASSSVSY------MYWFQQKPGTSPKLWIYSTSNLASGVPARF |  |
| 2256 : | N-DIVLTQSPASLAVSLGQRATISCRASESVDNYG--ISFMNWFQQKPGQPPKLLIYAASNQGSGVPARF |  |
| 6.1.2: | N-DIQMTQSPSSLSASVGDRVTITCRASQGIRN-----DLGWYQQKPGKAPKRLIYAASSLQSGVPSRF |  |
| 6.4.1: | N-DIQMTQSPDSLAVSLGERATINCKSSQSVSYSSNNKNYLAWYQQKPGQPPKLLIYWASTRESGVPDRI |  |
| 2345 : | N-EIVLTQSPGTLSLSPGERATLSCRASQSVSS-----NYLTWYQQKPGQAPRLLIYGASSRATGIPDRF |  |
| 2349 : | N-GIVLTQSPGTLSLSPGERATFSCRASQSGSS-----TYLAWYQQKPGQAPRLLIYGASSRATGIPDRF |  |

CDR3

| 2250 : | SGSGSGTDFTLNIHPVEEEDAATYYCQHIRE-LIRSARGQSWKKR---C |
| 2253 : | SGSGSGTSYSLTISRMEAEDAATYYCQQRSS-YPLTFGAGTKLELKR-C |
| 2256 : | SGSGSGTDFSLNIHPMEEDDTAMYFCQQSKE-VPRTFGGGTKLEMKR-C |
| 6.1.2: | SGSGSGTEFTLTISSLQPEDFATFYCLQHNS-LPLTFGGGTKVEIKR-C |
| 6.4.1: | SGSGSGTDFTLTISSLQAEDVAVYYCQQHYN-TPLTFGGGTKVEIKR-C |
| 2345 : | SGSGSGTDFTLTISRLEPEDFAVYYCQQYGRSPPITFGQGTRLEIKR-C |
| 2349 : | SGSGSGTDFTLTISRLEPEDFAVYYCQQYGRSPPITFGQGTRLEIKR-C |

Fig. 11

| Antibody | | Heavy chains | | | | Light chains | | |
|---|---|---|---|---|---|---|---|---|
| | Family | CDR1 | CDR2 | CDR3 | Family | CDR1 | CDR2 | CDR3 |
| Murine | | | | | | | | |
| 2250 | VHIIA | FWIEWVK | EILPGSDNTNYNEKFKG | KNRN----YYGNYVV | V Kappa I | RASKSVSTSGYSYMH | LVSNLES | QHIRELTRS |
| 2253 | VHIIA | FWIEWVK | EILPGSDNTNYNEKFKG | KNRN----YYGNYVV | V Kappa IV | SASSSVS----YMY | STSNLAS | QQRSSYPLT |
| 2256 | VHIIA | YMMHWVK | EIYPSNGRTNYNEKFKS | KYYYGNSYRSWYFDV | V kappa III | RASESVDNYGISFMN | AASNQGS | QQSKEVPRT |
| Human | | | | | | | | |
| 6.1.2 | VHII | SGGYYWS | YIYYSGSTNYNPSLKS | DRDYDSTGDYYSYYGMDV | V Kappa I | RASQGIRN------DLG | AASSLQS | LQHNS-LPLT |
| 6.4.1 | VHII | ISTYYWN | RIYTSGSTNYNPSLKS | DGGYSNPFD--------- | V Kappa I | KSSQSVSYSSNNKNYLA | WASTRES | QQHYN-TPLT |
| 2345 | VHII | SGGYYWS | YIFYSGRTYYNPSLKS | ER-IAAAGADYYNGLDV | V KappaIII | RASQSVSS------NYLT | GASSRAT | QQYGRSPPIT |
| 2349 | VHII | SGYYWS | YIYYSGSTYYNPSLKS | ER-IAAAGTDYYNGLAV | V KappaIII | RASQSGSS------TYLA | GASSRAT | QQYGRSPPIT |

Figure 12. trkC agonist Mabs have improved half-life and bioavailability in vivo Figure 13. Treatment with trkC Agonists Reverses Cisplatinum-Induced Sensory Neuropathy Figure 14. Pyridoxine neuropathy causes decreases in marker expression Pyridoxine-induced deficit on ladder is attenuated by trkC Mab

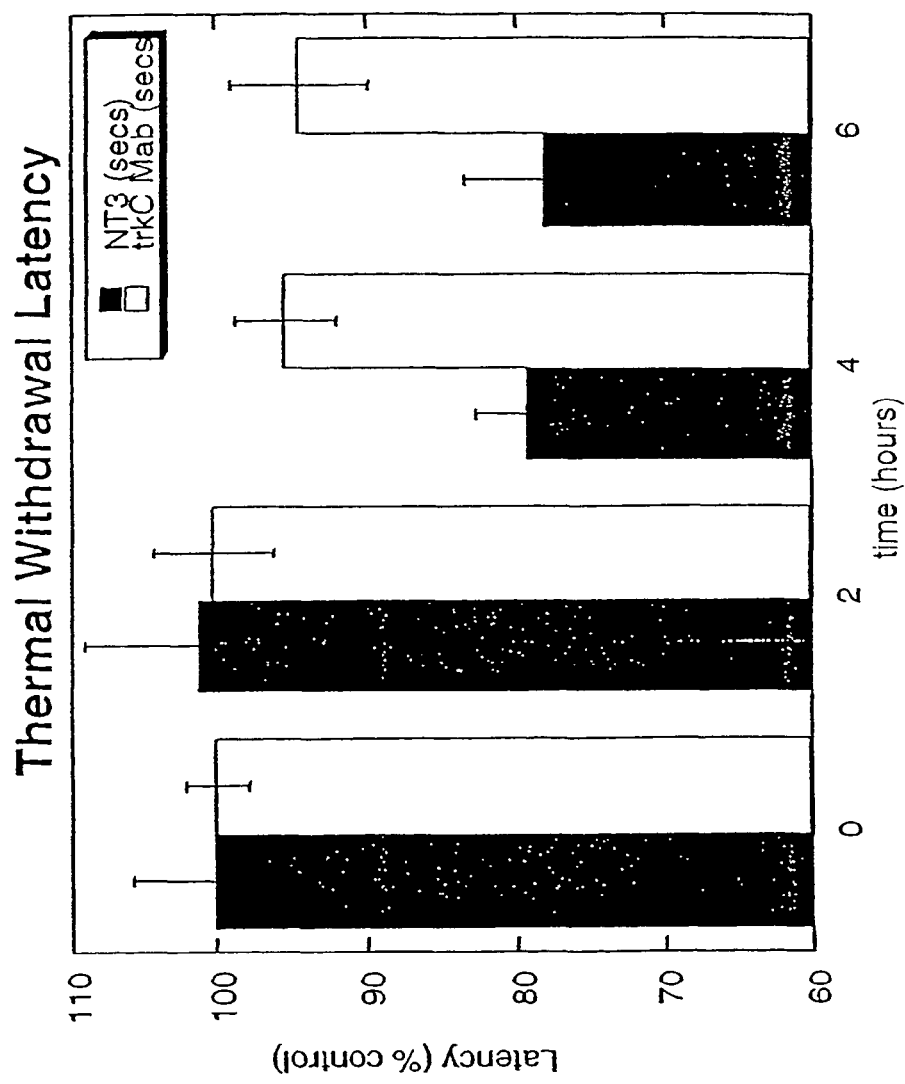
Figure 19. NT3, but not Mab, causes hyperalgesia at therapeutic doses

Fig. 20

```
^ Tue Jun 20 2000 15:48:17
^ /devaux Unix Files/trkcmab/p1.hutrkc
^ , 808 Amino Acids, 0 Stops, MW: 90996.08

1 CPANCVCSKT EINCRRPDDG NLFPLLEGQD SGNSNGNANI NITDISRNIT SIHIENWRSL HTLNAVDMEL YTGLQKLTIK NSGLRSIQPR AFAKNPHLRY
101 INLSSNRLTT LSWQLFQTLS LRELQLEQNF FNCSCDIRWM QLWQEQGEAK LNSQNLYCIN ADGSQLPLFR MNISQCDLPE ISVSHVNLTV REGDNAVITC
                                                                                        ↗Start Domain 4
201 NGSGSPLPDV DWIVTGLQSI NTHQTNLNWT NVHAINLTLV NVTSEDNGFT LTCIAENVVG MSNASVALTV YYPPRVVSLE EPELRLEHCI EFVVRGNPPP
                                                                   ↗Start Domain 5
301 TLHWLHNGQP LRESKIIHVE YYQEGEISEG CLLFNKPTHY NNGNYTLIAK NPLGTANQTI NGHFLKEPFP ESTDNFILFD EVSPTPPITV THKPEEDTFG
                                                                                                    ↗End Domain 5
401 VSIAVGLAAF ACVLLVVLFV MINKYGRRSK FGMKGPVAVI SGEEDSASPL HHINHGITTP SSLDAGPDTV VIGMTRIPVI ENPQYFRQGH NCHKPDTYVQ
501 HIKRRDIVLK RELGEGAFGK VFLAECYNLS PTKDKMLVAV KALKDPTLAA RKDFQREAEL LTNLQHEHIV KFYGVCGDGD PLIMVFEYMK HGDLNKFLRA
601 HGPDAMILVD GQPRQAKGEL GLSQMLHIAS QIASGMVYLA SQHFVHRDLA TRNCLVGANL LVKIGDFGMS RDVYSTDYYR LFNPSGNDFC IWCEVGGHTM
701 LPIRWMPPES IMYRKFTTES DVWSFGVILW EIFTYGKQPW FQLSNTEVIE CITQGRVLER PRVCPKEVYD VMLGCWQREP QQRLNIKEIY KILHALGKAT
801 PIYLDILG
```

Fig. 21

```
> Tue Jun 20 2000 16:10:53
> /devaux Unix Files/trkcmab/ss.hutrkC
> 0 Sites ()
> length: 2607 bp (circular)

1 TGCCCTGCAA ATTGTGTCTG CAGCAAGACT GAGATCAATT GCCGGCGCC  GGACGATGGG AACCTCTTCC CCCTCCTGGA AGGGCAGGAT TCAGGGAACA
     ACGGGACGTT TAACACAGAC GTCGTTCTGA CTCTAGTTAA CGGCCGCCGG CCTGCTACCC TTGGAGAAGG GGGAGGACCT TCCCGTCCTA AGTCCCTGT

101 GCAATGGGAA CGCCAATATC AACATCACGG ACATCACACT TCCATACACA TAGAGAACTG GGCCAGTCTT CACACGGTCA ACGCCGTGA
     CGTTACCCTT GCGGTTATAG TTGTAGTTGCC TGTAGTGTGAA GGTATGTGT ATCTCTTGAC CCGGTCAGAA GTGTGCCAGT TGCGGCACCT

201 CATGGAGCTC TACACCGGAC TTCAAAAGCT GACCATCAAG AACTCAGGAC TTCGGAGCAT TCAGCCCAGA GCCTTTGCCA AGAACCCCCA TTTGCGTTAT
     GTACCTCGAG ATGTGGCCTG AAGTTTTCGA CTGGTAGTTC TTGAGTCCTG AAGCCCGTA AGTCCGGTCT CGGAAACGGT TCTTGGGGT AAACGCAATA

301 ATAAACCTGT CAGTAACCG  GCTCACCACA CTCTCGTGGC AGCTCTTCCA GACGCTGAGT CTTCGGGAAT TGCAGTTGGA GCAGAACTTT TTCAACTGCA
     TATTTGGACA GTTCATTGGC CGAGTGGTGT GAGAGCACCG TCGAGAAGGT CTGCGACTCA GAAGCCCTTA ACGTCAACCT CGTCTTGAAA AAGTTGACGT

401 GCTGTGACAT CCGCTGGATG CAGCTCTGGC AGGAGCAGGG GGAGGCCAAG CTCAACAGCC AGAACTCTA CTGCATCAAT GCTGATGGCT CCCAGCTTCC
     CGACACTGTA GGCGACCTAC GTCGAGACCG TCCTCGTCCC CCTCCGGTTC GAGTTGTCGG TCTTGAGAT GACGTAGTTA CGACTACCGA GGGTCGAAGG

501 TCTCTTCCGC ATGAACATCA GTCAGTGTGA CCTTCCTGAG ATCAGCGTGA GCCACGTGA CCTGACCGTA CGAGAGGGTG ACAATGCTGT TATCACTTGC
     AGAGAAGGCG TACTTGTAGT CAGTCACACT GGAAGGACTC TAGTCGCAGT CGGTGCAGT GGACTGGCAT GCTCTCCCAC TGTTACGACA ATAGTGAACG
                                           ^Start Domain 4

601 AATGGCTCTG GATCACCCTG TCCTGATGTG GACTGGATAG TCACTGGGCT GCAGTCCATC AACACTTACC AGACCAATCT GAACTGGACC AATGTTCATG
     TTACCGAGAC CTAGTGGGAC AGGACTACAC CTGACCTATC AGTGACCCGA CGTCAGGTAG TTGTGAATGG TCTGGTTAGA CTTGACCTGG TTACAAGTAC

701 CCATCAACTT GACGCTGGTG AATGTGACGA GTGAGGACAA TGGCTTCACC CTGACGTGCA TTGCAGAGAA CGTGGTGGGC ATGAGCAATG CCAGTGTTGC
     GGTAGTTGAA CTGCGACCAC TTACACTGCT ACCTCCTGTT ACCGAAGTGG GACTGCACGT AACGTCTCTT GCACCACCCG TACTCGTTAC GGTCACAACG

801 CCTCACTGTC TACTATCCCC CAGTGTGGT GAGCCTGAAG GAGCCTGGAC CTCGGACTCG ACGCCGACCT CGTACGATCAT GCACTGACCTG GAGTTTGTGG TGCTTGGCAA CCCCCCACCA
     GGAGTGACAG ATGATAGGGG GTCACACCAT CTCGGACTTG CTGCCGAGTC TCGGACCTG GAGCCTGAGC CGTGACGTAG TACTAGTTA CACGACCGTT GGGGGGTGGT

901 ACGTGCACT TGGGCAGCCT TGGGCAGCCT CCAAGATCAT CCATGTGGAA TACTACCAAG AGGGAGAGAT TTCCGAGGGC TGCCTGCTCT
     TGCACGTGA CCCAGTCGGA ACCCGTCGGA GGTTCTAGTA GGTACACCTT ATGATGGTTC TCCCTCTCTA AAGGCTCCCG ACGGACGAGA

1001 TCAACAAGCC CACCCACTAC AACAATGGCA ACTATACCCT CATTGCCAAA AACCCACTGG GCACAGCCAA CCAGACCATC AATGGCCACT TCCTCAAGGA
     AGTTGTTCGG GTGGGTGATG TTGTTACCGT TGATATGGGA GTAACGGTTT TTGGGTGACC CGTGTCGGTT GGTCTGGTAG TTACCGGTGA AGGAGTTCCT

1101 GCCCTTTCCA GAGAGCACGG ATAACTTTAT CTTGTTTGAC GAAGTGAGTC CCACACCTCC TATCACTGTG ACCCACAAAC CAGAAGAGA CACTTTTGGG
     CGGGAAAGGT CTCTCGTGCC TATTGAAATA GAACAAACTG CTTCACTCAG GGTGTGGAGG ATAGTGACAC TGGGTGTTTG GTCTTCTCT GTGAAACCC

1201 GTATCCATAG CAGTTGGACT TGCTGCTTT GCCTGTGTCC TGTTGGTGGT TCTCTTCGTC ATGATCAACA AATATGGTCG ACGGTCAAA TTTGGAATGA
     CATAGGTATC GTCAACCTGA ACGACGAAAA CGGACACAGG ACAACCACCA AGAGAAGCAG TACTAGTTGT TTATACCAGC TGCCAGTTT AAACCTTACT
                                                                    ^End Domain 5                          ^Start Domain 5 v1.60 GSeqEdit, ss.hutrkC, page 1
```

Fig. 21 (Pg.2)

```
1301 AGGGTCCCGT GGCTGTCATC AGTGTGAGG AGGACTCAGC CAGCCCACTG CACCACGCAT CACCACGCCC TGTCACTGG ATGCCGGGCC
     TCCCAGGGCA CCGACAGTAG TCACCACTCC TCCTGAGTCG GTCGGGTGAC GTGGTGTAGT TGGTGCCGTA AGCAGTGACC TACGGCCGG

1401 CGACACTGTG GTCATTGGCA TGACTCGGAT CCCTGTCATT GAGAACCCCC AGTACTTCCG TCAGGACAC AACTGCCACA AGCCGGACAC GTATGTGCAG
     GCTGTGACAC CAGTAACCGT ACTGAGCGTA GGGACAGTAA CTCTTGGGGG TCATGAAGGC AGTCCCTGTG TTGACGGTGT TCGGCCTGTG CATACACGTC

1501 CACATTAAGA GGAGAGACAT CGTGCTGAAG CGTGAACTGG GTGAGGAGC CTTTGGAAAG GTCTTCCTGG CCGAGTGCTA CAACCTCAGC CCGACCAAGG
     GTGTAATTCT CCTCTCTGTA GCACGACTTC GCACGACC CACTCCCGTG GAAACCTTTC CAGAAGGACC GGCTCACGAT GTTGGAGTCG GGCTGGTTCC

1601 ACAAGATGCT TGTGGCTGTG AAGGCCCTGA AGGATCCCAC CCTGGCTGCC CGGAAGGATT TCCAGAGGGA GGCCAGCTG CTCACCAACC TCCAGCATGA
     TGTTCTACGA ACACCGACAC TTCCGGGACT TCCTAGGGTG GGACCGACGG GCCTTCCTAA AGGTCTCCCT CCGGCTCGAC GAGTGGTTGG ACGTCGTACT

1701 GCACATTGTC AAGTTCTATG GAGTCTGCGG CGATGGGGAC CCCCTCATCA TGGTCTTTGA ATACATGAAG CATGGAGAAC CCTCAGGGCC
     CGTGTAACAG TTCAAGATAC CTCACACGCC GCTACCCCTG GGGGAGTAGT ACCAGATAGT TACCATTTC GTACCTCTGG ACTTATTCAA GGAGTCCCGG

1801 CATGGGCCAG ATGCAATGAT CCTTGTGGAT GGACAGCCAA GCCAGCCAC GGTGAGCTG GGGCTCTCCC AAATGCTCCA CATTGCCAGT CAGATCGCCT
     GTACCGGGTC TACGTTACTA GGAACACCTA CCTGTCGGTT CGGTCCGGTG CCACTCGAC CCCGAGAGG TTTACGAGGT GTAACGGTCA GTCTAGCGGA

1901 CGGTATGGT GTACCTGGCC TCCCAGCACT TTTGTGCACCG AGACCTGGCC ACCAGGAACT GCCTGGTTGG AGGCAATCTG CTAGTGAAGA TTGGGGACTT
     GCCCATACCA CATGGACCGG AGGGTCGTGA AACACGTGGC TCTGGACCGG TGGTCCTTGA CGGACCAACC TCCCTTAGAC GATCACTTCT AACCCCTGAA

2001 CGGCATGTCC AGAGATGTCT ACAGCACGGA TTATTACAGG CTCTTAATC CATCTGAAA TGATTTTTGT ATATGGTGTG AGGTGGAGG ACACCATG
     GCCGTACAGG TCTCTACAGA TGTCGTGCCT AATAATGTCC GAGAAATTAG GTAGACTTT ACTAAAAACA TATACCACAC TCCACCTCC TGTGTGTAC

2101 CTCCCCATTC GCTGGATGCC TCCTGAAAGC ATCATGTACC GGAAGTTCAC TACGAGAGT GATCTATGA GCTTCGGGGT GATCCTCTGG GAGATCTTCA
     GAGGGGTAAG CGACCTACGG AGGACTTCG TAGTACATGG CCTTCAAGTG ATGTCTCTCA CTACATCCT CGAAGCCCA CTAGGAGACC CTCTAGAAGT

2201 CCTAACCTCT GCAGCCATGG TTCCAACTCT CAAACACGGA GGTCATTGAG TGCATTACCC AAGCTCGTGT TTCCAGCACA CCCCGAGTCT GCCCAAAGA
     GGATACCTTT CGTCGGTACC AAGGTTGAGA GTTTGTGCCT CAGTAACTC ACGTAATGGG TTCCAGACA AAGCTCGCGC GGGGCTCAGA CGGGTTTCT

2301 GGTGTACGAT GTCATGCTGG GGTGCTGGCA GAGGAACCA CAGGAGCGT TGAACATCAA GAGATCTAC TGAAGCATCA ACTTGTAGT AAAATCCTTG GAAGGCCACC
     CCACATGCTA CAGTAGCGACC CCACGACCGT CTCCCCTTGGT GTCGTCGCCA ACTTGTAGT TGAGACAA TATGAGAGG TTTTAGGAGG TAGAAACCC CTTCGGTGG

2401 CCAATCTACC TGGCTGGTGG TCTTCATATA AACTCAAGTG CCTGCTACAC TCATGAATTC ATACTCTGTT GCCTCCTCTC ACATCTCCCT TCCACCTCAC
     GGTTAGATGG ACCTGAAGA ACCGACCACC AGAAGTATAT TTGAGTTCAC GGACGATGTG AGTACTTAAG TATGAGACAA CGGAGGAGAG TGTAGAGGGA AGGTGGAGTG

2501 AACTTCCTTCC ATCCTTGACT GAAGCGAACA TCTTCATATA CCTGCTACAC ATACAAGACT GAAAAAAGGA AAAAAAAAAA
     TTGAGGAAGG TAGGAACTGA CTTCGCTTGT AGAAGTATAT GGACGATGTG TATGTGTGA CTTTTTCCT TTTTTTTTT

2601 AAACCGC
     TTTGGCG length: 2607 v1.60 GSeqEdit, ss.hutrkC, page 2 not found:
```

A. MAb 2250 Heavy chain:

CAGGTCCAACTGCAGCAGTCTGGGGCTGAGCTGATGCAGCCTGGGGCCTCAGTGAAGATA
TCCTGCAAGTCTACTGGCTACACATTCAGTAACTTCTGGATAGAGTGGGTAAAGCAGAGG
CCTGGACATGGCCTTGAGTGGATTGGAGAGATTTTACCTGGCAGTGATAATACTAACTAC
AATGAGAAGTTCAAGGGCAAGGCCACATTCACTGCAGATACATCCTCCAACACAGCCTAC
ATGCAACTCAGCAGCCTGACATCTGAGGACTCTGCCGTCTATTACTGTGCAAGAAAGAAT
CGTAACTACTATGGTAACTACGTTGTATGGGGCCAAGGGACTCTGGTCACTGTCTCTGCA

B. MAb 2250 Light chain:

GACATTGTGATGACCCAGTCTCCTGCTTCCTTAGCTGTATCTCTGGGGCAGAGGGCCACC
ATCTCATACAGGGCCAGCAAAAGTGTCAGTACATCTGGCTATAGTTATATGCACTGGAAC
CAACAGAAACCAGGACAGCCACCCAGACTCCTCATCTATCTTGTATCCAACCTAGAATCT
GGGGTCCCTGCCAGGTTCAGTGGCAGTGGGTCTGGGACAGACTTCACCCTCAACATCCAT
CCTGTGGAGGAGGAGGATGCTGCAACCTATTACTGTCAGCACATTAGGGAGCTTACACGT
TCGGCTCGGGGACAAAGTTGGAAAAAACGG

Fig 22

A. MAb 2253 Heavy chain:

CAGGTCCAGCTGCAGCAGTCTGGAGCTGAGCTGATGCAGCCTGGGGCCTCAGTGAAGATA
TCCTGCAAGTCTACTGGCTACACATTCAGTAACTTCTGGATAGAGTGGGTAAAGCAGAGG
CCTGGACATGGCCTTGAGTGGATTGGAAGATTTTACCTGGCAGTGATAATACTAACTACA
ATGAGAAGTTCAAGGGCAAGGCCACATTCACTGCAGATACATCCTCCAACACAGCCTACA
TGCAACTCAGCAGCCTGACATCTGAGGACTCTGCCGTCTATTACTGTGCAAGAAAGAATC
GTAACTACTATGGTAACTACGTTGTCTGGGGCGCAGGCACCACTCTCACAGTCTCCTCA

B. MAb 2253 Light chain:

CAAATTGTGCTGACCCAGTCTCCAGCAATCATGTCTGCATCTCCAGGGGAGAAGGTCACC
ATAACCTGCAGTGCCAGCTCAAGTGTAAGTTACATGTACTGGTT
CCAGCAGAAGCCAGGCACTTCTCCCAAACTCTGGATTTATAGTACATCCAACCTGGCTTC
TGGAGTCCCTGCTCGCTTCAGTGGCAGTGGATCTGGGACCTCTTACTCTCTCACAATCAG
CCGAATGGAGGCTGAAGATGCTGCCACTTATTACTGCCAGCAAAGGAGTAGTTACCCGCT
CACGTTCGGTGCTGGGACCAAGCTGGAACTAAAACGG

Fig 23

A. MAb 2256 Heavy chain:

CAGGTCCAGCTGCAGCAGCCTGGGGCTGAACTGGTGAAGCCTGGGGCTTCAGTGAAGCTG
TCCTGCAAGGCTTCTGGCTACACCTTCACCAGCTACTGGATGCACTGGGTGAAGCAGAGG
CCTGGACAAGGCCTTGAGTGGATTGGAGAGATTTATCCTAGCAACGGTCGTACTAACTAC
AATGAGAAGTTCAAGAGCAAGGCCACACG
ACTGTAGACAAATCCTCCAGCACAGCCTACATGCAACTCAGCAGCCTGACATCTGAGGAC
TCTGCGGTCTATTACTGTGCAAGAAAATATTACTACGGTAATAGCTATCGTTCCTGGTAC
TTCGATGTCTGGGGCGCAGGCACCACTCTCACAGTCTCCTCA

B. MAb 2256 Light chain:

GACATTGTGCTGACCCAGTCTCCAGCTTCTTTGGCTGTGTCTCTAGGGCAGAGGGCCACC
ATCTCCTGCAGAGCCAGCGAAAGTGTTGATAATTATGGCATTAGTTTTATGAACTGGTTC
CAACAGAAACCAGGACAGCCACCCAAACTCCTCATCTATGCTGCATCCAACCAAGGATCC
GGGGTCCCTGCCAGGTTTAGTGGCAGTGGGTCTGGGACAGACTTCAGCCTCAACATCCAT
CCTATGGAGGAGGATGATACTGCAATGTATTTCTGTCAGCAAAGTAAGGAGGTTCCTCGG
ACGTTCGGTGGAGGCACCAAGCTGGAGATGAAACGG

Fig 24

A. MAb 2345 Heavy chain:

CAGGTGCAGCTGCAGGAGTCGGGCCCAGGACTGGTGAAGCCTTCACAGACCCTGTCCCTC
ACCTGCACTGTCTCTGGTGGCTCCATCAGCAGTGGTGGTTACTACTGGAGCTGGATCCGC
CAGCACCCAGAAAAGGGCCTGGAGTGGTTGGGTACATCTTTTACAGTGGGAGGACCTACT
ACAACCCGTCCCTCAAGAGTCGAGTTACATATCAGTAGACACGTCTAAGAACCAGTTCTC
CCTGAAGCTGAACTCTGTGACaGCCGCGGACACGGCCGTGTATTACTGTGCGAGAGAGCG
GATAGCAGCAGCTGGTGCGGACTACTACTACAACGGTTTGGACGTCTGGGGCCAAGGGAC
CACGGTCACCGTCTCCTCA

B. MAb 2345 Light chain:

GAAATTGTGTTGACGCAGTCTCCAGGCACCCTGTCTTTGTCTCCAGGGGAAAGAGCCACC
CTCTCCTGCAGGGCCAGTCAGAGTGTTAGCAGCAACTACTTAACCTGGTACCAGCAGAAA
CCTGGCCAGGCTCCCAGGCTCCTCATCTATGGTGCATCCAGCAGGGCCACTGGCATCCCA
GACAGGTTCAGTGGCAGTGGGTCTGGGACAGACTTCACTCTCACCATCAGCAGACTGGAG
CCTGAAGATTTTGCAGTGTATTACTGTCAGCAGTATGGTCGCTCACCTCCGATCACCTTC
GGCCAAGGGACACGACTGGAGATTAAACGA

Fig 25

A. MAb 2349 Heavy chain:

CAGGTGCAGCTGCAGGAGTCGGGCCCAGGACTGGTGAAGCCTTCACAGACCCTGTCCCTC
ACCTGCACTGTCTCTGGTGGCTCCATCAGCAGTGGTTATTATTATTGGAGCTGGATCCGC
CAGCACCCAGGGAAGGGCCTGGAGTGGATTGGGTACATCTATTACAGTGGGAGCACCTAC
TACAACCCGTCCCTCAAGAGTCGACTTACTATCAGTAGACACGTCTAAGAACCAGTTCTC
CCTGAAGCTGAGCTCTGTGACTGCCGCGGACACGGCCGTGTATTACTGTGCGAGAGAGCG
GATAGCAGCAGCTGGAACGGACTACTACTACAACGGTTTGGCCGTCTGGGGCCAAGGGAC
CACGGTCACCGTCTCCTCA

B. MAb 2349 Light chain:

GGAATTGTGTTGACGCAGTCTCCAGGCACCCTGTCTTTGTCTCCAGGGGAAAGAGCCACT
TTCTCCTGCAGGGCCAGTCAGAGTGGTAGCAGCACCTACTTAGCTGGTACCAGCAGAAAC
CTGGCCAGGCTCCCAGGCTCCTCATCTATGGTGCATCCAGCAGGGCCACTGGCATCCCAG
ACAGGTTCAGTGGCAGTGGGTCTGGGACAGACTTCACTCTCACCATCAGCAGACTGGAGC
CTGAAGATTTTGCAGTGTATTACTGTCAGCAGTATGGTAGGTCACCTCCGATCACCTTCG
GCCAAGGGACACGACTGGAGATTAAACGA

Fig 26

A. MAb 6.1.2 Heavy chain:

```
CAGGTGCAGCTGCAGGAGTCGGGCCCAGGACTGGTGAAGCCTTCACAGACCCTGTCCCTC
ACCTGCACTGTCTCTGGTGGCTCCATCAGCAGTGGTGGTTACTACTGGAGCTGGATCCGC
CAGCACCCAGGGAAGGGCCTGGAGTGGATTGGGTACATCTATTACAGTGGGAGCACCAAC
TACAACCCGTCCCTCAAGAGTCGAGTTACCATATCAGTGGACACGTCTAAGAACCAGTTC
TCCCTGAAGCTGAGCTCTGTGACTGCCGCGGACACGGCCGTGTATTACTGTACGAGAGAT
CGGGACTATGATAGTACCGGGGATTACTACTCCTACTACGGTATGGACGTCTGGGGCCAA
GGGACCACGGTCACCGTCTCCTCA
```

B. MAb 6.1.2 Light chain:

```
GATATCCAGATGACCCAGTCTCCATCCTCCCTGTCTGCATCTGTAGGAGACAGAGTCACC
ATCACTTGCCGGGCAAGTCAGGGCATTAGAAATGATTTAGGCTGGTATCAGCAGAAACCA
GGGAAAGCCCCTAAGCGCCTGATCTATGCTGCATCCAGTTTGCAAAGTGGGGTCCCATCA
AGGTTCAGCGGCAGTGGATCTGGGACAGAATTCACTCTCACAATCAGCAGCCTGCAGCCT
GAAGATTTTGCAACTTTTTACTGTCTACAGCATAATAGTCTTCCGCTCACTTTCGGCGGA
GGGACCAAGGTGGAGATCAAACGA
```

Fig 27

A. MAb 6.4.1 Heavy chain:

```
CAGGTGCAGCTGCAGGAGTCGGGCCCAGGACTGGTGAGGCCTTCGGAGACCCTGTCCCTC
ACCTGCACTGTCTCTGGTGGCTCCATCAGTACTTACTACTGGAACTGGATCCGGCAGCCC
GCCGGGAAGGGACTGGAGTGGATTGGGCGTATCTATACCAGTGGGAGCACCAACTACAAC
CCCTCCCTCAAGAGTCGAGTCACCATGTCAGTAGACACGTCCAAGAACCAGTTCTCCCTG
AAGCTGAGCTCTGTGACCGCCGCGGACACGGCCGTGTATTACTGTGCGAGAGATGGGGGC
TACAGTAACCCTTTTGACTACTGGGGCCAGGGAACCCTGGTCACCGTCTCCTCA
```

B. MAb 6.4.1 Light chain:

```
GATATCCAGATGACCCAGTCTCCAGACTCCCTGGCTGTGTCTCTGGGCGAGAGGGCCACC
ATCAACTGCAAGTCCAGCCAGAGTGTTTCATACAGCTCCAACAATAAGAACTACTTAGCT
TGGTACCAGCAGAAACCTGGACAGCCTCCTAAGCTG
CTCATTTACTGGGCATCTACCCGGGAATCCGGGGTCCCTGACCGAATCAGTGGCAGCGGG
TCTGGGACAGATTTCACTCTCACCATCAGCAGCCTGCAGGCTGAAGATGTGGCAGTTTAT
TACTGTCAACAACATTATAATACTCCACTCACTTTCGGCGGAGGGACCAAGGTGGAGATC
AAACGA
```

Fig 28

SEQUENCE LISTING

```
<160> NUMBER OF SEQ ID NOS: 89

<210> SEQ ID NO 1
<211> LENGTH: 7
<212> TYPE: PRT
<213> ORGANISM: Murine

<400> SEQUENCE: 1

Phe Trp Ile Glu Trp Val Lys
 1               5

<210> SEQ ID NO 2
<211> LENGTH: 7
<212> TYPE: PRT
<213> ORGANISM: Murine

<400> SEQUENCE: 2

Tyr Trp Met His Trp Val Lys
 1               5

<210> SEQ ID NO 3
<211> LENGTH: 7
<212> TYPE: PRT
<213> ORGANISM: Homo sapiens

<400> SEQUENCE: 3

Ser Gly Gly Tyr Tyr Trp Ser
 1               5

<210> SEQ ID NO 4
<211> LENGTH: 7
<212> TYPE: PRT
<213> ORGANISM: Homo sapiens

<400> SEQUENCE: 4

Ile Ser Thr Tyr Tyr Trp Asn
 1               5
```

```
<210> SEQ ID NO 5
<211> LENGTH: 7
<212> TYPE: PRT
<213> ORGANISM: Homo sapiens

<400> SEQUENCE: 5

Ser Gly Tyr Tyr Tyr Trp Ser
 1               5

<210> SEQ ID NO 6
<211> LENGTH: 17
<212> TYPE: PRT
<213> ORGANISM: Murine

<400> SEQUENCE: 6

Glu Ile Leu Pro Gly Ser Asp Asn Thr Asn Tyr Asn Glu Lys Phe Lys
 1               5                  10                  15
Gly

<210> SEQ ID NO 7
<211> LENGTH: 17
<212> TYPE: PRT
<213> ORGANISM: Murine

<400> SEQUENCE: 7

Glu Ile Tyr Pro Ser Asn Gly Arg Thr Asn Tyr Asn Glu Lys Phe Lys
 1               5                  10                  15
Ser

<210> SEQ ID NO 8
<211> LENGTH: 16
<212> TYPE: PRT
<213> ORGANISM: Homo sapiens

<400> SEQUENCE: 8

Tyr Ile Tyr Tyr Ser Gly Ser Thr Asn Tyr Asn Pro Ser Leu Lys Ser
 1               5                  10                  15

<210> SEQ ID NO 9
<211> LENGTH: 16
<212> TYPE: PRT
<213> ORGANISM: Homo sapiens

<400> SEQUENCE: 9

Arg Ile Tyr Thr Ser Gly Ser Thr Asn Tyr Asn Pro Ser Leu Lys Ser
 1               5                  10                  15

<210> SEQ ID NO 10
<211> LENGTH: 16
<212> TYPE: PRT
<213> ORGANISM: Homo sapiens

<400> SEQUENCE: 10

Tyr Ile Phe Tyr Ser Gly Arg Thr Tyr Tyr Asn Pro Ser Leu Lys Ser
 1               5                  10                  15

<210> SEQ ID NO 11
<211> LENGTH: 16
<212> TYPE: PRT
<213> ORGANISM: Homo sapiens

<400> SEQUENCE: 11

Tyr Ile Tyr Tyr Ser Gly Ser Thr Tyr Tyr Asn Pro Ser Leu Lys Ser
 1               5                  10                  15
```

```
<210> SEQ ID NO 12
<211> LENGTH: 11
<212> TYPE: PRT
<213> ORGANISM: Murine

<400> SEQUENCE: 12

Lys Asn Arg Asn Tyr Tyr Gly Asn Tyr Val Val
1               5                   10

<210> SEQ ID NO 13
<211> LENGTH: 15
<212> TYPE: PRT
<213> ORGANISM: Murine

<400> SEQUENCE: 13

Lys Tyr Tyr Tyr Gly Asn Ser Tyr Arg Ser Trp Tyr Phe Asp Val
1               5                   10                  15

<210> SEQ ID NO 14
<211> LENGTH: 18
<212> TYPE: PRT
<213> ORGANISM: Homo sapiens

<400> SEQUENCE: 14

Asp Arg Asp Tyr Asp Ser Thr Gly Asp Tyr Tyr Ser Tyr Tyr Gly Met
1               5                   10                  15

Asp Val

<210> SEQ ID NO 15
<211> LENGTH: 9
<212> TYPE: PRT
<213> ORGANISM: Homo sapiens

<400> SEQUENCE: 15

Asp Gly Gly Tyr Ser Asn Pro Phe Asp
1               5

<210> SEQ ID NO 16
<211> LENGTH: 17
<212> TYPE: PRT
<213> ORGANISM: Homo sapiens

<400> SEQUENCE: 16

Glu Arg Ile Ala Ala Ala Gly Ala Asp Tyr Tyr Tyr Asn Gly Leu Asp
1               5                   10                  15

Val

<210> SEQ ID NO 17
<211> LENGTH: 17
<212> TYPE: PRT
<213> ORGANISM: Homo sapiens

<400> SEQUENCE: 17

Glu Arg Ile Ala Ala Ala Gly Thr Asp Tyr Tyr Tyr Asn Gly Leu Ala
1               5                   10                  15

Val

<210> SEQ ID NO 18
<211> LENGTH: 15
<212> TYPE: PRT
<213> ORGANISM: Murine

<400> SEQUENCE: 18
```

Arg Ala Ser Lys Ser Val Ser Thr Ser Gly Tyr Ser Tyr Met His
1               5                   10                  15

<210> SEQ ID NO 19
<211> LENGTH: 10
<212> TYPE: PRT
<213> ORGANISM: Murine

<400> SEQUENCE: 19

Ser Ala Ser Ser Ser Val Ser Tyr Met Tyr
1               5                   10

<210> SEQ ID NO 20
<211> LENGTH: 15
<212> TYPE: PRT
<213> ORGANISM: Murine

<400> SEQUENCE: 20

Arg Ala Ser Glu Ser Val Asp Asn Tyr Gly Ile Ser Phe Met Asn
1               5                   10                  15

<210> SEQ ID NO 21
<211> LENGTH: 11
<212> TYPE: PRT
<213> ORGANISM: Homo sapiens

<400> SEQUENCE: 21

Arg Ala Ser Gln Gly Ile Arg Asn Asp Leu Gly
1               5                   10

<210> SEQ ID NO 22
<211> LENGTH: 17
<212> TYPE: PRT
<213> ORGANISM: Homo sapiens

<400> SEQUENCE: 22

Lys Ser Ser Gln Ser Val Ser Tyr Ser Ser Asn Asn Lys Asn Tyr Leu
1               5                   10                  15

Ala

<210> SEQ ID NO 23
<211> LENGTH: 12
<212> TYPE: PRT
<213> ORGANISM: Homo sapiens

<400> SEQUENCE: 23

Arg Ala Ser Gln Ser Val Ser Ser Asn Tyr Leu Thr
1               5                   10

<210> SEQ ID NO 24
<211> LENGTH: 12
<212> TYPE: PRT
<213> ORGANISM: Homo sapiens

<400> SEQUENCE: 24

Arg Ala Ser Gln Ser Gly Ser Ser Thr Tyr Leu Ala
1               5                   10

<210> SEQ ID NO 25
<211> LENGTH: 7
<212> TYPE: PRT
<213> ORGANISM: Murine

<400> SEQUENCE: 25

```
Leu Val Ser Asn Leu Glu Ser
1               5

<210> SEQ ID NO 26
<211> LENGTH: 7
<212> TYPE: PRT
<213> ORGANISM: Murine

<400> SEQUENCE: 26

Ser Thr Ser Asn Leu Ala Ser
1               5

<210> SEQ ID NO 27
<211> LENGTH: 7
<212> TYPE: PRT
<213> ORGANISM: Murine

<400> SEQUENCE: 27

Ala Ala Ser Asn Gln Gly Ser
1               5

<210> SEQ ID NO 28
<211> LENGTH: 7
<212> TYPE: PRT
<213> ORGANISM: Homo sapiens

<400> SEQUENCE: 28

Ala Ala Ser Ser Leu Gln Ser
1               5

<210> SEQ ID NO 29
<211> LENGTH: 7
<212> TYPE: PRT
<213> ORGANISM: Homo sapiens

<400> SEQUENCE: 29

Trp Ala Ser Thr Arg Glu Ser
1               5

<210> SEQ ID NO 30
<211> LENGTH: 7
<212> TYPE: PRT
<213> ORGANISM: Homo sapiens

<400> SEQUENCE: 30

Gly Ala Ser Ser Arg Ala Thr
1               5

<210> SEQ ID NO 31
<211> LENGTH: 9
<212> TYPE: PRT
<213> ORGANISM: Murine

<400> SEQUENCE: 31

Gln His Ile Arg Glu Leu Thr Arg Ser
1               5

<210> SEQ ID NO 32
<211> LENGTH: 9
<212> TYPE: PRT
<213> ORGANISM: Murine

<400> SEQUENCE: 32

Gln Gln Arg Ser Ser Tyr Pro Leu Thr
1               5
```

```
<210> SEQ ID NO 33
<211> LENGTH: 9
<212> TYPE: PRT
<213> ORGANISM: Murine

<400> SEQUENCE: 33

Gln Gln Ser Lys Glu Val Pro Arg Thr
  1               5

<210> SEQ ID NO 34
<211> LENGTH: 9
<212> TYPE: PRT
<213> ORGANISM: Homo sapiens

<400> SEQUENCE: 34

Leu Gln His Asn Ser Leu Pro Leu Thr
  1               5

<210> SEQ ID NO 35
<211> LENGTH: 9
<212> TYPE: PRT
<213> ORGANISM: Homo sapiens

<400> SEQUENCE: 35

Gln Gln His Tyr Asn Thr Pro Leu Thr
  1               5

<210> SEQ ID NO 36
<211> LENGTH: 10
<212> TYPE: PRT
<213> ORGANISM: Homo sapiens

<400> SEQUENCE: 36

Gln Gln Tyr Gly Arg Ser Pro Pro Ile Thr
  1               5                  10

<210> SEQ ID NO 37
<211> LENGTH: 7
<212> TYPE: PRT
<213> ORGANISM: Murine
<220> FEATURE:
<221> NAME/KEY: UNSURE
<222> LOCATION: 1
<223> OTHER INFORMATION: Xaa = F or Y
<220> FEATURE:
<221> NAME/KEY: UNSURE
<222> LOCATION: 3
<223> OTHER INFORMATION: Xaa = I or M
<220> FEATURE:
<221> NAME/KEY: UNSURE
<222> LOCATION: 4
<223> OTHER INFORMATION: Xaa = E or H

<400> SEQUENCE: 37

Xaa Trp Xaa Xaa Trp Val Lys
  1               5

<210> SEQ ID NO 38
<211> LENGTH: 17
<212> TYPE: PRT
<213> ORGANISM: Murine
<220> FEATURE:
<221> NAME/KEY: UNSURE
<222> LOCATION: 3
<223> OTHER INFORMATION: Xaa = L or Y
<220> FEATURE:
<221> NAME/KEY: UNSURE
```

```
<222> LOCATION: 5
<223> OTHER INFORMATION: Xaa = G or S
<220> FEATURE:
<221> NAME/KEY: UNSURE
<222> LOCATION: 6
<223> OTHER INFORMATION: Xaa = S or N
<220> FEATURE:
<221> NAME/KEY: UNSURE
<222> LOCATION: 7
<223> OTHER INFORMATION: Xaa = D or G
<220> FEATURE:
<221> NAME/KEY: UNSURE
<222> LOCATION: 8
<223> OTHER INFORMATION: Xaa = N or R
<220> FEATURE:
<221> NAME/KEY: UNSURE
<222> LOCATION: 17
<223> OTHER INFORMATION: Xaa = G or S

<400> SEQUENCE: 38

Glu Ile Xaa Pro Xaa Xaa Xaa Xaa Thr Asn Tyr Asn Glu Lys Phe Lys
 1               5                  10                  15

Xaa

<210> SEQ ID NO 39
<211> LENGTH: 7
<212> TYPE: PRT
<213> ORGANISM: Homo sapiens
<220> FEATURE:
<221> NAME/KEY: UNSURE
<222> LOCATION: 1
<223> OTHER INFORMATION: Xaa = S or I
<220> FEATURE:
<221> NAME/KEY: UNSURE
<222> LOCATION: 2
<223> OTHER INFORMATION: Xaa = G or S
<220> FEATURE:
<221> NAME/KEY: UNSURE
<222> LOCATION: 3
<223> OTHER INFORMATION: Xaa = G, T or Y
<220> FEATURE:
<221> NAME/KEY: UNSURE
<222> LOCATION: 7
<223> OTHER INFORMATION: Xaa = S or N

<400> SEQUENCE: 39

Xaa Xaa Xaa Tyr Tyr Trp Xaa
 1               5

<210> SEQ ID NO 40
<211> LENGTH: 16
<212> TYPE: PRT
<213> ORGANISM: Homo sapiens
<220> FEATURE:
<221> NAME/KEY: UNSURE
<222> LOCATION: 1
<223> OTHER INFORMATION: Xaa = Y or R
<220> FEATURE:
<221> NAME/KEY: UNSURE
<222> LOCATION: 3
<223> OTHER INFORMATION: Xaa = Y or F
<220> FEATURE:
<221> NAME/KEY: UNSURE
<222> LOCATION: 4
<223> OTHER INFORMATION: Xaa = Y or T
<220> FEATURE:
<221> NAME/KEY: UNSURE
<222> LOCATION: 8
<223> OTHER INFORMATION: Xaa = S or R
<220> FEATURE:
<221> NAME/KEY: UNSURE
<222> LOCATION: 10
<223> OTHER INFORMATION: Xaa = N or Y
```

-continued

```
<400> SEQUENCE: 40

Xaa Ile Xaa Xaa Ser Gly Ser Xaa Thr Xaa Asn Pro Ser Leu Lys Ser
 1               5                  10                  15

<210> SEQ ID NO 41
<211> LENGTH: 17
<212> TYPE: PRT
<213> ORGANISM: Homo sapiens
<220> FEATURE:
<221> NAME/KEY: UNSURE
<222> LOCATION: 8
<223> OTHER INFORMATION: Xaa = A or T
<220> FEATURE:
<221> NAME/KEY: UNSURE
<222> LOCATION: 16
<223> OTHER INFORMATION: Xaa = D or A

<400> SEQUENCE: 41

Glu Arg Ile Ala Ala Ala Gly Xaa Asp Tyr Tyr Tyr Asn Gly Leu Xaa
 1               5                  10                  15

Val

<210> SEQ ID NO 42
<211> LENGTH: 122
<212> TYPE: PRT
<213> ORGANISM: Murine

<400> SEQUENCE: 42

Asn Gln Val Gln Leu Gln Gln Ser Gly Ala Glu Leu Met Gln Pro Gly
 1               5                  10                  15

Ala Ser Val Lys Ile Ser Cys Lys Ser Thr Gly Tyr Thr Phe Ser Asn
                20                  25                  30

Phe Trp Ile Glu Trp Val Lys Gln Arg Pro Gly His Gly Leu Glu Trp
            35                  40                  45

Ile Gly Glu Ile Leu Pro Gly Ser Asp Asn Thr Asn Tyr Asn Glu Lys
        50                  55                  60

Phe Lys Gly Lys Ala Thr Phe Thr Ala Asp Thr Ser Ser Asn Thr Ala
 65                 70                  75                  80

Tyr Met Gln Leu Ser Ser Leu Thr Ser Glu Asp Ser Ala Val Tyr Tyr
                85                  90                  95

Cys Ala Arg Lys Asn Arg Asn Tyr Tyr Gly Asn Tyr Val Val Trp Gly
            100                 105                 110

Gln Gly Thr Leu Val Thr Val Ser Ala Cys
        115                 120

<210> SEQ ID NO 43
<211> LENGTH: 122
<212> TYPE: PRT
<213> ORGANISM: Murine

<400> SEQUENCE: 43

Asn Gln Val Gln Leu Gln Gln Ser Gly Ala Glu Leu Met Gln Pro Gly
 1               5                  10                  15

Ala Ser Val Lys Ile Ser Cys Lys Ser Thr Gly Tyr Thr Phe Ser Asn
                20                  25                  30

Phe Trp Ile Glu Trp Val Lys Gln Arg Pro Gly His Gly Leu Glu Trp
            35                  40                  45

Ile Gly Glu Ile Leu Pro Gly Ser Asp Asn Thr Asn Tyr Asn Glu Lys
        50                  55                  60

Phe Lys Gly Lys Ala Thr Phe Thr Ala Asp Thr Ser Ser Asn Thr Ala
```

```
                65                  70                  75                  80
Tyr Met Gln Leu Ser Ser Leu Thr Ser Glu Asp Ser Ala Val Tyr Tyr
                    85                  90                  95

Cys Ala Arg Lys Asn Arg Asn Tyr Tyr Gly Asn Tyr Val Val Trp Gly
                100                 105                 110

Ala Gly Thr Thr Leu Thr Val Ser Ser Cys
                115                 120

<210> SEQ ID NO 44
<211> LENGTH: 126
<212> TYPE: PRT
<213> ORGANISM: Murine

<400> SEQUENCE: 44

Asn Gln Val Gln Leu Gln Gln Pro Gly Ala Glu Leu Val Lys Pro Gly
  1               5                  10                  15

Ala Ser Val Lys Leu Ser Cys Lys Ala Ser Gly Tyr Thr Phe Thr Ser
                20                  25                  30

Tyr Trp Met His Trp Val Lys Gln Arg Pro Gly Gln Gly Leu Glu Trp
            35                  40                  45

Ile Gly Glu Ile Tyr Pro Ser Asn Gly Arg Thr Asn Tyr Asn Glu Lys
        50                  55                  60

Phe Lys Ser Lys Ala Thr Leu Thr Val Asp Lys Ser Ser Ser Thr Ala
 65                  70                  75                  80

Tyr Met Gln Leu Ser Ser Leu Thr Ser Glu Asp Ser Ala Val Tyr Tyr
                    85                  90                  95

Cys Ala Arg Lys Tyr Tyr Tyr Gly Asn Ser Tyr Arg Ser Trp Tyr Phe
                100                 105                 110

Asp Val Trp Gly Ala Gly Thr Thr Leu Thr Val Ser Ser Cys
                115                 120                 125

<210> SEQ ID NO 45
<211> LENGTH: 130
<212> TYPE: PRT
<213> ORGANISM: Homo sapiens

<400> SEQUENCE: 45

Asn Gln Val Gln Leu Gln Glu Ser Gly Pro Gly Leu Val Lys Pro Ser
  1               5                  10                  15

Gln Thr Leu Ser Leu Thr Cys Thr Val Ser Gly Gly Ser Ile Ser Ser
                20                  25                  30

Gly Gly Tyr Tyr Trp Ser Trp Ile Arg Gln His Pro Gly Lys Gly Leu
            35                  40                  45

Glu Trp Ile Gly Tyr Ile Tyr Tyr Ser Gly Ser Thr Asn Tyr Asn Pro
        50                  55                  60

Ser Leu Lys Ser Arg Val Thr Ile Ser Val Asp Thr Ser Lys Asn Gln
 65                  70                  75                  80

Phe Ser Leu Lys Leu Ser Ser Val Thr Ala Ala Asp Thr Ala Val Tyr
                    85                  90                  95

Tyr Cys Thr Arg Asp Arg Asp Tyr Asp Ser Thr Gly Asp Tyr Tyr Ser
                100                 105                 110

Tyr Tyr Gly Met Asp Val Trp Gly Gln Gly Thr Thr Val Thr Val Ser
            115                 120                 125

Ser Cys
    130
```

```
<210> SEQ ID NO 46
<211> LENGTH: 119
<212> TYPE: PRT
<213> ORGANISM: Homo sapiens

<400> SEQUENCE: 46

Asn Gln Val Gln Leu Gln Glu Ser Gly Pro Gly Leu Val Arg Pro Ser
1               5                   10                  15

Glu Thr Leu Ser Leu Thr Cys Thr Val Ser Gly Ser Ile Ser Thr
            20                  25                  30

Tyr Tyr Trp Asn Trp Ile Arg Gln Pro Ala Gly Lys Gly Leu Glu Trp
        35                  40                  45

Ile Gly Arg Ile Tyr Thr Ser Gly Ser Thr Asn Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Gly Tyr Ser Asn Pro Phe Asp Trp Gly Gln Gly Thr
            100                 105                 110

Leu Val Thr Val Ser Ser Cys
        115

<210> SEQ ID NO 47
<211> LENGTH: 129
<212> TYPE: PRT
<213> ORGANISM: Homo sapiens

<400> SEQUENCE: 47

Asn Gln Val Gln Leu Gln Glu Ser Gly Pro Gly Leu Val Lys Pro Ser
1               5                   10                  15

Gln Thr Leu Ser Leu Thr Cys Thr Val Ser Gly Gly Ser Ile Ser Ser
            20                  25                  30

Gly Gly Tyr Tyr Trp Ser Trp Ile Arg Gln His Pro Glu Lys Gly Leu
        35                  40                  45

Glu Trp Ile Gly Tyr Ile Phe Tyr Ser Gly Arg Thr Tyr Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Asn Ser Val Thr Ala Ala Asp Thr Ala Val Tyr
                85                  90                  95

Tyr Cys Ala Arg Glu Arg Ile Ala Ala Gly Ala Asp Tyr Tyr Tyr
            100                 105                 110

Asn Gly Leu Asp Val Trp Gly Gln Gly Thr Thr Val Thr Val Ser Ser
        115                 120                 125

Cys

<210> SEQ ID NO 48
<211> LENGTH: 129
<212> TYPE: PRT
<213> ORGANISM: Homo sapiens

<400> SEQUENCE: 48

Asn Gln Val Gln Leu Gln Glu Ser Gly Pro Gly Leu Val Lys Pro Ser
1               5                   10                  15

Gln Thr Leu Ser Leu Thr Cys Thr Val Ser Gly Gly Ser Ile Ser Ser
            20                  25                  30
```

```
Gly Tyr Tyr Tyr Trp Ser Trp Ile Arg Gln His Pro Gly Lys Gly Leu
            35                  40                  45

Glu Trp Ile Gly Tyr Ile Tyr Tyr Ser Gly Ser Thr Tyr Tyr Asn Pro
        50                  55                  60

Ser Leu Lys Ser Arg Leu Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Glu Arg Ile Ala Ala Gly Thr Asp Tyr Tyr Tyr
            100                 105                 110

Asn Gly Leu Ala Val Trp Gly Gln Gly Thr Thr Val Thr Val Ser Ser
            115                 120                 125

Cys

<210> SEQ ID NO 49
<211> LENGTH: 112
<212> TYPE: PRT
<213> ORGANISM: Murine

<400> SEQUENCE: 49

Asn Asp Ile Val Met Thr Gln Ser Pro Ala Ser Leu Ala Val Ser Leu
1               5                   10                  15

Gly Gln Arg Ala Thr Ile Ser Tyr Arg Ala Ser Lys Ser Val Ser Thr
            20                  25                  30

Ser Gly Tyr Ser Tyr Met His Trp Asn Gln Gln Lys Pro Gly Gln Pro
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Asp Ala Ala Thr Tyr Tyr Cys Gln His Ile
                85                  90                  95

Arg Glu Leu Thr Arg Ser Ala Arg Gly Gln Ser Trp Lys Lys Arg Cys
            100                 105                 110

<210> SEQ ID NO 50
<211> LENGTH: 109
<212> TYPE: PRT
<213> ORGANISM: Murine

<400> SEQUENCE: 50

Asn Gln Ile Val Leu Thr Gln Ser Pro Ala Ile Met Ser Ala Ser Pro
1               5                   10                  15

Gly Glu Lys Val Thr Ile Thr Cys Ser Ala Ser Ser Ser Val Ser Tyr
            20                  25                  30

Met Tyr Trp Phe Gln Gln Lys Pro Gly Thr Ser Pro Lys Leu Trp Ile
        35                  40                  45

Tyr Ser Thr Ser Asn Leu Ala Ser Gly Val Pro Ala Arg Phe Ser Gly
    50                  55                  60

Ser Gly Ser Gly Thr Ser Tyr Ser Leu Thr Ile Ser Arg Met Glu Ala
65                  70                  75                  80

Glu Asp Ala Ala Thr Tyr Tyr Cys Gln Gln Arg Ser Ser Tyr Pro Leu
                85                  90                  95

Thr Phe Gly Ala Gly Thr Lys Leu Glu Leu Lys Arg Cys
            100                 105
```

<210> SEQ ID NO 51
<211> LENGTH: 114
<212> TYPE: PRT
<213> ORGANISM: Murine

<400> SEQUENCE: 51

Asn Asp Ile Val Leu Thr Gln Ser Pro Ala Ser Leu Ala Val Ser Leu
1               5                   10                  15

Gly Gln Arg Ala Thr Ile Ser Cys Arg Ala Ser Glu Ser Val Asp Asn
            20                  25                  30

Tyr Gly Ile Ser Phe Met Asn Trp Phe Gln Gln Lys Pro Gly Gln Pro
        35                  40                  45

Pro Lys Leu Leu Ile Tyr Ala Ala Ser Asn Gln Gly Ser Gly Val Pro
    50                  55                  60

Ala Arg Phe Ser Gly Ser Gly Ser Gly Thr Asp Phe Ser Leu Asn Ile
65                  70                  75                  80

His Pro Met Glu Glu Asp Asp Thr Ala Met Tyr Phe Cys Gln Gln Ser
                85                  90                  95

Lys Glu Val Pro Arg Thr Phe Gly Gly Gly Thr Lys Leu Glu Met Lys
            100                 105                 110

Arg Cys

<210> SEQ ID NO 52
<211> LENGTH: 110
<212> TYPE: PRT
<213> ORGANISM: Homo sapiens

<400> SEQUENCE: 52

Asn Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Asp Leu Gly Trp Tyr Gln Gln Lys Pro Gly Lys Ala Pro Lys Arg Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Phe Tyr Cys Leu Gln His Asn Ser Leu Pro
                85                  90                  95

Leu Thr Phe Gly Gly Gly Thr Lys Val Glu Ile Lys Arg Cys
            100                 105                 110

<210> SEQ ID NO 53
<211> LENGTH: 116
<212> TYPE: PRT
<213> ORGANISM: Homo sapiens

<400> SEQUENCE: 53

Asn Asp Ile Gln Met Thr Gln Ser Pro Asp Ser Leu Ala Val Ser Leu
1               5                   10                  15

Gly Glu Arg Ala Thr Ile Asn Cys Lys Ser Ser Gln Ser Val Ser Tyr
            20                  25                  30

Ser Ser Asn Asn Lys Asn Tyr Leu Ala Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

```
Val Pro Asp Arg Ile Ser Gly Ser Gly Ser Gly Thr Asp Phe Thr Leu
 65                  70                  75                  80

Thr Ile Ser Ser Leu Gln Ala Glu Asp Val Ala Val Tyr Tyr Cys Gln
                 85                  90                  95

Gln His Tyr Asn Thr Pro Leu Thr Phe Gly Gly Gly Thr Lys Val Glu
            100                 105                 110

Ile Lys Arg Cys
        115

<210> SEQ ID NO 54
<211> LENGTH: 112
<212> TYPE: PRT
<213> ORGANISM: Homo sapiens

<400> SEQUENCE: 54

Asn Glu Ile Val Leu Thr Gln Ser Pro Gly Thr Leu Ser Leu Ser Pro
 1               5                  10                  15

Gly Glu Arg Ala Thr Leu Ser Cys Arg Ala Ser Gln Ser Val Ser Ser
            20                  25                  30

Asn Tyr Leu Thr Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Tyr Gly Arg Ser
                 85                  90                  95

Pro Pro Ile Thr Phe Gly Gln Gly Thr Arg Leu Glu Ile Lys Arg Cys
            100                 105                 110

<210> SEQ ID NO 55
<211> LENGTH: 112
<212> TYPE: PRT
<213> ORGANISM: Homo sapiens

<400> SEQUENCE: 55

Asn Gly Ile Val Leu Thr Gln Ser Pro Gly Thr Leu Ser Leu Ser Pro
 1               5                  10                  15

Gly Glu Arg Ala Thr Phe Ser Cys Arg Ala Ser Gln Ser Gly Ser Ser
            20                  25                  30

Thr Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Tyr Gly Arg Ser
                 85                  90                  95

Pro Pro Ile Thr Phe Gly Gln Gly Thr Arg Leu Glu Ile Lys Arg Cys
            100                 105                 110

<210> SEQ ID NO 56
<211> LENGTH: 808
<212> TYPE: PRT
<213> ORGANISM: Homo sapiens

<400> SEQUENCE: 56

Cys Pro Ala Asn Cys Val Cys Ser Lys Thr Glu Ile Asn Cys Arg Arg
```

```
            1               5                   10                  15
Pro Asp Asp Gly Asn Leu Phe Pro Leu Glu Gly Gln Asp Ser Gly
                20                  25                  30
Asn Ser Asn Gly Asn Ala Asn Ile Asn Ile Thr Asp Ile Ser Arg Asn
            35                  40                  45
Ile Thr Ser Ile His Ile Glu Asn Trp Arg Ser Leu His Thr Leu Asn
        50                  55                  60
Ala Val Asp Met Glu Leu Tyr Thr Gly Leu Gln Lys Leu Thr Ile Lys
65                  70                  75                  80
Asn Ser Gly Leu Arg Ser Ile Gln Pro Arg Ala Phe Ala Lys Asn Pro
                85                  90                  95
His Leu Arg Tyr Ile Asn Leu Ser Ser Asn Arg Leu Thr Thr Leu Ser
            100                 105                 110
Trp Gln Leu Phe Gln Thr Leu Ser Leu Arg Glu Leu Gln Leu Glu Gln
                115                 120                 125
Asn Phe Phe Asn Cys Ser Cys Asp Ile Arg Trp Met Gln Leu Trp Gln
            130                 135                 140
Glu Gln Gly Glu Ala Lys Leu Asn Ser Gln Asn Leu Tyr Cys Ile Asn
145                 150                 155                 160
Ala Asp Gly Ser Gln Leu Pro Leu Phe Arg Met Asn Ile Ser Gln Cys
                165                 170                 175
Asp Leu Pro Glu Ile Ser Val Ser His Val Asn Leu Thr Val Arg Glu
            180                 185                 190
Gly Asp Asn Ala Val Ile Thr Cys Asn Gly Ser Gly Ser Pro Leu Pro
                195                 200                 205
Asp Val Asp Trp Ile Val Thr Gly Leu Gln Ser Ile Asn Thr His Gln
            210                 215                 220
Thr Asn Leu Asn Trp Thr Asn Val His Ala Ile Asn Leu Thr Leu Val
225                 230                 235                 240
Asn Val Thr Ser Glu Asp Asn Gly Phe Thr Leu Thr Cys Ile Ala Glu
                245                 250                 255
Asn Val Val Gly Met Ser Asn Ala Ser Val Ala Leu Thr Val Tyr Tyr
                260                 265                 270
Pro Pro Arg Val Val Ser Leu Glu Glu Pro Glu Leu Arg Leu Glu His
            275                 280                 285
Cys Ile Glu Phe Val Val Arg Gly Asn Pro Pro Thr Leu His Trp
            290                 295                 300
Leu His Asn Gly Gln Pro Leu Arg Glu Ser Lys Ile Ile His Val Glu
305                 310                 315                 320
Tyr Tyr Gln Glu Gly Glu Ile Ser Glu Gly Cys Leu Leu Phe Asn Lys
                325                 330                 335
Pro Thr His Tyr Asn Asn Gly Asn Tyr Thr Leu Ile Ala Lys Asn Pro
            340                 345                 350
Leu Gly Thr Ala Asn Gln Thr Ile Asn Gly His Phe Leu Lys Glu Pro
                355                 360                 365
Phe Pro Glu Ser Thr Asp Asn Phe Ile Leu Phe Asp Glu Val Ser Pro
            370                 375                 380
Thr Pro Pro Ile Thr Val Thr His Lys Pro Glu Glu Asp Thr Phe Gly
385                 390                 395                 400
Val Ser Ile Ala Val Gly Leu Ala Ala Phe Ala Cys Val Leu Leu Val
                405                 410                 415
Val Leu Phe Val Met Ile Asn Lys Tyr Gly Arg Arg Ser Lys Phe Gly
            420                 425                 430
```

Met Lys Gly Pro Val Ala Val Ile Ser Gly Glu Asp Ser Ala Ser
            435                 440                 445

Pro Leu His His Ile Asn His Gly Ile Thr Thr Pro Ser Ser Leu Asp
        450                 455                 460

Ala Gly Pro Asp Thr Val Val Ile Gly Met Thr Arg Ile Pro Val Ile
465                 470                 475                 480

Glu Asn Pro Gln Tyr Phe Arg Gln Gly His Asn Cys His Lys Pro Asp
                485                 490                 495

Thr Tyr Val Gln His Ile Lys Arg Arg Asp Ile Val Leu Lys Arg Glu
            500                 505                 510

Leu Gly Glu Gly Ala Phe Gly Lys Val Phe Leu Ala Glu Cys Tyr Asn
        515                 520                 525

Leu Ser Pro Thr Lys Asp Lys Met Leu Val Ala Val Lys Ala Leu Lys
        530                 535                 540

Asp Pro Thr Leu Ala Ala Arg Lys Asp Phe Gln Arg Glu Ala Glu Leu
545                 550                 555                 560

Leu Thr Asn Leu Gln His Glu His Ile Val Lys Phe Tyr Gly Val Cys
                565                 570                 575

Gly Asp Gly Asp Pro Leu Ile Met Val Phe Glu Tyr Met Lys His Gly
            580                 585                 590

Asp Leu Asn Lys Phe Leu Arg Ala His Gly Pro Asp Ala Met Ile Leu
        595                 600                 605

Val Asp Gly Gln Pro Arg Gln Ala Lys Gly Glu Leu Gly Leu Ser Gln
        610                 615                 620

Met Leu His Ile Ala Ser Gln Ile Ala Ser Gly Met Val Tyr Leu Ala
625                 630                 635                 640

Ser Gln His Phe Val His Arg Asp Leu Ala Thr Arg Asn Cys Leu Val
                645                 650                 655

Gly Ala Asn Leu Leu Val Lys Ile Gly Asp Phe Gly Met Ser Arg Asp
            660                 665                 670

Val Tyr Ser Thr Asp Tyr Tyr Arg Leu Phe Asn Pro Ser Gly Asn Asp
        675                 680                 685

Phe Cys Ile Trp Cys Glu Val Gly Gly His Thr Met Leu Pro Ile Arg
        690                 695                 700

Trp Met Pro Pro Glu Ser Ile Met Tyr Arg Lys Phe Thr Thr Glu Ser
705                 710                 715                 720

Asp Val Trp Ser Phe Gly Val Ile Leu Trp Glu Ile Phe Thr Tyr Gly
                725                 730                 735

Lys Gln Pro Trp Phe Gln Leu Ser Asn Thr Glu Val Ile Glu Cys Ile
            740                 745                 750

Thr Gln Gly Arg Val Leu Glu Arg Pro Arg Val Cys Pro Lys Glu Val
        755                 760                 765

Tyr Asp Val Met Leu Gly Cys Trp Gln Arg Glu Pro Gln Gln Arg Leu
        770                 775                 780

Asn Ile Lys Glu Ile Tyr Lys Ile Leu His Ala Leu Gly Lys Ala Thr
785                 790                 795                 800

Pro Ile Tyr Leu Asp Ile Leu Gly
                805

<210> SEQ ID NO 57
<211> LENGTH: 2607
<212> TYPE: DNA
<213> ORGANISM: Homo sapiens

<400> SEQUENCE: 57

```
tgccctgcaa attgtgtctg cagcaagact gagatcaatt gccggcggcc ggacgatggg      60
aacctcttcc ccctcctgga agggcaggat tcagggaaca gcaatgggaa cgccaatatc     120
aacatcacgg acatctcaag gaatatcact tccatacaca tagagaactg gcgcagtctt     180
cacacgctca acgccgtgga catggagctc tacaccggac ttcaaaagct gaccatcaag     240
aactcaggac ttcggagcat tcagcccaga gcctttgcca agaaccccca tttgcgttat     300
ataaacctgt caagtaaccg gctcaccaca ctctcgtggc agctcttcca gacgctgagt     360
cttcgggaat tgcagttgga gcagaacttt ttcaactgca gctgtgacat ccgctggatg     420
cagctctggc aggagcaggg ggaggccaag ctcaacagcc agaacctcta ctgcatcaat     480
gctgatggct cccagcttcc tctcttccgc atgaacatca gtcagtgtga ccttcctgag     540
atcagcgtga gccacgtcaa cctgaccgta cgagagggtg acaatgctgt tatcacttgc     600
aatggctctg gatcacccct tcctgatgtg gactggatag tcactgggct gcagtccatc     660
aacactcacc agaccaatct gaactggacc aatgttcatg ccatcaactt gacgctggtg     720
aatgtgacga gtgaggacaa tggcttcacc ctgacgtgca ttgcagagaa cgtggtgggc     780
atgagcaatg ccagtgttgc cctcactgtc tactatcccc cacgtgtggt gagcctggag     840
gagcctgagc tgcgcctgga gcactgcatc gagtttgtgg tgcgtggcaa ccccccacca     900
acgctgcact ggctgcacaa tgggcagcct ctgcgggagt ccaagatcat ccatgtggaa     960
tactaccaag agggagagat ttccgagggc tgcctgctct tcaacaagcc cacccactac    1020
aacaatggca actataccct cattgccaaa aacccactgg gcacagccaa ccagaccatc    1080
aatgccact tcctcaagga gccctttcca gagagcacgg ataactttat cttgtttgac    1140
gaagtgagtc ccacacctcc tatcactgtg acccacaaac cagaagaaga cacttttggg    1200
gtatccatag cagttggact tgctgctttt gcctgtgtcc tgttggtggt tctcttcgtc    1260
atgatcaaca aatatggtcg acggtccaaa tttggaatga agggtcccgt ggctgtcatc    1320
agtggtgagg aggactcagc cagcccactg caccacatca ccacggcat caccacgccc    1380
tcgtcactgg atgccgggcc cgacactgtg gtcattggca tgactcgcat ccctgtcatt    1440
gagaaccccc agtacttccg tcagggacac aactgccaca gcccggacac gtatgtgcag    1500
cacattaaga ggagagacat cgtgctgaag cgagaactgg gtgagggagc ctttggaaag    1560
gtcttcctgg ccgagtgcta caacctcagc ccgaccaagg acaagatgct tgtggctgtg    1620
aaggcctga aggatccac cctggctgcc cggaaggatt ccagaggga ggccgagctg    1680
ctcaccaacc tgcagcatga gcacattgtc aagttctatg gagtgtgcgg cgatggggac    1740
cccctcatca tggtctttga atacatgaag catggagacc tgaataagtt cctcagggcc    1800
catgggccag atgcaatgat ccttgtggat ggacagccac gccaggccaa gggtgagctg    1860
gggctctccc aaatgctcca cattgccagt cagatcgcct cgggtatggt gtacctggcc    1920
tcccagcact tgtgcaccg agacctggcc accaggaact gcctggttgg agcgaatctg    1980
ctagtgaaga ttgggggactt cggcatgtcc agagatgtct acagcacgga ttattacagg    2040
ctctttaatc catctggaaa tgattttttgt atatggtgtg aggtgggagg acacaccatg    2100
ctccccattc gctggatgcc tcctgaaagc atcatgtacc ggaagttcac tacagagagt    2160
gatgtatgga gcttcggggt gatcctctgg gagatcttca cctatggaaa gcagccatgg    2220
ttccaactct caaacacgga ggtcattgag tgcattaccc aaggtcgtgt tttggagcgg    2280
ccccgagtct gccccaaaga ggtgtacgat gtcatgctgg ggtgctggca gagggaacca    2340
```

```
cagcagcggt tgaacatcaa ggagatctac aaaatcctcc atgctttggg gaaggccacc    2400
ccaatctacc tggacattct tggctagtgg tggctggtgg tcatgaattc atactctgtt    2460
gcctcctctc tccctgcctc acatctccct tccacctcac aactccttcc atccttgact    2520
gaagcgaaca tcttcatata aactcaagtg cctgctacac atacaacact gaaaaaagga    2580
aaaaaaaaga aaaaaaaaaa aaaccgc                                         2607

<210> SEQ ID NO 58
<211> LENGTH: 360
<212> TYPE: DNA
<213> ORGANISM: Murine

<400> SEQUENCE: 58
caggtccaac tgcagcagtc tggggctgag ctgatgcagc ctggggcctc agtgaagata     60
tcctgcaagt ctactggcta cacattcagt aacttctgga tagagtgggt aaagcagagg    120
cctggacatg gccttgagtg gattggagag atttttacctg gcagtgataa tactaactac    180
aatgagaagt tcaagggcaa ggccacattc actgcagata catcctccaa cacagcctac    240
atgcaactca gcagcctgac atctgaggac tctgccgtct attactgtgc aagaaagaat    300
cgtaactact atggtaacta cgttgtatgg ggccaaggga ctctggtcac tgtctctgca    360

<210> SEQ ID NO 59
<211> LENGTH: 330
<212> TYPE: DNA
<213> ORGANISM: Murine

<400> SEQUENCE: 59
gacattgtga tgacccagtc tcctgcttcc ttagctgtat ctctggggca gagggccacc     60
atctcataca gggccagcaa agtgtcagt acatctggct atagttatat gcactggaac     120
caacagaaac caggacagcc acccagactc ctcatctatc ttgtatccaa cctagaatct    180
ggggtccctg ccaggttcag tggcagtggg tctgggacag acttcaccct caacatccat    240
cctgtggagg aggaggatgc tgcaacctat tactgtcagc acattaggga gcttacacgt    300
tcggctcggg gacaaagttg gaaaaaacgg                                      330

<210> SEQ ID NO 60
<211> LENGTH: 360
<212> TYPE: DNA
<213> ORGANISM: Murine

<400> SEQUENCE: 60
caggtccagc tgcagcagtc tggagctgag ctgatgcagc ctggggcctc agtgaagata     60
tcctgcaagt ctactggcta cacattcagt aacttctgga tagagtgggt aaagcagagg    120
cctggacatg gccttgagtg gattggagag atttttacctg gcagtgataa tactaactac    180
aatgagaagt tcaagggcaa ggccacattc actgcagata catcctccaa cacagcctac    240
atgcaactca gcagcctgac atctgaggac tctgccgtct attactgtgc aagaaagaat    300
cgtaactact atggtaacta cgttgtctgg ggcgcaggca ccactctcac agtctcctca    360

<210> SEQ ID NO 61
<211> LENGTH: 321
<212> TYPE: DNA
<213> ORGANISM: Murine

<400> SEQUENCE: 61
```

```
caaattgtgc tgacccagtc tccagcaatc atgtctgcat ctccagggga gaaggtcacc    60
ataacctgca gtgccagctc aagtgtaagt tacatgtact ggttccagca gaagccaggc   120
acttctccca aactctggat ttatagtaca tccaacctgg cttctggagt ccctgctcgc   180
ttcagtggca gtggatctgg gacctcttac tctctcacaa tcagccgaat ggaggctgaa   240
gatgctgcca cttattactg ccagcaaagg agtagttacc cgctcacgtt cggtgctggg   300
accaagctgg aactaaaacg g                                             321
```

<210> SEQ ID NO 62
<211> LENGTH: 372
<212> TYPE: DNA
<213> ORGANISM: Murine

<400> SEQUENCE: 62

```
caggtccagc tgcagcagcc tggggctgaa ctggtgaagc ctggggcttc agtgaagctg    60
tcctgcaagg cttctggcta cacttcacc agctactgga tgcactgggt gaagcagagg   120
cctggacaag ccttgagtg gattggagag atttatccta gcaacggtcg tactaactac   180
aatgagaagt tcaagagcaa ggccacactg actgtagaca atcctccag cacagcctac   240 atgcaactca gcagcctgac atctgaggac tctgcggtct attactgtgc aagaaaatat   300
tactacggta atagcatcg ttcctggtac ttcgatgtct ggggcgcagg caccactctc   360
acagtctcct ca                                                       372
```

<210> SEQ ID NO 63
<211> LENGTH: 336
<212> TYPE: DNA
<213> ORGANISM: Murine

<400> SEQUENCE: 63

```
gacattgtgc tgacccagtc tccagcttct ttggctgtgt ctctagggca gagggccacc    60
atctcctgca gagccagcga aagtgttgat aattatggca ttagttttat gaactggttc   120
caacagaaac caggacagcc acccaaactc ctcatctatg ctgcatccaa ccaaggatcc   180
ggggtccctg ccaggtttag tggcagtggg tctgggacag acttcagcct caacatccat   240
cctatggagg aggatgatac tgcaatgtat ttctgtcagc aaagtaagga ggttcctcgg   300
acgttcggtg aggcaccaa gctggagatg aaacgg                              336
```

<210> SEQ ID NO 64
<211> LENGTH: 381
<212> TYPE: DNA
<213> ORGANISM: Homo sapiens

<400> SEQUENCE: 64

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag aaaagggcct ggagtggatt gggtacatct tttacagtgg gaggacctac   180
tacaacccgt ccctcaagag tcgagttacc atatcagtag acacgtctaa gaaccagttc   240
tccctgaagc tgaactctgt gactgccgcg gacacggccg tgtattactg tgcgagagag   300
cggatagcag cagctggtgc ggactactac tacaacggtt tggacgtctg gggccaaggg   360
accacggtca ccgtctcctc a                                             381
```

<210> SEQ ID NO 65
<211> LENGTH: 330
<212> TYPE: DNA

<213> ORGANISM: Homo sapiens

<400> SEQUENCE: 65

```
gaaattgtgt tgacgcagtc tccaggcacc ctgtctttgt ctccagggga aagagccacc    60
ctctcctgca gggccagtca gagtgttagc agcaactact taacctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggtc gctcacctcc gatcaccttc   300
ggccaaggga cacgactgga gattaaacga                                     330
```

<210> SEQ ID NO 66
<211> LENGTH: 381
<212> TYPE: DNA
<213> ORGANISM: Homo sapiens

<400> SEQUENCE: 66

```
caggtgcagc tgcaggagtc gggcccagga ctggtgaagc cttcacagac cctgtccctc    60
acctgcactg tctctggtgg ctccatcagc agtggttatt attattggag ctggatccgc   120
cagcacccag ggaagggcct ggagtggatt gggtacatct attacagtgg gagcacctac   180
tacaacccgt ccctcaagag tcgacttacc atatcagtag acacgtctaa gaaccagttc   240
tccctgaagc tgagctctgt gactgccgcg gacacggccg tgtattactg tgcgagagag   300
cggatagcag cagctggaac ggactactac tacaacggtt tggccgtctg ggggccaaggg  360
accacggtca ccgtctcctc a                                             381
```

<210> SEQ ID NO 67
<211> LENGTH: 330
<212> TYPE: DNA
<213> ORGANISM: Homo sapiens

<400> SEQUENCE: 67

```
ggaattgtgt tgacgcagtc tccaggcacc ctgtctttgt ctccagggga aagagccact    60
ttctcctgca gggccagtca gagtggtagc agcacctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta ggtcacctcc gatcaccttc   300
ggccaaggga cacgactgga gattaaacga                                     330
```

<210> SEQ ID NO 68
<211> LENGTH: 384
<212> TYPE: DNA
<213> ORGANISM: Homo sapiens

<400> SEQUENCE: 68

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcaccaac   180
tacaacccgt ccctcaagag tcgagttacc atatcagtgg acacgtctaa gaaccagttc   240
tccctgaagc tgagctctgt gactgccgcg gacacggccg tgtattactg tacgagagat   300
cgggactatg atagtaccgg ggattactac tcctactacg gtatggacgt ctggggccaa   360
gggaccacgg tcaccgtctc ctca                                          384
```

<210> SEQ ID NO 69
<211> LENGTH: 324
<212> TYPE: DNA
<213> ORGANISM: Homo sapiens

<400> SEQUENCE: 69

```
gatatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttttta ctgtctacag cataatagtc ttccgctcac tttcggcgga     300
gggaccaagg tggagatcaa acga                                            324
```

<210> SEQ ID NO 70
<211> LENGTH: 354
<212> TYPE: DNA
<213> ORGANISM: Homo sapiens

<400> SEQUENCE: 70

```
caggtgcagc tgcaggagtc gggcccagga ctggtgaggc cttcggagac cctgtccctc      60
acctgcactg tctctggtgg ctccatcagt acttactact ggaactggat ccggcagccc     120
gccgggaagg gactggagtg gattgggcgt atctatacca gtgggagcac caactacaac     180
ccctccctca gagtcgagt caccatgtca gtagacacg ccaagaacca gttctccctg     240
aagctgagct ctgtgaccgc cgcggacacg gccgtgtatt actgtgcgag agatgggggc     300
tacagtaacc cttttgacta ctggggccag ggaaccctgg tcaccgtctc ctca           354
```

<210> SEQ ID NO 71
<211> LENGTH: 342
<212> TYPE: DNA
<213> ORGANISM: Homo sapiens

<400> SEQUENCE: 71

```
gatatccaga tgacccagtc tccagactcc ctggctgtgt ctctgggcga gagggccacc      60
atcaactgca gtccagcca gagtgtttca tacagctcca acaataagaa ctacttagct     120
tggtaccagc agaaacctgg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcaacaaca ttataatact     300
ccactcactt tcggcggagg gaccaaggtg gagatcaaac ga                        342
```

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 72

```
cagcagaaca aggtcctgga a                                                21
```

<210> SEQ ID NO 73
<211> LENGTH: 19
<212> TYPE: DNA
<213> ORGANISM: Artificial Sequence
<220> FEATURE:

```
<223> OTHER INFORMATION: Synthetic oligonucleotide

<400> SEQUENCE: 73
agcgggaagg ctctgagtg                                                    19

<210> SEQ ID NO 74
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 74
agctgttggt gctgcgccag aa                                                22

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 75
tccattgaag acccattcga c                                                 21

<210> SEQ ID NO 76
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 76
gccgacattg gctgtgaac                                                    19

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 77
aggatgactg ggcagcttgg tcca                                              24

<210> SEQ ID NO 78
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 78
cagcccactg caccatatca                                                   20

<210> SEQ ID NO 79
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 79
ctgtatccgg cccagcat                                                     18
```

```
<210> SEQ ID NO 80
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 80
ccatggcatc actacacctt catcgct                                              27

<210> SEQ ID NO 81
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 81
tgggaaaatt gagatggcag a                                                    21

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
gctgcctgaa gcacaaaagg                                                      20

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 83
cgcagatcct gccaaccgaa gaga                                                 24

<210> SEQ ID NO 84
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 84
gacaccactc ttctggaaaa tgc                                                  23

<210> SEQ ID NO 85
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 85
ttgccaaacc aacacctacc a                                                    21

<210> SEQ ID NO 86
<211> LENGTH: 26
<212> TYPE: DNA
<213> ORGANISM: Artificial Sequence
<220> FEATURE:
<223> OTHER INFORMATION: Synthetic oligonucleotide
```

```
-continued

<400> SEQUENCE: 86
atcggacacc acctgtaggg aggacc                                          26

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
cagtggcaaa gtggagattg t                                               21

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
aatttgccgt gagtggagtc                                                 20

<210> SEQ ID NO 89
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 89
ccatcaacga ccccttcatt gacctc                                          26
```

AGONIST ANTI-TRK-C MONOCLONAL ANTIBODIES

REFERENCE TO RELATED APPLICATIONS

The present application is the U.S. National Phase of International Application PCT/US01/20153, filed Jun. 22, 2001 and claims priority under 35 U.S.C. §119(e) to U.S. Provisional Application Nos. 60/213,141 filed Jun. 22, 2000 and 60/238,319 filed Oct. 5, 2000.

BACKGROUND OF THE INVENTION

1. Field of the Invention

This invention concerns agonist anti-trkC monoclonal antibodies. It further concerns the use of the agonist antibodies in the prevention and/or treatment of cellular degeneration, including nerve cell damage associated with acute nervous cell system injury and chronic neurodegenerative diseases, including peripheral neuropathy.

2. Description of the Related Art

Neurotrophins are a family of small, basic proteins, which play a crucial role in the development and maintenance of the nervous system. The first identified and probably best understood member of this family is nerve growth factor (NGF), which has prominent effects on developing sensory and sympathetic neurons of the peripheral nervous system (Levi-Montalcini, R. and Angeletti, P. U., *Physiol. Rev.* 48, 534-569 [1968]; Thoenen, H. et al., *Rev. Physiol. Biochem. Pharmacol.* 109, 145-178 [1987]). Although NGF had been known for a long time, including a homolog from the mouse submandibular gland, the mature, active form of which is often referred to as - or 2.5S NGF, it was only many years later that sequentially related but distinct polypeptides with similar functions were identified.

The first in line was a factor called brain-derived neurotrophic factor (BDNF), which was cloned and sequenced by Leibrock, J. et al. (*Nature* 341, 149-152 [1989]). This factor was originally purified from pig brain (Barde, Y. A. et al., *EMBO J.* 1, 549-553 [1982]), but it was not until its cDNA was cloned and sequenced that its homology with NGF became apparent. The overall amino acid sequence identity between NGF and BNDF is about 50%. In view of this finding, Leibrock et al. speculated that there was no reason to think that BDNF and NGF should be the only members of a family of neurotrophins having in common structural and functional characteristics.

Indeed, further neurotrophins closely related to -NGF and BDNF have since been discovered. Several groups identified a neurotrophin originally called neuronal factor (NF), and now referred to as neurotrophin-3 (NT-3) (Ernfors et al., *Proc. Natl. Acad. Sci. USA* 87, 5454-5458 (1990); Höhn et al., *Nature* 344, 339 [1990]; Maisonpierre et al., *Science* 247, 1446 [1990]; Rosenthal et al., *Neuron* 4, 767 [1990]; Jones and Reichardt, *Proc. Natl. Acad. Sci. USA* 87, 8060-8064 (1990); Kaisho et al., *FEBS Lett.* 266, 187 [1990]. NT-3 shares about 50% of its amino acids with both -NGF and BDNF (NT-2). Neurotrophins-4 and -5 (NT-4 and NT-5), have been added to the family (U.S. Pat. No. 5,364,769 issued Nov. 15, 1994; Hallbook, F. et al., *Neuron* 6, 845-858 [1991]; Berkmeier, L. R. et al., *Neuron* 7, 857-866 [1991]; lp et al., *Proc. Natl. Acad. Sci USA* 89, 3060-3064 [1992]). The mammalian molecule initially described by Berkmeier et al supra, which was subsequently seen to be the homolog of *Xenopus* NT-4, is usually referred to as NT-4/5. In addition, there is an acidic homologous protein described in mammals which is referred to as NT-6 (Berkemeir, et al., *Somat. Cell Mol. Genet* 18(3):233-245 [1992]). More recently, another homologus protein from the fish, *Xiphophorus* has also been labeled NT-6 (Gotz et al., *Nature* 372:266-269 [1994]). There are two proteins described in the literature as NT-7, one cloned from the carp, *Cyprinus*, (Lai, et al., *Mol. Cell. Neurosci.* 11(1-2):64-76 [1998]) and one from the zebrafish, *Danio* (Nilsson et al., *FEBS Letters* 424(3):285-90 [1998]). None of these last three described fish neurotrophins has been described outside fish, and their relationship to any mammalian neurotrophins is unclear. The amino acid sequence of zebrafish neurotrophin-7 (zNT-7) is more closely related to that of fish nerve growth factor (NGF) and neurotrophin-6 (NT-6) than to that of any other neurotrophin. zNT-7 is, however, equally related to fish NGF and NT-6 (65% and 63% amino acid sequence identity, respectively) indicating that it represents a distinct neurotrophin sequence. zNT-7 contains a 15 amino acid residue in a beta-turn region in the middle of the mature protein. Recombinant zNT-7 was able to bind to the human p75 neurotrophin receptor and to induce tyrosine phosphorylation of the rat trkA receptor tyrosine kinase, albeit less efficiently than rat NGF. zNT-7 did not interact with rat trkB or trkC, indicating a similar receptor specificity as NGF. We propose that a diversification of the NGF subfamily in the neurotrophin evolutionary tree occurred during the evolution of teleost fishes which in the appearance of several additional members, such as zNT-7 and NT-6, is structurally and functionally related to NGF.

Neurotrophins, similarly to other polypeptide growth factors, affect their target cells through interactions with cell surface receptors. According to our current knowledge, two kinds of transmembrane glycoproteins serve as receptors for neurotrophins. Equilibrium binding studies have shown that neurotrophin-responsive neurons possess a common low molecular weight (65-80 kDa), low affinity receptor (LNGFR), also termed as $p75^{NTR}$ or p75, which binds NGF, BDNF, and NT-3 with a $K_D$ of $2 \times 10^{-9}$ M, and large molecular weight (130-150 kDa), high affinity ($K_D$ in the $10^{-11}$ M) receptors, which are members of the trk family of the receptor tyrosine kinases.

The first member of the trk receptor family, trkA, was initially identified as the result of an oncogenic transformation caused by the translocation of tropomyosin sequences onto its catalytic domain (Martin-Zanca et al., *Mol. Cell. Biol.* 9(1):24-33 [1989]). Later work identified trkA as a signal transducing receptor for NGF. Subsequently, two other related receptors, mouse and rat trkB (Klein et al., *EMBO J.* 8, 3701-3709 [1989]; Middlemas et al., *Mol. Cell. Biol.* 11, 143-153 [1991]; EP 455,460 published 6 Nov. 1991) and porcine, mouse and rat trkC (Lamballe et al., *Cell* 66, 967-979 [1991]; EP 522,530 published 13 Jan. 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain).

The role of the p75 and trk receptors is controversial. It is generally accepted that trk receptor tyrosine kinases play an important role in conferring binding specificity to a particular neurotrophin, however, cell lines expressing trkA bind not only NGF but also NT-3 and NT-415 (but not BDNF), trkB expressing cells bind BDNF, NT-3, NT-4, and NT-415 (but not NGF), in contrast to trkC-expressing cells which have been reported to bind NT-3 alone (but not the other neurotrophins). Furthermore, it has been shown in model systems that the various forms of trk receptors, arising from alternate splicing events, can activate different intracellular signalling pathways, and therefore presumably mediate different physiological functions in vivo. It is unclear whether cells expressing a given trk receptor in the absence of p75 bind neurotrophins with low or high affinity (Meakin and Shooter, *Trends Neurosci.* 15, 323-331 [1992]).

Published results of studies using various cell lines are confusing and suggest that p75 is either essential or dispensable for neurotrophin responsiveness. Cell lines that express p75 alone bind NGF, BDNF, NT-3, and NT-4 with similar low affinity at equilibrium, but the binding rate constants are remarkably different. As a result, although p75-binding is a common property of all neurotrophins, it has been suggested the p75 receptor may also play a role in ligand discrimination (Rodriguez-Tebar et al., *EMBO J.* 11, 917-922 [1992]). While the trk receptors have been traditionally thought of as the biologically significant neurotrophin receptors, it has recently been demonstrated that in melanoma cells devoid of trkA expression, NGF can still elicit profound changes in biological behavior presumably through p75 (Herrmann et al., *Mol. Biol. Cell* 4, 1205-1216 [1993]). Davies et al. (*Neuron* 11, 565-574 [1993]) reported the results of studies investigating the role of p75 in mediating the survival response of embryonic neurons to neurotrophins in a model of transgenic mice carrying a null mutation in the p75 gene. They found that p75 enhances the sensitivity of NGF-dependent cutaneous sensory neurons to NGF. There have now been many studies showing that p75 is capable of mediating at least some of the biological effects of the neurotrophins. The field is still somewhat controversial, but p75 signaling has been implicated in controlling cell death, and neurite outgrowth. (Barker, P A, *Cell Death Diff.* 5:346-356 [1998]; Bredesen et al., *Cell Death Diff.* 5:357-364 [1998]; Casaccia-Bonnefil, et al., *Cell Death Diff.* 5:357-364 [1998]; Raoul et al., *Curr. Op. Neurobiol.* 10:111-117 [2000]; Davies, A M, *Curr. Biol.* 10:R198-R200 [2000]). Importantly, stimulation of p75 has been shown to modify the effects of stimulating trkC (Hapner, et al., *Developm. Biol.* 201:90-100 [1998]).

The extracellular domains of full-length native trkA, trkB and trkC receptors have five functional domains, that have been defined with reference to homologous or otherwise similar structures identified in various other proteins. The domains have been designated starting at the N-terminus of the amino acid sequence of the mature trk receptors as 1) a first cysteine-rich domain extending from amino acid position 1 to about amino acid position 32 of human trkA, from amino acid position 1 to about amino acid position 36 of human trkB, and from amino acid position 1 to about amino acid position 48 of human trkC; 2) a leucine-rich domain stretching from about amino acid 33 to about amino acid to about amino acid 104 in trkA; from about amino acid 37 to about amino acid 108 in trkB, and from about amino acid 49 to about amino acid 120 in trkC; 3) a second cysteine-rich domain from about amino acid 105 to about amino acid 157 in trkA; from about amino acid 109 to about amino acid 164 in trkB; and from about amino acid 121 to about amino acid 177 in trkC; 4) a first immunoglobulin-like domain stretching from about amino acid 176 to about amino acid 234 in trkA; from about amino acid 183 to about amino acid 239 in trkB; and from about amino acid 196 to about amino acid 257 in trkC; and 5) a second immunoglobulin-like domain extending from about amino acid 264 to about amino acid 330 in trkA; from about amino acid 270 to about amino acid 334 in trkB; and from about amino acid 288 to about amino acid 351 in trkC.

Neurotrophins exhibit actions on distinct, but overlapping, sets of peripheral and central neurons. These effects range from playing a crucial role in ensuring the survival of developing neurons (NGF in sensory and sympathetic neurons) to relatively subtle effects on the morphology of neurons (NT-3 on purkinje cells). These activities have led to interest in using neurotrophins as treatments of certain neurodegenerative diseases. NT-3 has also been found to promote proliferation of peripheral blood leukocytes and, as a result, it has been suggested that NT-3 can be used in the treatment of neutropenia, infectious disease and tumors (U.S. Pat. No. 6,015,552 issued on Jun. 18, 2000).

The roles of neurotrophins in regulating cardiovascular development and modulating the vascular response to injury have also been investigated (Donovan et al., *Nature Genetics* 14:210-213 [1996]; Donovan et al., *A.J. Path.* 147:309-324 [1995]; Kraemer et al., *Arteriol. Thromb. and Vasc. Biol.* 19:1041-1050 [1999]). Neurotrophins have been described as potential therapeutics for regulating angiogenesis and vascular integrity (PCT Publication WO 00/24415, published May 4, 2000).

Despite their promise in the treatment of cellular degeneration, such as occurs due to neurodegenerative disease and acute neuronal injuries, and potentially angiogenesis, neurotrophins have several shortcomings. One significant shortcoming is the lack of specificity. Most neurotrophins cross-react with more than one receptor. For example NT-3, the preferred ligand of the trkC receptor tyrosine kinase, also binds to and activates trkA and trkB (Barbacid, *J. Neurobiol.* 25:1386-1403 [1994]; Barbarcid, *Ann. New York Acad. Sci.* 766:442-458 [1995]; Ryden and Ibanez, *J. Biol. Chem.* 271: 5623-5627 [1996]; Belliveau et al., *J. Cell. Biol.* 136:375-388 [1997]; Farinas et al., *Neuron* 21:325-334 [1998]). As a result, it is difficult to devise therapies that target a specific population of neurons. Another limitation of neurotrophin therapy is that neurotrophins, including NT-3 are known to elicit hyperalgesia (Chaudhry, et al., *Muscle and Nerve* 23:189-192 [2000]). In addition, some neurotrophins such as NT-3 have poor pharmacokinetic and bioavailability properties in rodents, which raise serious questions about their human clinical applications (Haase et al., *J. Neurol. Sci.* 160:S97-S105 [1998], dosages used in Helgren et al., *J. Neurosci.* 17(1):372-82 [1997], and data below).

Accordingly, there is a great need for the development of new therapeutic agents for the treatment of neurodegenerative disorders and acute nerve cell injuries that are devoid of the known shortcomings of neurotrophins.

SUMMARY OF THE INVENTION

The current invention is based on the development and characterization of agonist anti-trkC monoclonal antibodies, directed against epitopes in the extracellular domain of trkC receptor, which mimic the biological activities of NT-3, the natural ligand of trkC receptor but are free of some of the known detriments of NT-3. The invention also demonstrates the usefulness of these agonist antibodies in the treatment of neuropathy in an experimental animal model. Anti-trkC agonist antibodies offer numerous advantages over NT-3 in prophylactic or therapeutic treatment of cellular degeneration, such as nerve cell damage, in particular nerve cell injury associated with neurodegenerative diseases, such as peripheral neuropathies or due to external factors, such as trauma, toxic agents, surgery, just to mention a few.

In one aspect, the invention concerns an agonist anti-trkC monoclonal antibody which
   (a) shows no significant cross-reactivity with trkA or trkB; and
   (b) recognizes an epitope in domain 5 of trkC.

Certain agonist antibodies of the present invention may additionally recognize an epitope in domain 4 of trkC. In a preferred embodiment, the antibodies bind both human and rodent (e.g. rat or mouse) trkC, and may be murine, chimeric (including humanized) or human antibodies. The antibodies mimic at least one activity of the native trkC ligand, NT-3, and may thus be effective in the prevention and/or treatment of various diseases involving cellular degeneration, including, for example, neuropathies, such as cisplatin- or pyridoxine-induced neuropathy, or diabetic neuropathy, and (where cellular degeneration involves bone marrow cell degeneration) disorders of insufficient blood cells, such as leukopenias including eosinopenia and/or basopenia, lymphopenia, monocytopenia, and neutropenia. In a particularly preferred embodiment, the agonist antibodies of the present invention show superior properties over NT-3, for example, do not cause hyperalgesia when administered to a patient, have increased bioavailability and/or higher specific activity as compared to NT-3.

In another aspect, the invention concerns an anti-trkC antibody heavy chain comprising the following CDR's: a CDR1 selected from the group consisting of SEQ ID NOs: 1, 2, 3, 4 and 5; a CDR2 selected from the group consisting of SEQ ID NOs: 6, 7, 8, 9, 10 and 11; and a CDR3 selected from the group consisting of SEQ ID NOs: 12, 13, 14, 15, 16 and 17.

In yet another aspect, the invention concerns an anti-trkC antibody light chain comprising the following CDR's: a CDR1 selected from the group consisting of SEQ ID NOs: 18, 19, 20, 21, 22, 23 and 24; a CDR2 selected from the group consisting of SEQ ID NOs: 25, 26, 27, 28, 29 and 30; and a CDR3 selected from the group consisting of SEQ ID NOs: 31, 32, 33, 34, 35 and 36.

In a further aspect, the invention concerns a murine anti-trkC antibody heavy chain comprising the following CDR's:

(a) a CDR1 of the formula XaaWXaaXaaWVK (SEQ ID NO: 37), wherein Xaa at position 1 is F or Y; Xaa at position 3 is I or M; and Xaa at position 4 is E or H;

(b) a CDR2 of the formula EIXaaPXaaXaaXaaXaaT-NYNEKFKXaa (SEQ ID NO: 38), wherein Xaa at position 3 is L or Y; Xaa at position 5 is G or S; Xaa at position 6 is S or N; Xaa at position 7 is D or G; Xaa at position 8 is N or R and Xaa at position 16 is G or S; and (c) a CDR3 of the formula KNRNYYGNYVV (SEQ ID NO: 12) or KYYYGNSYRSWYFDV (SEQ ID NO:13).

In a still further aspect, the invention relates to a human anti-trkC antibody heavy chain comprising the following CDR's:

(a) a CDR1 of the formula XaaXaaXaaYYWXaa (SEQ ID NO: 39), wherein Xaa at position 1 is S or I; Xaa at position 2 is G or S; Xaa at position 3 is G, T or Y, and Xaa at position 7 is S or N;

(b) a CDR2 of the formula XaaIXaaXaaSGSXaaTX-aaNPSLKS (SEQ ID NO: 40), wherein Xaa at position 1 is Y or R; Xaa at position 3 is Y or F; Xaa at position 4 is Y or T; Xaa at position 8 is S or R; and Xaa at position 10 is N or Y; and (c) a CDR3 of the formula selected from the group consisting of DRDYDSTGDYYSYYGMDV (SEQ ID NO: 14); DGGYSNPFD (SEQ ID NO: 15); ERIAAAGX-aaDYYYNGLXaaV (SEQ ID NO: 41), wherein Xaa at position 8 is A or T and Xaa at position 16 is D or A.

In another aspect, the invention concerns an anti-trkC agonist monoclonal antibody comprising a heavy chain comprising the CDR's of the murine anti-trkC antibody heavy chain of claim 14 associated with a light chain. The antibody preferably is human or comprises human framework residues, and preferably shows no significant cross-reactivity with trkA or trkB. Throughout the application, antibodies are defined in the broadest sense, and specifically include antibody fragment, such as an Fv fragment, Fab fragment, Fab' or F(ab')$_2$ fragment. Antibodies of all classes and isotypes are included, but IgG, in particular IgG-2 and IgG-4 are preferred.

In yet another aspect, the invention concerns isolated nucleic acid encoding a murine or human anti-trkC agonist antibody heavy or light chain, or a fragment thereof. In a specific embodiment, the nucleic acid is a nucleic acid molecule deposited with ATCC on Jun. 21, 2000 under an accession number selected from the group consisting of PTA-2133, PTA-2134, PTA-2135, PTA-2136, PTA-2137, PTA-2138, PTA-2139, PTA-2140, PTA-2141, PTA-2142 and PTA-2143.

In a further aspect, the invention concerns a vector comprising a nucleic acid molecule encoding an antibody heavy and/or light chain as hereinabove defined. The invention also concerns cells transformed with such nucleic acid. The invention further concerns hybridoma cell lines transformed with such nucleic acid and antibodies produced by such hybridoma cells.

In a still further aspect, the invention concerns a pharmaceutical composition comprising an effective amount of an agonist anti-trkC monoclonal antibody as hereinabove defined in admixture with a pharmaceutically acceptable carrier.

In another aspect, the invention concerns a method for treating a disease or condition involving cell degeneration, comprising administering to a mammal an effective amount of an agonist anti-trkC antibody disclosed herein.

In yet another aspect, the invention concerns a method for treating a neuropathy or neurodegenerative disease, or repairing a damaged nerve cell comprising administering to a mammal an effective amount of an agonist anti-trkC antibody disclosed herein. The neuropathy may, for example, be a peripheral neuropathy, including, without limitation, diabetic neuropathy and large-fiber sensory neuropathies. The neurodegenerative disease may, for example, be amyotrophic lateral sclerosis (ALS), Alzheimer's disease, Parkinson's disease, Huntington's disease. The damaged neurons may be peripheral, such as sensory, e.g. dorsal root ganglia neurons, motor neurons, e.g. neurons from the spinal cord, or central neurons, and the injury may be due to a variety of external and internal factors, including trauma, exposure to neurotoxins, metabolic diseases, infectious agents, etc.

In a further aspect, the invention concerns a method for promoting the development, proliferation, maintenance or regeneration of peripheral neurons, comprising contacting such neurons with an effective amount of an antibody of the present invention.

In a still further aspect, the invention concerns a method for the treatment (including prevention) of a disease or condition involving cell degeneration in a mammalian subject by introducing nucleic acid encoding an anti-trkC antibody herein into a cell of such subject. The method (gene therapy) preferably concerns the treatment of a neuropathy or neurodegenerative disease, or reparation of a damaged nerve cell. Accordingly, the recipient cells preferably are nerve cells.

In yet another aspect, the invention concerns delivery vehicles containing genetic material (nucleic acid) encoding an anti-trkC antibody suitable for gene therapy use.

In an additional aspect, the invention concerns a method of inducing angiogenesis by delivering an anti-trkC antibody of the present invention in an amount effective to induce angiogenesis. The delivery specifically includes the administration of the antibodies and the delivery of nucleic acid encoding the antibodies (e.g. in gene therapy).

In yet another aspect, the invention concerns an isolated nucleic acid molecule encoding a murine or human anti-trkC agonist antibody heavy or light chain selected from the group consisting of SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65; SEQ ID NO: 66; SEQ ID NO: 67, SEQ ID NO: 68, SEQ ID NO: 69, SEQ ID NO: 70 and SEQ ID NO: 71. The present invention also concerns a polypeptide encoded by one or more of the isolated nucleic acid molecules.

In another aspect, the invention concerns a whole cell transformed with nucleic acid encoding murine or human anti-trkC agonist antibody heavy chain, light chain or both heavy and light chain.

BRIEF DESCRIPTION OF THE DRAWINGS

FIG. 1B, murine Mabs). The purified Mabs were assayed for agonist activity in the PC12 neurite outgrowth assay as described in the examples. Rat PC12 cells were transfected with full-length human trkC and the cells plated at a density of 1000 cells/well. Three days following transfection, the Mabs were added in triplicate (concentrations ranging from 0.0002 to 2.7 nM) to the wells containing the trkC transfectants and incubated for an additional 3 days at 37° C. The cells were then analyzed by phase contrast microscopy and cells with neurites exceeding two-times the diameter of the cell were counted.

FIG. 2 shows that agonist anti-trkC monoclonal antibodies bind specifically to trkC using 6.1.2 antibody as a representative example.

FIG. 5 summarizes the results of epitope mapping using competition ELISA.

FIG. 7 shows amino acid sequence of human trkC domain 4 and 5 showing residues that were targeted for mutagenesis to decipher their roles in recognition by agonist anti-trkC monoclonal antibodies.

FIG. 9 shows the amino acid sequence of the heavy chain variable ($V_H$) region from murine and human anti-trkC agonist monoclonal antibodies. In addition, the three CDR regions (CDR1, CDR2 and CDR3) are highlighted in bold. The amino acid sequence of CDR1 of the 2250 and 2253 heavy chain is SEQ ID NO: 1. The amino acid sequence of CDR1 of the 2256 heavy chain is SEQ ID NO: 2. The amino acid sequence of CDR1 of the 6.1.2 and 2345 heavy chain is SEQ ID NO: 3. The amino acid sequence of CDR1 of the 6.4.1 heavy chain is SEQ ID NO: 4. The amino acid sequence of CDR1 of the 2349 heavy chain is SEQ ID NO: 5. The amino acid sequence of CDR2 of the 2250 and 2253 heavy chain is SEQ ID NO: 6. The amino acid sequence of CDR2 of the 2256 heavy chain is SEQ ID NO: 7. The amino acid sequence of CDR2 of the 6.1.2 heavy chain is SEQ ID NO: 8. The amino acid sequence of CDR2 of the 6.4.1 heavy chain is SEQ ID NO: 9. The amino acid sequence of CDR2 of the 2345 heavy chain is SEQ ID NO: 10. The amino acid sequence of CDR2 of the 2349 heavy chain is SEQ ID NO: 11. The amino acid sequence of CDR3 of the 2250 and 2253 heavy chain is SEQ ID NO: 12. The amino acid sequence of CDR3 of the 2256 heavy chain is SEQ ID NO: 13. The amino acid sequence of CDR3 of the 6.1.2 heavy chain is SEQ ID NO: 14. The amino acid sequence of CDR3 of the 6.4.1 heavy chain is SEQ ID NO: 15. The amino acid sequence of CDR3 of the 2345 heavy chain is SEQ ID NO: 16. The amino acid sequence of CDR3 of the 2349 heavy chain is SEQ ID NO: 17.

FIG. 10 shows the amino acid sequence of the light chain variable ($V_L$) region from murine and human anti-trkC agonist monoclonal antibodies. In addition, the three CDR regions (CDR1, CDR2 and CDR3) are highlighted in bold. The amino acid sequence of CDR1 of the 2250 light chain is SEQ ID NO: 18. The amino acid sequence of CDR1 of the 2253 light chain is SEQ ID NO: 19. The amino acid sequence of CDR1 of the 2256 light chain is SEQ ID NO: 20. The amino acid sequence of CDR1 of the 6.1.2 light chain is SEQ ID NO: 21. The amino acid sequence of CDR1 of the 6.4.1 light chain is SEQ ID NO: 22. The amino acid sequence of CDR1 of the 2345 light chain is SEQ ID NO: 23. The amino acid sequence of CDR1 of the 2349 light chain is SEQ ID NO: 24. The amino acid sequence of CDR2 of the 2250 light chain is SEQ ID NO: 25. The amino acid sequence of CDR2 of the 2253 light chain is SEQ ID NO: 26. The amino acid sequence of CDR2 of the 2256 light chain is SEQ ID NO: 27. The amino acid sequence of CDR2 of the 6.1.2 light chain is SEQ ID NO: 28. The amino acid sequence of CDR2 of the 6.4.1 light chain is SEQ ID NO: 29. The amino acid sequence of CDR2 of the 2345 and 2349 light chain is SEQ ID NO: 30. The amino acid sequence of CDR3 of the 2250 light chain is SEQ ID NO: 31. The amino acid sequence of CDR3 of the 2253 light chain is SEQ ID NO: 32. The amino acid sequence of CDR3 of the 2256 light chain is SEQ ID NO: 33. The amino acid sequence of CDR3 of the 6.1.2 light chain is SEQ ID NO: 34. The amino acid sequence of CDR3 of the 6.4.1 light chain is SEQ ID NO: 35. The amino acid sequence of CDR3 of the 2345 and 2349 light chain is SEQ ID NO: 36.

FIG. 11 shows amino acid sequence of CDRs of heavy and light variable chains of murine and human anti-trkC agonist monoclonal antibodies. Also shown are the families to which these sequences belong based on homology with CDR sequences available in databases.

FIG. 19 shows that NT3, but not anti-trkC agonist monoclonal antibodies, causes hyperalgesi at therapeutic doses.

FIG. 20 shows the amino acid sequence of human trkC receptor (SEQ ID NO: 56) where the boundaries of domains 4 and 5 are indicated.

FIG. 21 (in 2 pages) shows the nucleotide sequence of human trkC receptor (SEQ ID NO: 57).

FIG. 22 shows the nucleotide sequence of the heavy chain (A; SEQ ID NO: 58) and light chain (B; SEQ ID NO: 59) of the anti-trkC agonist monoclonal antibody 2250.

FIG. 23 shows the nucleotide sequence of the heavy chain (A; SEQ ID NO: 60) and light chain (B; SEQ ID NO: 61) of the anti-trkC agonist monoclonal antibody 2253.

FIG. 24 shows the nucleotide sequence of the heavy chain (A; SEQ ID NO: 62) and light chain (B; SEQ ID NO: 63) of the anti-trkC agonist monoclonal antibody 2256.

FIG. 25 shows the nucleotide sequence of the heavy chain (A; SEQ ID NO: 64) and light chain (B; SEQ ID NO: 65) of the anti-trkC agonist monoclonal antibody 2345.

FIG. 26 shows the nucleotide sequence of the heavy chain (A; SEQ ID NO: 66) and light chain (B; SEQ ID NO: 67) of the anti-trkC agonist monoclonal antibody 2349.

FIG. 27 shows the nucleotide sequence of the heavy chain (A; SEQ ID NO: 68) and light chain (B; SEQ ID NO: 69) of the anti-trkC agonist monoclonal antibody 6.1.2.

FIG. 28 shows the nucleotide sequence of the heavy chain (A; SEQ ID NO: 70) and light chain (B; SEQ ID NO: 71) of the anti-trkC agonist monoclonal antibody 6.4.1.

DETAILED DESCRIPTION OF THE PREFERRED EMBODIMENT

A. Definitions

Figure 1A:
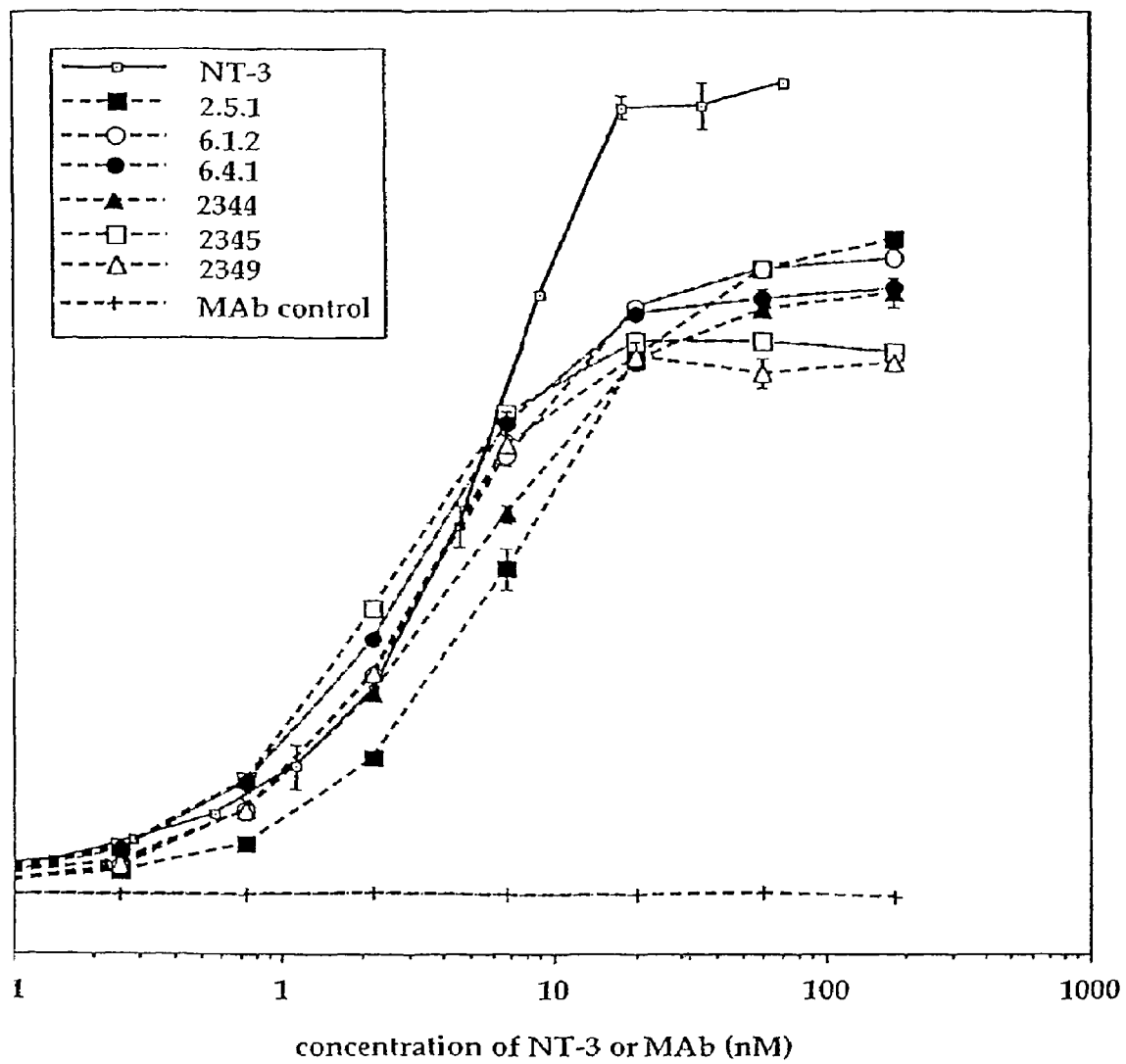
FIGS. 1A-D show agonist activity of various human (A and C) and murine (B and D) monoclonal antibodies against trkC receptor demonstrated using KIRA (A and B) and PC12 neurite outgrowth assay (C and D). Protein A purified monoclonal antibodies were diluted to 27 µg/ml in KIRA stimulation buffer (F12/DMEM 50:50 containing 2% bovine serum albumin [BSA, Intergen Co., Purchase, N.Y.) and 25 mM Hepes, 0.2 µm filtered). The monoclonal antibodies were then diluted 1:3 (8 dilutions total; concentrations ranged from 0.01-180 nM Nab) in stimulation media. GD-transfected CHO cells ($5 \times 10^4$ cells/well) were then stimulated with either NT-3 or Mab (dilutions assayed in duplicate) for 6 hours and the assay was completes as described in the examples (FIG. 1A, human Mabs.

The term "neurotrophin" and its grammatical variants are used interchangeably, and refer to a family of polypeptides comprising nerve growth factor (NGF) and sequentially related homologs. NGF, brain-derived growth factor (BDNF, a.k.a. NT-2), neurotrophin-3 (NT-3), neurotrophins-4 and -5 (NT-415), neurotrophin-6 (NT-6), and neurotrophin-7 (NT-7) have so far been identified as members of this family.

The term "neurotrophin" includes native neurotrophins of any (human or non-human) animal species, and their functional derivatives, whether purified from a native source, prepared by methods of recombinant DNA technology, or chemical synthesis, or any combination of these or other methods. "Native" or "native sequence" neurotrophins have the amino acid sequence of a neurotrophin occurring in nature in any human or non-human animal species, including naturally-occurring truncated and variant forms, and naturally-occurring allelic variants.

The terms "trk", "trk polypeptide", "trk receptor" and their grammatical variants are used interchangeably and refer to polypeptides of the receptor tyrosine kinase superfamily, which are capable of binding at least one native neurotrophin. Currently identified members of this family are trkA (p140$^{trkA}$), trkB, and trkC.

The expression "extracellular domain" or "ECD" when used herein refers to any polypeptide sequence that shares a ligand binding function of the extracellular domain of a naturally occurring receptor. Ligand binding function of the extracellular domain refers to the ability of the polypeptide to bind to a ligand. Accordingly, it is not necessary to include the entire extracellular domain since smaller segments have been found to be adequate for ligand binding. The truncated extracellular domain is generally soluble. The term ECD encompasses polypeptide sequences in which the hydrophobic transmembrane sequence (and, optionally, 1-20 amino acids C-terminal and/or N-terminal to the transmembrane domain) of the mature receptor has been deleted.

The term "agonist anti-trkC antibody" refers to an antibody, which is able to bind to and activate a native sequence trkC receptor and/or downstream pathways mediated by the trkC signaling function thereby mimicking a biological activity of a native ligand of the receptor, in particular NT-3. For example, the agonist antibody may bind to the ECD domain of a trkC receptor and thereby cause dimerization of the receptor, resulting in activation of the intracellular catalytic kinase domain. Consequently, this may result in stimulation of growth and/or differentiation of cells expressing the receptor in vitro and/or in vivo. The agonist antibodies of the present invention preferably recognize an epitope that includes at least part of domain 5 (amino acid positions from about 266 to about 381) and/or domain 4 (amino acid position from about 178 to about 265) of the human trkC receptor or a corresponding epitope on a non-human, e.g. murine trkC receptor.

"Biological activity", when used in conjunction with the agonist anti-trkC antibodies of the present invention, generally refers to having an effector function in common with NT-3, the native ligand of trkC. The effector function preferably is the ability to bind and activate the trkC receptor tyrosine kinase and/or downstream pathways mediated by the trkC signaling function. Without limitation, preferred biological activities include the ability to promote the development, proliferation, maintenance and/or regeneration of damaged cells, in particular neurons in vitro or in vivo, including peripheral (sympathetic, parasympathetic, sensory, and enteric) neurons, motorneurons, and central (brain and spinal cord) neurons, and non-neuronal cells, e.g. peripheral blood leukocytes. A particularly preferred biological activity is the ability to treat (including prevention) a neuropathy, e.g. peripheral neuropathy or other neurodegenerative disease, or repair a damaged nerve cell. The damaged neurons may be sensory, sympathetic, parasympathetic, or enteric, e.g. dorsal root ganglia neurons, motorneurons, and central neurons, e.g. neurons from the spinal cord, and the damage may be of any cause, including trauma, toxic agents, surgery, stroke, ischemia, infection, metabolic disease, nutritional deficiency, and various malignancies. Another specific biological activity is the ability to induce angiogenesis.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration of damage, such as the pathology of nerve cells, or may render the cells, e.g. neurons more susceptible to treatment by other therapeutic agents. In a preferred embodiment, the treatment reduces or slows down the decline and/or stimulates the restoration of the function of target neurons.

The "pathology" of a (chronic) neurodegenerative disease or acute nervous system injury includes all phenomena that affect the well being of the patient including, without limitation, neuronal disfunction, degeneration, injury and/or death.

The terms "neurodegenerative disease" and "neurodegenerative disorder" are used in the broadest sense to include all disorders the pathology of which involves neuronal degeneration and/or disfunction, including, without limitation, peripheral neuropathies; motorneuron disorders, such as amylotrophic lateral schlerosis (ALS, Lou Gehrig's disease), Bell's palsy, and various conditions involving spinal muscular atrophy or paralysis; and other human neurodegenerative diseases, such as Alzheimer's disease, Parkinson's disease, epilepsy, multiple schlerosis, Huntington's chorea, Down's Syndrome, nerve deafness, and Meniere's disease.

"Peripheral neuropathy" is a neurodegenerative disorder that affects the peripheral nerves, most often manifested as one or a combination of motor, sensory, sensorimotor, or autonomic dysfunction. Peripheral neuropathies may, for example, be genetically acquired, can result from a systemic disease, or can be induced by a toxic agent, such as a neurotoxic drug, e.g. antineoplastic agent, or industrial or environmental pollutant. "Peripheral sensory neuropathy" is characterized by the degeneration of peripheral sensory neurons, which may be idiopathic, may occur, for example, as a consequence of diabetes (diabetic neuropathy), cytostatic drug therapy in cancer (e.g. treatment with chemotherapeutic agents such as vincristine, cisplatin, methotrexate, 3'-azido-3'-deoxythymidine, or taxanes, e.g. paclitaxel [TAXOL®, Bristol-Myers Squibb Oncology, Princeton, N.J.] and doxetaxel [TAXOTERE®, Rhône-Poulenc Rorer, Antony, France]), alcoholism, acquired immunodeficiency syndrom (AIDS), or genetic predisposition. Genetically acquired peripheral neuropathies include, for example, Refsum's disease, Krabbe's disease, Metachromatic leukodystrophy, Fabry's disease, Dejerine-Sottas syndrome, Abetalipoproteinemia, and Charcot-Marie-Tooth (CMT) Disease (also known as Proneal Muscular Atrophy or Hereditary Motor Sensory Neuropathy (HMSN)). Most types of peripheral neuropathy develop slowly, over the course of several months or years. In clinical practice such neuropathies are called chronic. Sometimes a peripheral neuropathy develops rapidly, over the course of a few days, and is referred to as acute. Peripheral neuropathy usually affects sensory and motor nerves together so as to cause a mixed sensory and motor neuropathy, but pure sensory and pure motor neuropathy are also known.

The term "toxic agent", as used in the context of the present invention, is meant to refer to a substance that, through its chemical action, injures, impairs, or inhibits the activity of a component of the nervous system. The long list of toxic agents (also referred to as "neurotoxic agents") includes, without limitation, chemotherapeutic agents, such as those listed above, alcohol, metals, industrial toxins, contaminants of food and medicines, etc.

"Mammal" for purpose of treatment refers to any animal classified as a mammal, including humans, domestic and farm animals, and zoo, sport or pet animals, such as dogs, horses, sheep, cats, cows, etc. Preferably, the mammal is human.

The term "trkC immunoadhesin" is used interchangeably with the expression "trkC-immunoglobulin chimera" and refers to a chimeric molecule that combines a portion of trkC (generally the extracellular domain thereof) with an immunoglobulin sequence. The immunoglobulin sequence preferably, but not necessarily, is an immunoglobulin constant domain. Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl. Acad. Sci. USA,* 84: 2936-2940 [1987]); CD4* (Capon et al., *Nature* 337: 525-531 [1989]; Traunecker et al., *Nature,* 339: 68-70 [1989]; Zettmeissl et al., *DNA Cell Biol.* 9: 347-353 [1990]; Byrn et al., *Nature,* 344: 667-670 [1990]); L-selectin (homing receptor) (Watson et al., *J. Cell. Biol.,* 110:2221-2229 [1990]; Watson et al., *Nature,* 349: 164-167 [1991]); CD44* (Aruffo et al., *Cell,* 61: 1303-1313 [1990]; CD28* and B7* (Linsley et al., *J. Exp. Med.,* 173: 721-730 [1991]); CTLA-4* (Lisley et al., *J. Exp. Med.* 174: 561-569 [1991]; CD22* (Stamenkovic et al., *Cell,* 66:1133-11144 [1991]); TNF receptor (Ashkenazi et al., *Proc. Natl. Acad. Sci. USA,* 88: 10535-10539 [1991]; Lesslauer et al., *Eur. J. Immunol,* 27:2883-2886 [1991]; Peppel et al., *J. Exp. Med.,* 174:1483-1489 [1991]); NP receptors (Bennett et al., *J. Biol. Chem.* 266:23060-23067 [1991]); and IgE receptor α* (Ridgway et al., *J. Cell. Biol.,* 115:abstr. 1448 [1991]), where the asterisk (*) indicates that the receptor is member of the immunoglobulin superfamily.

"Isolated" nucleic acid or polypeptide in the context of the present invention is a nucleic acid or polypeptide that is identified and separated from contaminant nucleic acids or polypeptides present in the animal or human source of the nucleic acid or polypeptide. The nucleic acid or polypeptide may be labeled for diagnostic or probe purposes, using a label as described and defined further below in discussion of diagnostic assays.

In general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

In the context of the present invention the expressions "cell", "cell line", and "cell culture" are used interchangeably, and all such designations include progeny. Thus, the words "transformants" and "transformed (host) cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

An "exogenous" element is defined herein to mean nucleic acid sequence that is foreign to the cell, or homologous to the cell but in a position within the host cell nucleic acid in which the element is ordinarily not found.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a -sheet configuration, connected by three hypervariable regions, which form loops connecting, and in some cases forming part of, the -sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain: Chothia and Lesk *J. Mol. Biol.* 196: 901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa ( ) and lambda ( ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called , , , , and , respectively. The subunit structures and three-dimensional configurations of different classes of immunoglobulins are well known.

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

The term "epitope" is used to refer to binding sites for (monoclonal or polyclonal) antibodies on protein antigens.

Antibodies which bind to domain 5 and/or 4 within the amino acid sequence of native sequence human trkC, or to an equivalent epitope in a native sequence non-human trkC receptor, are identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. A competition ELISA assay is specifically described in Example 1. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels. A competition ELISA assay is disclosed in Example 1.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., Molecular Biology of the Cell, Garland Publishing, Inc., New York (3d ed. 1994)).

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50 C, or (2) employing during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C. Another example is use of 50% formamide, 5×SSC (0.75 M NaCl, 0.075 M sodium citrate), 50 mM sodium phosphate (pH 618), 0.1% sodium pyrophosphate, 5× Denhardt's solution, sonicated salmon sperm DNA (50 g/ml), 0.1% SDS, and 10% dextran sulfate at 42 C, with washes at 42 C in 0.2×SSC and 0.1% SDS.

B. Methods for Carrying Out the Invention

The present invention concerns agonist human and non-human monoclonal antibodies (including humanized forms of the latter), which mimick certain biological properties of NT-3, the native ligand of the trkC receptor. General techniques for the production of murine and human anti-trkC antibodies are well known in the art and are described hereinbelow. Further details, including the selection of agonist antibodies, are provided in Example 1.

1. Antibody Preparation (i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

(ii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59-103, [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), conditions under which the growth of HGPRT-deficient cells is prevented.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp.51-63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp.59-103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-trk monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an trk receptor and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Recombinant production of antibodies will be described in more detail below.

(iii) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239: 1534-1536 (1988)], by substituting rodent CDRs or CDR sequences for the corresponding sequences of a human antibody.

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 August 192, which is a continuation-in-part of application Ser. No. 07/715,272 filed 14 Jun. 1991.

(iv) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications,* pp.51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993), and the isolation of a high affinity human antibody directly from such large phage library is reported by Griffith et al., *EMBO J.* (1994), in press. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

(v) Bispecific Antibodies

Bispecific antibodies are monoclonal, preferably human or humanized, antibodies that have binding specificities for at least two different antigens. In the present case, one of the binding specificities is for the trkC receptor to provide an agonist antibody, the other one is for any other antigen, and preferably for another receptor or receptor subunit. For example, bispecific antibodies specifically binding a trkC receptor and a neurotrophin, or a trkC receptor and another trk receptor are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., *Methods in Enzymology* 121, 210 (1986).

(vi) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(vii) Antibody Fragments

In certain embodiments, the anti-trkC antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from E. coli and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

(viii) Amino Acid Sequence Variants of Antibodies

Amino acid sequence variants of the anti-trkC antibodies are prepared by introducing appropriate nucleotide changes into the anti-trkC antibody DNA, or by peptide synthesis. Such variants include, for example, deletions from, and/or insertions into and/or substitutions of, residues within the amino acid sequences of the anti-trkC antibodies of the examples herein. Any combination of deletion, insertion, and substitution is made to arrive at the final construct, provided that the final construct possesses the desired characteristics. The amino acid changes also may alter post-translational processes of the humanized or variant anti-trkC antibody, such as changing the number or position of glycosylation sites.

A useful method for identification of certain residues or regions of the anti-trkC antibody that are preferred locations for mutagenesis is called "alanine scanning mutagenesis," as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with trkC antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-trkC antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-trkC antibody with an N-terminal methionyl residue or the antibody fused to an epitope tag. Other insertional variants of the anti-trkC antibody molecule include the fusion to the N- or C-terminus of the anti-trkC antibody of an enzyme or a polypeptide which increases the serum half-life of the antibody (see below).

Another type of variant is an amino acid substitution variant. These variants have at least one amino acid residue in the anti-trkC antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized or variant anti-trkC antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human trkC. Such contact residues and neighboring residues are candidates for substitution according to the techniques elaborated herein. Once such variants are generated, the panel of variants is subjected to screening as described herein and antibodies with superior properties in one or more relevant assays may be selected for further development.

(ix) Glycosylation Variants of Antibodies

Antibodies are glycosylated at conserved positions in their constant regions (Jefferis and Lund, Chem. Immunol. 65:111-128 [1997]; Wright and Morrison, TibTECH 15:26-32 [1997]). The oligosaccharide side chains of the immunoglobulins affect the protein's function (Boyd et al., Mol. Immunol. 32:1311-1318 [1996]; Wittwe and Howard, Biochem. 29:4175-4180 [1990]), and the intramolecular interaction between portions of the glycoprotein which can affect the conformation and presented three-dimensional surface of the glycoprotein (Hefferis and Lund, supra; Wyss and Wagner, Current Opin. Biotech. 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., Nature Med. 1:237-243 [1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., Mol. Immunol. 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180 [1999]).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc. Glycosylation variants may, for example, be prepared by removing, changing and/or adding one or more glycosylation sites in the nucleic acid sequence encoding the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-trkC antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-trkC antibody.

The glycosylation (including glycosylation pattern) of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., J. Biol. Chem. 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510, 261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

(x) Other Modifications of Antibodies

The anti-trkC antibodies disclosed herein may also be formulated as immunoliposomes. Liposomes containing the antibody are prepared by methods known in the art, such as described in Epstein et al., Proc. Natl. Aced Sci. USA 82:3688 (1985); Hwang et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:

286-288 (1982) via a disulfide interchange reaction. A chemotherapeutic agent (such as Doxorubicin) is optionally contained within the liposome. See Gabizon et al., *J. National Cancer Inst.* 81(19):1484 (1989).

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as -galactosidase and neuraminidase useful for converting glycosylated prodrugs into free drugs; -lactamase useful for converting drugs derivatized with -lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-trkC antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 [1984]).

In certain embodiments of the invention, it may be desirable to use an antibody fragment, rather than an intact antibody. In this case, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the CL region or $V_L$ region, or both, of the antibody fragment.

Covalent modifications of the humanized or variant anti-trkC antibody (including glycosylation variants) are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

2. Vectors, Host Cells and Recombinant Methods

The invention also provides isolated nucleic acid encoding the non-human, e.g. murine and human anti-trkC antibodies of the present invention (including the humanized versions of the non-human antibodies), vectors and host cells comprising the nucleic acid, and recombinant techniques for the production of the antibodies.

For recombinant production of an antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Sarratia, e.g., *Serratia marcescans*, and Shigella, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-trkC antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*,

*K. fragilis* (ATCC 12,424), *K. bulgaricus* (ATCC 16,045) *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antitrkC antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol* 36:59 [1977]); baby hamster kidney cells (BHK, ATCC CCL 10); Chinese hamster ovary cells/-DHFR (CHO, Urlaub et al., *Proc. Natl. Acad. Sci. USA* 77:4216 [1980]); mouse sertoli cells (TM4, Mather, *Biol. Reprod.* 23:243-251 [1980]); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 [1982]); MRC 5 cells; and FS4 cells.

Host cells are transformed with the above-described expression or cloning vectors for anti-trkC antibody production and cultured in conventional nutrient media modified as appropriate for inducing promoters, selecting transformants, or amplifying the genes encoding the desired sequences.

The host cells used to produce the anti-trkC antibody of this invention may be cultured in a variety of media. Commercially available media such as Ham's F10 (Sigma), Minimal Essential Medium ((MEM) (Sigma), RPMI-1640 (Sigma), and Dulbecco's Modified Eagle's Medium (DMEM) (Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human 1, 2, or 4 heavy chains (Lindmark et al., *J. Immunol Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

3. Identification of Agonist Anti-trkC Antibodies

Agonist antibodies may be identified, for example, using the kinase receptor activation (KIRA) assay described in U.S. Pat. Nos. 5,766,863 and 5,891,650. This ELISA-type assay is suitable for qualitative or quantitative measurement of kinase activation by measuring the autophosphorylation of the kinase domain of a receptor protein tyrosine kinase (rPTK, e.g. trk receptor), as well as for identification and characterization of potential agonist or antagonists of a selected rPTK. The first stage of the assay involves phosphorylation of the kinase domain of a kinase receptor, in the present case a trkC receptor, wherein the receptor is present in the cell membrane of a eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate agonist, is then added to the wells having the adherent cells, such that the tyrosine kinase receptor (e.g. trkC receptor) is exposed to (or contacted with) the analyte. This assay enables identification of agonist ligands for the tyrosine kinase receptor of interest (e.g. trkC). It is also possible to use this assay to detect antagonists of a tyrosine kinase receptor. In order to detect the presence of an antagonist ligand which blocks binding of an agonist to the receptor, the adhering cells are exposed to the suspected antagonist ligand first, and then to the agonist ligand, so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands. Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

Following initial identification, the agonist activity can be further confirmed and refined by bioassays, known to test the targeted biological activities. For example, the ability of anti-trkC monoclonal antibodies to mimic the activity of NT-3 can be tested in the PC12 neurite outgrowth assay as described in Example 1, and confirmed in known animal models of neurodegenerative diseases, such as the experimental animal models of cisplatin- and pyridoxine-induced neuropathies described in Example 2.

3. Therapeutic and Diagnostic Uses of Agonist Anti-TrkC Antibodies

The anti-trkC agonist antibodies of the present invention are believed to be useful in the treatment (including prevention) of disorders the pathology of which involves cellular degeneration or disfunction. In particular, the anti-trkC agonist antibodies are promising candidates for the treatment of various (chronic) neurodegenerative disorders and acute nerve cell injuries. Such neurodegenerative disorders include, without limitation, peripheral neuropathies; motorneuron disorders, such as amylotrophic lateral schlerosis (ALS, Lou Gehrig's disease), Bell's palsy, and various conditions involving spinal muscular atrophy or paralysis; and other human neurodegenerative diseases, such as Alzheimer's disease, Parkinson's disease, epilepsy, multiple schlerosis, Huntington's chorea, Down's Syndrome, nerve deafness, and Meniere's disease, and acute nerve cell injuries, for example due to trauma or spinal cord injury.

The anti-trkC antibodies of the present invention are believed to be particularly suited for the treatment of peripheral neuropathy, a neurodegenerative disorder that affects the peripheral nerves, most often manifested as one or a combination of motor, sensory, sensorimotor, or autonomic dysfunction. Peripheral neuropathies may, for example, be genetically acquired, can result from a systemic disease, can be induced by a toxic agent, such as a neurotoxic drug, e.g. antineoplastic agent, or industrial or environmental pollutant, or can be idiopathic. Thus, peripheral sensory neuropathy is characterized by the degeneration, decrease or failure of function of peripheral sensory neurons, which may occur, for example, as a consequence of diabetes (diabetic neuropathy), cytostatic drug therapy in cancer (e.g. treatment with chemotherapeutic agents such as vincristine, cisplatin, methotrexate, or 3'-azido-3'-deoxythymidine), alcoholism, acquired immunodeficiency syndrome (AIDS), or genetic predisposition. Genetically acquired peripheral neuropathies include, for example, Refsum's disease, Krabbe's disease, Metachromatic leukodystrophy, Fabry's disease, Dejerine-Sottas syndrome, Abetalipoproteinemia, and Charcot-Marie-Tooth (CMT) Disease (also known as Proneal Muscular Atrophy or Hereditary Motor Sensory Neuropathy (HMSN)).

Based on the demonstrated ability of NT-3, the native ligand of the trkC receptor, to promote proliferation of peripheral blood leukocytes, the anti-trkC agonist antibodies of the present invention may be used also as therapeutic agents for the treatment of neutropenia, various infections, and tumors. Since the expression of trkC is not limited to neurons, anti-trkC agonist antibodies are expected to find utility in the prevention or treatment of disorders characterized by cellular degeneration in general, without restriction to neural cells.

The anti-trkC antibodies of the present invention may also be used to induce angiogenesis, or treat pathological conditions/diseases in which the induction of angiogenesis is desirable. Such pathological conditions include, for example, cardiac ischemia regardless of the underlying pathology, including cerebrovascular disorders caused by insufficient cerebral circulation. Angiogenesis may also be desirable in the treatment of wounds, including ulcers, diabetic complications of sickle cell disease, and post surgical wounds.

The anti-trkC antibodies of the present invention may also be useful in the diagnosis of diseases involving cellular degeneration, in particular the neurodegenerative diseases listed above.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^3H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) -D-galactosidase (-D-Gal) with a chromogenic substrate (e.g., p-nitrophenyl- -D-galactosidase) or fluorogenic substrate 4-methylumbelliferyl- -D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-trkC antibody need not be labeled, and the presence thereof can be detected using a labeled antibody which binds to the anti-trkC antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp.147-158 (CRC Press, Inc. 1987).

Competitive binding assays rely on the ability of a labeled standard to compete with the test sample analyte for binding with a limited amount of antibody. The amount of trkC protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies may also be used for in vivo diagnostic assays. Generally, the antibody is labeled with a radionuclide (such as $^{111}In$, $^{99}Tc$, $^{14}C$, $^{131}I$, $^{125}I$, $^3H$, $^{32}P$ or $^{35}S$) so that the cells or tissue of interest can be localized using immunoscintiography.

The antibodies may also be used as staining reagents in pathology, following techniques well known in the art.

The anti-trkC agonist antibodies of the present invention are believed to possess numerous advantages over NT-3 as therapeutic agents, including improved efficacy, improved pharmacokinetic properties (pK) and bioavailability, and lack of hyperalgesia following administration.

4. Pharmaceutical Formulations

Therapeutic formulations of the antibodies of the present invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

An effective amount of an antibody of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 g/kg to up to 100 mg/kg or more, depending on the factors mentioned above. Typically, the clinician will administer a molecule of the present invention until a dosage is reached that provides the required biological effect. The progress of this therapy is easily monitored by conventional assays.

Administration may be by any conventional route known in the art including, without limitation, intravenous, subcutaneous, topical, intramuscular, intratracheal, intracerebral, intranasal, intrapulmonary, and intraparyncal administration.

4. Gene Therapy

The nucleic acid encoding the antibodies of the present invention may also be used in gene therapy of various (chronic) neurodegenerative disorders and acute nerve cell injuries, especially genetically acquired peripheral neuropathies. Two basic approaches to gene therapy have evolved: ex viva gene therapy and in viva gene therapy. In ex vivo gene therapy, cells are removed from a subject and cultured in vitro. A functional replacement gene is introduced into the cells in vitro, the modified cells are expanded in culture, and then reimplanted in the subject. In in vivo gene therapy, the target cells are not removed from the subject. Rather, the transferred gene is introduced into cells of the recipient in situ, that is, within the recipient.

Several ex vivo gene therapy studies in humans have been reported and are reviewed, for example, in Anderson, *Science* 256:808-813 (1992), and Miller, *Nature* 357:455-460 (1992).

The viability of in viva gene therapy has been demonstrated in several animal models, as reviewed in Felgner et al., *Nature* 349:351-352 (1991). Direct gene transfer has been reported, for example, into muscle tissue (Ferry et al., *Proc Natl. Acad. Sci.* 88:8377-8781 [1991]; Quantin et al., *Proc. Natl. Acad. Sci. USA* 89:2581-2584 [1992]); the arterial wall (Nabel et al., *Science* 244:1342-1344 [1989]); and the nervous system (Price et al., *Proc. Natl. Acad. Sci.* 84:156-160 [1987]).

Accordingly, the present invention also provides delivery vehicles suitable for delivery of a polynucleotide encoding an agonist anti-trkC antibody into cells (whether in vivo or ex vivo). Generally, a polynucleotide encoding an antibody (e.g. linear antibody or antibody chains) will be operably linked to a promoter and a heterologous polynucleotide. Delivery vehicles suitable for incorporation of a polynucleotide encoding an antibody of the present invention for introduction into a host cell include non-viral vehicles and viral vectors. Verma and Somia, *Nature* 389:239-242 (1997).

A wide variety of non-viral vehicles for delivery of a polynucleotide encoding an antibody of the present invention are known in the art and are encompassed in the present invention. A polynucleotide encoding an anti-trkC antibody can be delivered to a cell as naked DNA (U.S. Pat. No. 5,692,622; WO 97/40163). Alternatively, a polynucleotide encoding an anti-trkC antibody herein can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide encoding an antibody herein can be associated non-covalently or covalently with these various forms of delivery. Liposomes can be targeted to a particular cell type, e.g., to a glomerular epithelial cell.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al., *Science* 272:263-267 (1996).

Non-viral delivery vehicles comprising a polynucleotide encoding an anti-trkC antibody can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman, *Nature Biotechnol.* 14:339-342 [1996]); or lamellar liposomes (Wilson et al. *Proc. Natl. Acad. Sci. USA* 74:3471 [1977]; and Faller et al *J. Virol.* 49:269 [1984]).

In a preferred embodiment, nucleic acid encoding both the heavy and the light chains (including fragments) of an anti-trkC antibody of the present invention will be present in the same polycistronic expression vector, such as those disclosed in U.S. Pat. Nos. 4,965,196 and 4,713,339. Polycistronic expression vectors contain sequences coding for a secondary protein and a desired protein, wherein both the desired and secondary sequences are governed by the same promoter. The coding sequences are separated by translational stop and start signal codons. The expression of the secondary sequence effects control over the expression of the sequence for the desired protein, and the secondary protein functions as a marker for selection of transfected cells.

In in vivo gene therapy, the vector may be administered to the recipient, for example, by intravenous (i.v.) injection. Suitable titers will depend on a variety of factors, such as the particular vector chosen, the host, strength of promoter used, and the severity of the disease being treated.

The invention will be further illustrated by the following non-limiting examples.

EXAMPLES

Example 1

Production and Characterization of Agonist Anti-trkC Monoclonal Antibodies

Production and Isotyping of Antibodies

Wild type Balb/C mice and transgenic mice producing human IgG2 or IgG4 (Xenomice, described in Mendez et al., *Nature Genetics* 15: 146-156 [1997]) were hyperimmunized either intraperitoneally, via rear footpad, or subcutaneously with 20 μg of human trkC-IgG (Shelton et al., *J. Neurosci.* 15: 477-491 [1995]) in either Frieund's or Ribi adjuvant as described in Mendez et al. (supra). Spleen cells from the immune mice were fused with myeloma cells (X63.Ag8.653, ATCC Rockville, Md.). A total of 33 fusions were performed using 253 Xenomice and 35 wild type Balb/C mice. Plates (21,734 wells total) were initially screened by direct ELISA using trkC-IgG. The ELISA screen identified 684 trkC positive hybridomas, all of which were then evaluated for agonist activity in trkC KIRA (Kinase activated Receptor Assay). The KIRA identified 14 Xenomouse derived and 22 wild type Balb/C mice derived hybridomas secreting anti-trkC agonist antibodies. These hybridomas were subcloned by limiting dilution, reassayed to confirm agonist activity, and were used to induce ascites by injecting into Pristane-primed Balb/C or nude mice (Hongo et al., *Hybridoma* 14: 253-260 [1995]). The monoclonal antibodies present in ascites were purified by Protein A affinity chromatography (Hongo et al., supra). Specific fusion efficiency (number of positives/number of wells screened) was 3% for both the Xenomouse and wild type Balb/C mouse fusions. The incidence of agonist monoclonal antibodies (agonists/number of trkC ELISA positives) was 3% and 8% for the Xenomouse and wild type Balb/C mouse fusions, respectively. Isotypes of the murine monoclonal antibodies were determined using either GIBCO BRL dipstick or Zymed mouse-typer isotyping kit, following supplier's instructions. The Xenomice were either $IgG_2$ or $IgG_4$ strain, producing corresponding isotypes of antibodies. Table 1 shows isotypes of various human and murine anti-trkC monoclonal antibodies. A total of 8 human $IgG_2$, 6 human $IgG_4$, 7 murine $IgG_1$, 10 murine $IgG_2$, and 5 murine $IgG_{2b}$ monoclonal antibodies were identified. The monoclonal antibodies with the most potent agonist activity (depicted by asterisk in Table 2), as determined by KIRA assay, were selected for in-depth characterization.

TABLE 2

| Human Mabs (14 Total) | |
|---|---|
| $IgG_2$ Isotype (8 Mabs) | $IgG_4$ Isotype (6 Mabs) |
| 2.5.1* | 4.8 |
| 6.1.2* | 2337 |
| 6.4.1* | 2338 |
| 2342 | 2339 |
| 2343 | 2348 |
| 2344* | 2349* |
| 2345* | |
| 2346 | |

| Murine Mabs (22 Total) | | | |
|---|---|---|---|
| $IgG_1$ (7) | $IgG_{2a}$ (10) | $IgG_{2b}$ (5) | $IgG_3$ |
| 2249 | 2248* | 2252 | |
| 2250* | 2272 | 2273 | |
| 2253* | 2251 | 2277 | |
| 2254 | 2255 | 2279 | |
| 2256* | 2274 | 2280 | |
| 2257 | 2275 | | |
| 2260 | 2276 | | |
| | 2278 | | |
| | 2281 | | |
| | 2282 | | |

Determination of Agonist Activity a. KIRA Assay

Figure 1B:
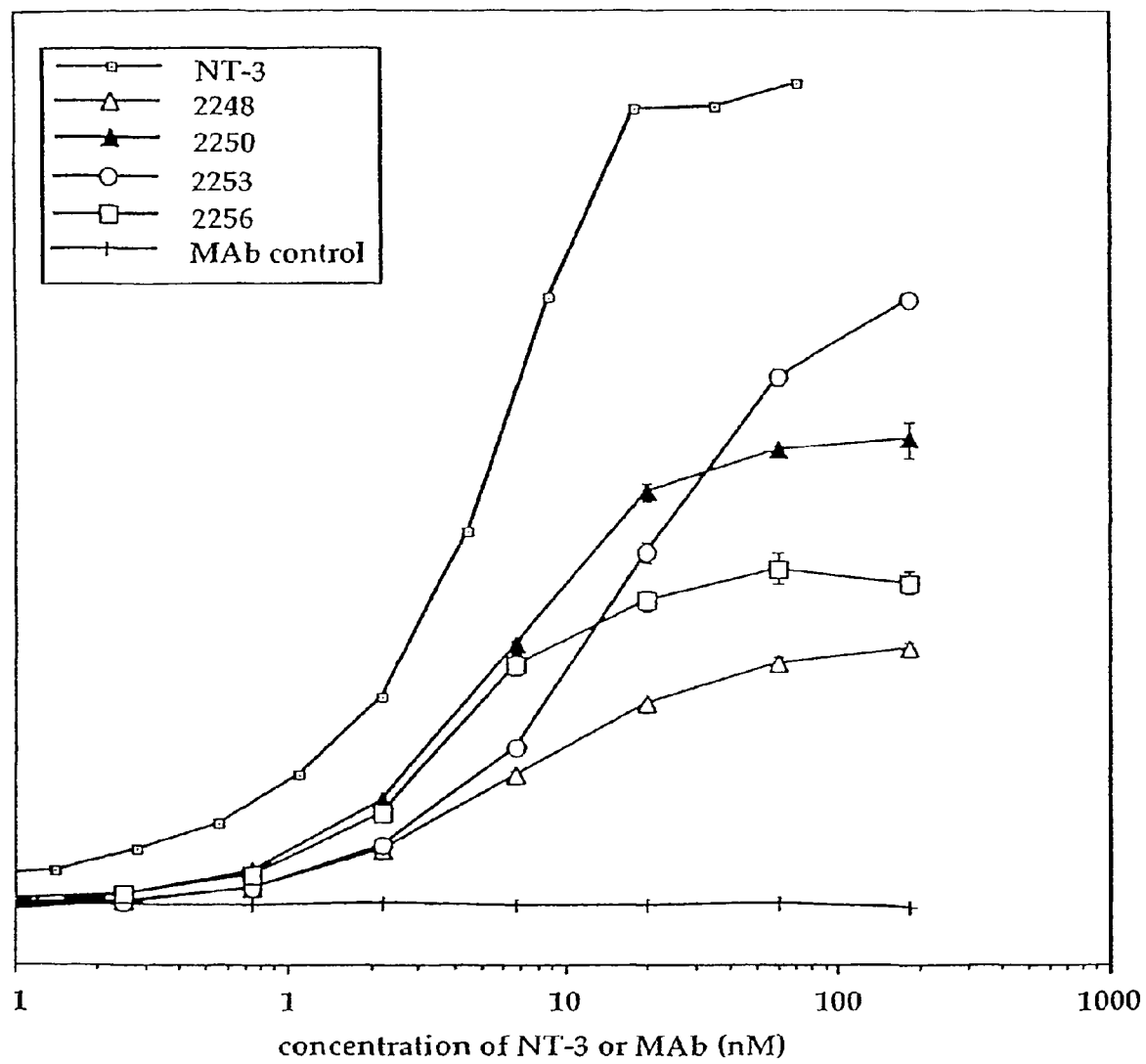

Two bioassays were used to determine NT-3 agonist activity of anti-trkC monoclonal antibodies. The Kinase activated receptor assay (KIRA), which has been discussed in greater detail hereinabove, measures tyrosine phosphorylation of trkC in transfected cells in response to stimulation with a ligand, such as NT-3, or agonist monoclonal antibodies (Sadick et al., *Exp. Cell Res.* 234: 354-361 [1997]). The monoclonal antibodies were diluted to 27 μg/ml in KIRA stimulation buffer (F12/DMEM 50:50 containing 2% bovine serum albumin (BSA; Intergen Co., Purchase, N.Y.) and 25 mM Hepes, 0.2 μm filtered). The monoclonal antibodies were further diluted serially 1:3 (8 dilutions total; concentrations ranging from 0.01-180 nM) in stimulation medium. Chinese Hamster Ovary (CHO) cells stably transfected with trkC fused with a 26 amino acid polypeptide flag epitope derived from HSV glycoprotein D (gD) were seeded (5×10$^4$ cells/well) and grown in 96-well cell culture plates. The cells were then stimulated with either NT-3 (as a positive control) or various anti-trkC monoclonal antibodies, using serial dilutions of 0.1; 1.56; 3.13; 6.25; 12.5; 25; 50 and 100 ng/ml. All dilutions were assayed in duplicate for 6 hours. The assay was carried out essentially as described in Sadick et al. (supra). Briefly, cells were lysed using Triton X-100 and trkC present in lysate captured in ELISA using antibodies against the gD epitope and phosphorylated trkC detected and quantitated using anti-phosphotyrosine antibodies suitably conjugated with enzyme. A monoclonal antibody not directed against trkC (anti-IL8 IgG$_2$ Xenomous-derived human antibody or anti-gp120 IgG$_1$ murine monoclonal antibody) was used as a negative control. As shown in FIG. 1 (A and B), all the selected anti-trkC monoclonal antibodies could mimic the activity of NT-3 inasmuch as they could stimulate tyrosine phosphorylation of trkC receptor. The human anti-trkC monoclonal antibodies (FIG. 1A) showed more potent agonistic activity than the murine anti-trkC monoclonal antibodies (FIG. 1B). For example, the best human anti-trkC monoclonal antibody is 10-fold more potent than the best murine anti-trkC monoclonal antibody. Furthermore, the human monoclonals were nearly as efficient as NT-3 especially in the lower range of concentration.

b. PC12 Neurite Outgrowth Assay

Figure 1C:
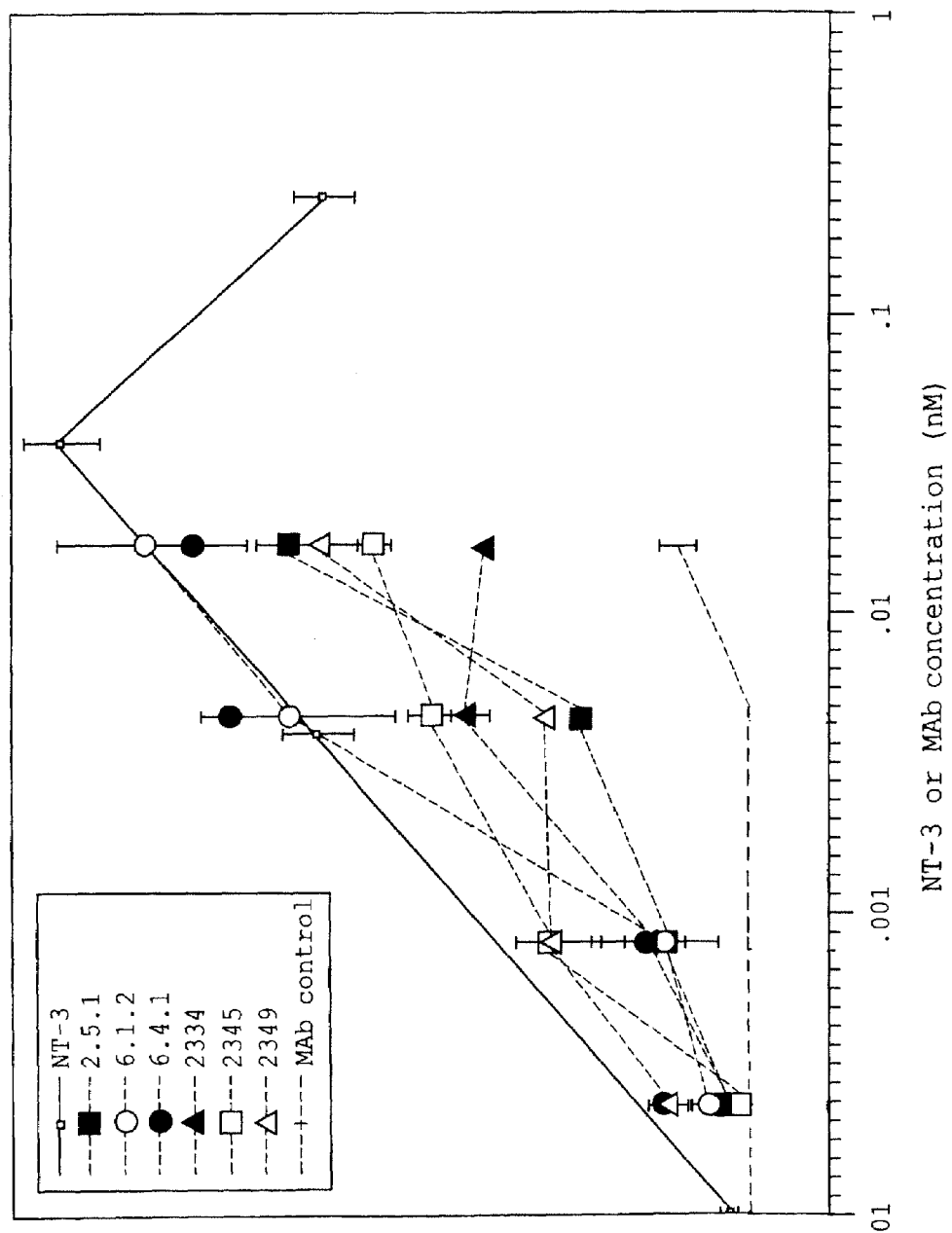
Figure 1D:
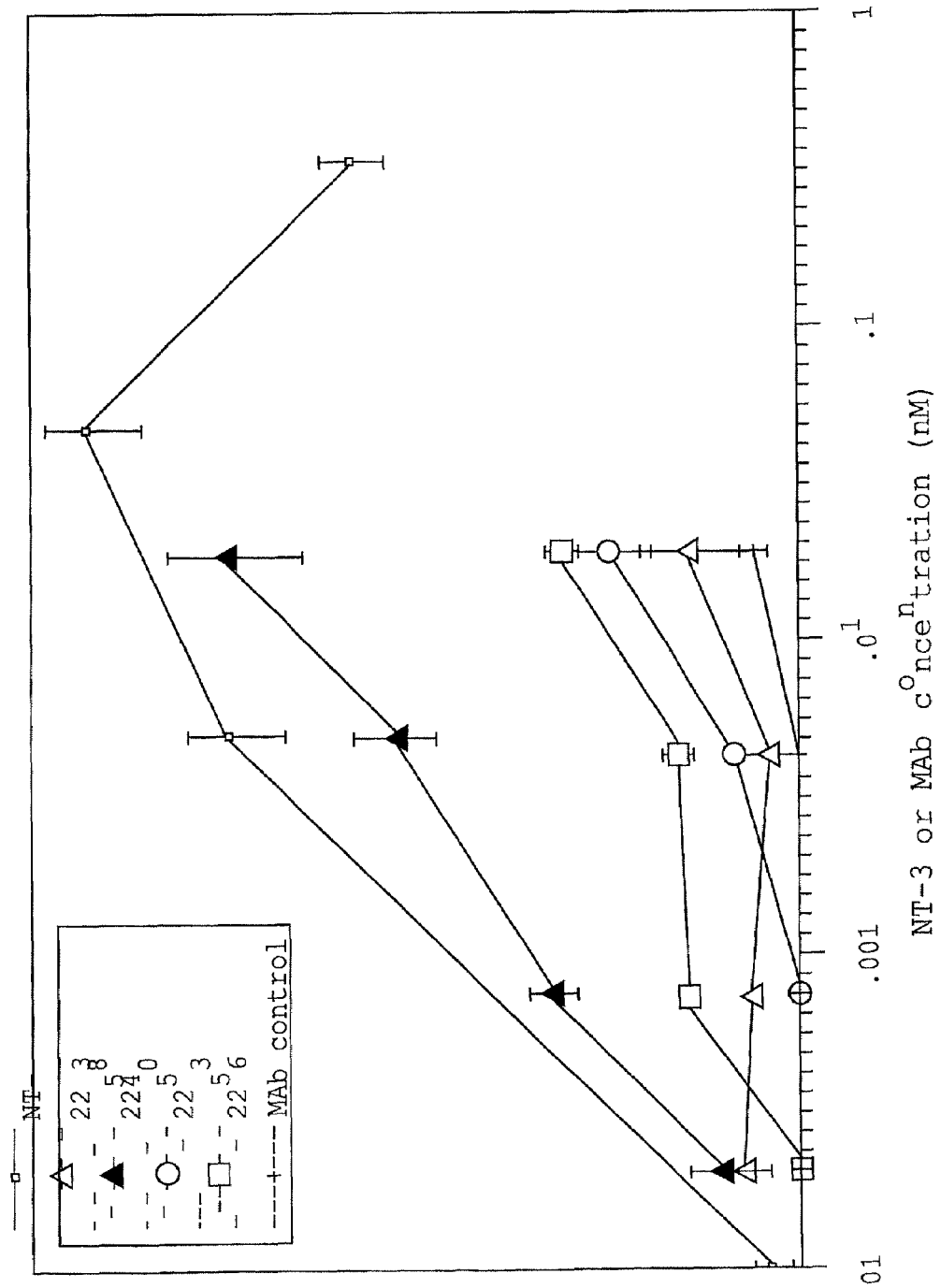

Another assay used to determine NT-3 mimetic activity of anti-trkC monoclonal antibodies was PC12 neurite outgrowth assay. This assay measures the outgrowth of neurite processes by rat pheocytochroma cells (PC12) in response to stimulation by appropriate ligands. These cells express endogenous trkA and are therefore responsive to NGF. However, they do not express endogenous trkC and are therefore transfected with trkC expression construct in order to elicit response to NT-3 and its agonists. PC12 cells were transfected (Urfer et al., Biochem. 36:4775-4781 [1997]; Tsoulfas et al., Neuron 10:975-990 [1993]) with full-length human trkC and plated in 96-well cell culture plates (1000 cells/well). Three days following transfection, anti-trkC monoclonal antibodies were added in triplicate (concentration ranging from 0.0002 to 2.7 nM) and incubated for an additional 3 days at 37° C. The cells were then analyzed by phase contrast microscopy and cells with neurites exceeding 2 times the diameter of the cell were counted. The human as well as the murine anti-trkC monoclonal antibodies could stimulate neurite outgrowth in PC12 cells as shown in FIGS. 1C and D. The human anti-trkC monoclonal antibodies (FIG. 1C) exhibited far more potent activity than the murine anti-trkC monoclonal antibodies (FIG. 1D) thus corroborating the results obtained in the KIRA assay. Furthermore, consistent with the KIRA assay results, the human anti-trkC monoclonal antibodies showed roughly similar stimulation as obtained with NT-3. The results obtained with the two bioassays described above demonstrate the ability of anti-trkC monoclonal antibodies to mimic the activity of NT-3, the natural ligand of trkC receptor.

Agonist activity of the monoclonal antibodies was ranked according to maximum induction of tyrosine phosphorylation and calculated EC50 of the phosphorylation curves in the KIRA assay and PC12 neurite outgrowth assay. Table 3 summarizes characteristics of various anti-trkC agonist monoclonal antibodies.

TABLE 3

| MAb ID | Isotype | Agonist Activity KIRA/PC12 | Binds Rat trkC | Immunoblot NR | Immunoblot Red. | Affinity Kd (nM) |
|---|---|---|---|---|---|---|
| Human MAbs | | | | | | |
| 2.5.1 | G2 | (+++/+++) | NO | ++ | ++ | 12 |
| 6.1.2 | G2 | (++++/++++) | NO | + | + | 12.5 |
| 6.4.1 | G2 | (++++/++++) | YES | + | + | 12 |
| 2344 | G2 | (+++/+++) | NO | ++ | + | 19 |
| 2345 | G2 | (++++/++++) | NO | ++ | ++ | 12.1 |
| 2349 | G4 | (++++/++++) | NO | ++ | + | 23 |
| Murine MAbs | | | | | | |
| 2248 | G2a | (+/+) | NO | +++ | − | 5.9 |
| 2250 | G1 | (++/++) | NO | ++ | ++ | 8.7 |
| 2253 | G1 | (++/+) | NO | ++ | ++ | 42 |
| 2256 | G1 | (+/+) | YES | ++ | + | 62 |

Testing Specificity of Anti-trkC Antibodies

The specificity of anti-trkC monoclonal antibodies was tested using direct ELISA. The microtiter plates were coated overnight with immunoadhesin construct of the receptor trkA-IgG, trkB-IgG or trkC-IgG as capture antigens (described in Shelton et al., J. Neurosci. 15: 477-491 [1995]) using 100 μl of 1 μg/ml solution diluted in 50 mM carbonate buffer, pH 9.5. CD4-IgG (Capon et al., Nature 337: 525-531 [1989]) was used in place of capture antigen as a negative control. The coated plates were incubated for 1 hr at room temperature with various concentration of anti-trkC monoclonal antibodies (100 μl of 0.01 to 1 μg/ml) diluted in PBS containing 0.5% BSA and 0.05% Tween 20. After washing to remove excess unbound antibodies, appropriate HRP conjugate (human monoclonal antibodies: goat anti-human K-HRP, 1:5000 diluted; murine monoclonal antibodies: goat anti-mouse IgG (Fc)-HRP, 1:5000 diluted) was added and incubated for 1 hr at room temperature. The plates were then washed, developed and read as previously described (Hongo et al., Hybridoma 14: 253-260 [1995]). FIG. 2 shows a representative example using a human anti-trkC monoclonal antibody 6.1.2. The binding was highly specific to trkC, and no significant cross-reaction was observed with either trkA or trkB. Similarly, other human and mouse anti-trkC monoclonal antibodies showed specific recognition of trkC.

Figure 3:
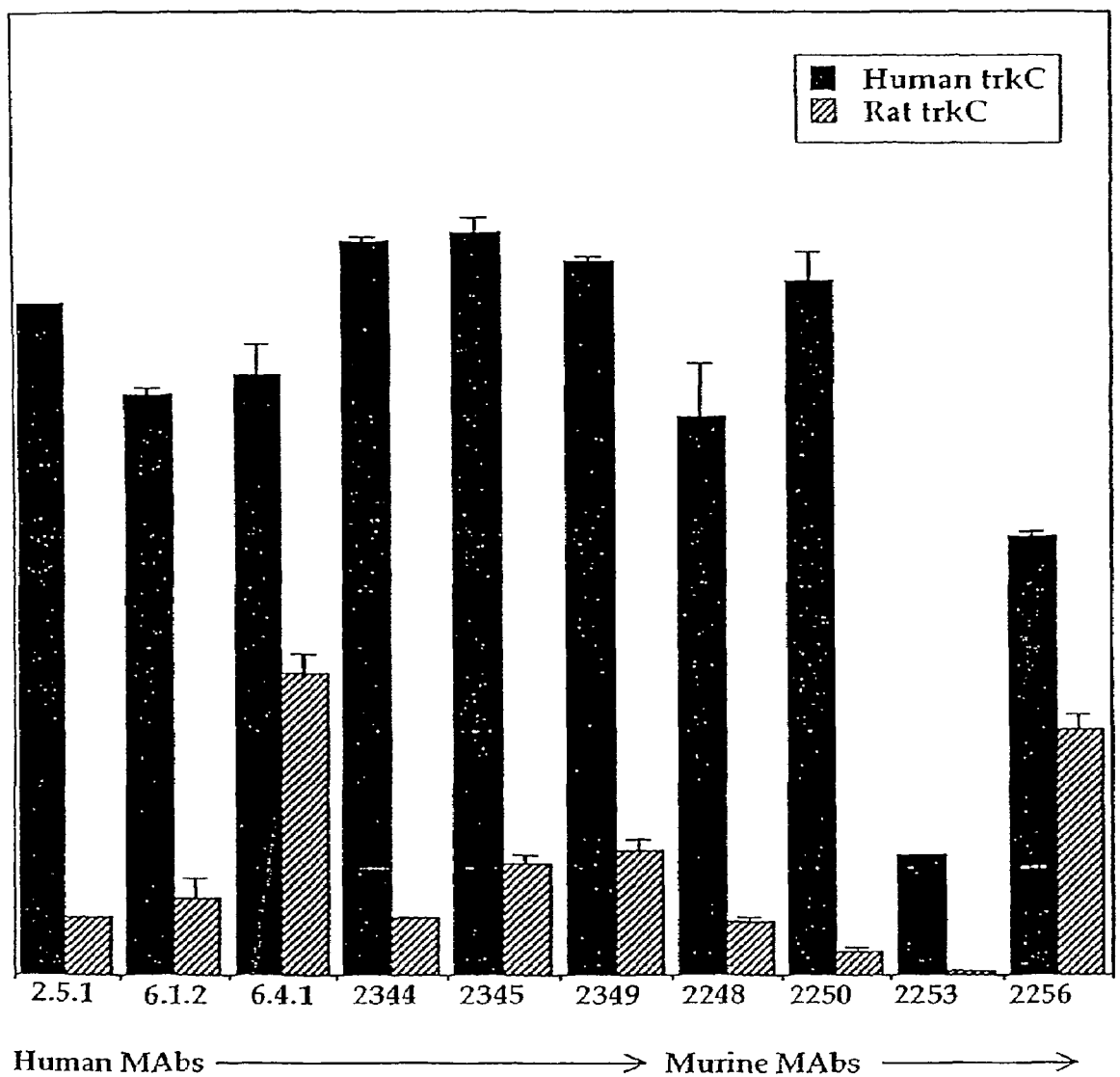
FIG. 3 demonstrates that agonist anti-trkC monoclonal antibodies recognize human trkC more efficiently than rat trkC. The ability of the monoclonal antibodies to bind rat trkC was determined using an immunoadhesin construct of the receptor. TrkC (human trkC-gD or rat trkC-IgG) was immobilized on microtiter plates (100 µl of a 1 µg/ml solution diluted in 50 mM carbonate buffer, pH 9.5) overnight. The plates were washed and blocked. The Mabs were then diluted to 1 µg/ml in PBS containing 0.5% BSA and 0.05% Tween 20, added to the appropriate wells (100 µl/well), and incubated for one hour at room temperature. The plates were washed and the appropriate HRP conjugate was added (human Mabs: goat anti-human κ-HRP, 1:5K; murine Mabs: goat anti-molgG (Fc)-HRP, 1:5 K) and incubated for one hour at room temperature. The plates were then washed, developed and read.

The binding of various anti-trkC agonist monoclonal antibodies to human trkC and rat trkC was compared using a direct ELISA essentially as described above except the capture antigen used for human trkC was trkC-gD instead of trkC-IgG. Results shown in FIG. 3 indicate that among human anti-trkC monoclonal antibodies, only 6.4.1 significantly recognized rat trkC, rest were specific for human trkC. Similarly, among murine monoclonal antibodies, only 2256 recognized rat trkC to a significant extent while others showed specific recognition of human trkC only.

Affinity Studies

Affinities of anti-trkC agonist monoclonal antibodies were determined using using BIAcore-2000™ surface plasmon resonance (SPR) system (BIAcore, Inc., Piscataway, N.J.). CM5 biosensor chips were activated with N-ethyl-N'-(3-dimethylaminopropyl)-carbodiimide hydrochloride (EDC) and N-hydroxysuccinimide (NHS) according to the supplier's instructions. In the first series of binding experiments, the antigen, gD-tagged trkC, was diluted into 10 mM sodium acetate buffer (pH 4.8), and injected over the activated chip at a concentration of 0.09 mg/mL. Using variable exposure times, four ranges of antigen density were achieved: 14,000-17,000 response units (RU), 7000-9000 RU, 2000-3000 RU, and 400-600 RU. The chip was blocked with ethanolamine.

In the first series of kinetic measurements, anti-trkC antibodies (IgG's) were diluted into running buffer (PBS containing 0.05% Tween-20 and 0.01% sodium azide) and 0.03 mL (667 nM) was injected over the biosensor chip at 25° C. at a flow rate of 0.01 mL/min. Regeneration was achieved with a 30 sec pulse of 10 mM HCl, followed by a 1 min pulse of 100 mM Tris-HCl pH 8.0 and two wash steps.

In a second series of experiments, the IgG's (0.1 mg/mL in 10 mM sodium acetate, pH 4.8) were immobilized as described above, except that antibody density was limited to 1000-2000 RU. Two-fold serial dilutions of gD-trkC in the range of 3.7 M to 29 nM were then injected over the biosensor chip for kinetics measurements as described above.

The dissociation phase of each kinetic curve were fit to a single exponential dissociation rate ($k_{off}$), and these rates were used in the calculation of the association rate ($k_{on}$) from the injection phase, using a simple 1:1 Langmuir binding model (Lofas & Johnsson, 1990).

Equilibrium dissociation constants, $K_d$'s, from SPR measurements were calculated as the ratio $k_{off}/k_{on}$.

The affinities of anti-trkC antibodies for gD-trkC were measured in SPR kinetics experiments with either antigen or antibody immobilized. Apparent affinities determined from experiments using low densities of immobilized antigen (0.4 to 0.6 ng/mm2), were generally consistent with those determined in experiments using immobilized IgG (see Table 2). However, at higher densities of immobilized gD-trkC, the apparent binding affinity of each antibody became progressively tighter by factors of as much as 10 fold, probably because of an avidity effect of binding by the bivalent IgG (data not shown). In some cases, no binding could be detected when trkC was injected over immobilized IgG. This may have occurred because immobilization of the IgG led to steric blocking of the antigen-binding site. Under all conditions tested, the antibody 2248 had the highest apparent affinity ($K_d$=5.6 to 8.5 nM) of all antibodies tested.

Binding affinities determined by SPR. Results are shown for IgG's binding to immobilized gD-trkC (400-600 RU) and for gD-trkC binding to immobilized IgG's (1000-3000 RU).

| Antibody (IgG) | $K_d$ (nM) | |
| --- | --- | --- |
| | Immobilized gD-trkC | Immobilized IgG |
| 2248 | 5.9 | 8.5 |
| 2250 | 8.7 | 28 |
| 2253 | 42 | 51 |
| 2256 | 62 | 300 |
| 2344 | 19 | NDB |
| 2345 | 12 | NDB |
| 2349 | 23 | NDB |
| 6.4.1 | 12 | 28 |
| 6.1.2 | 13 | 16 |
| 2.5.1 | 12 | NDB |

NDB = no detectable binding.

Competition ELISA

Figure 4:
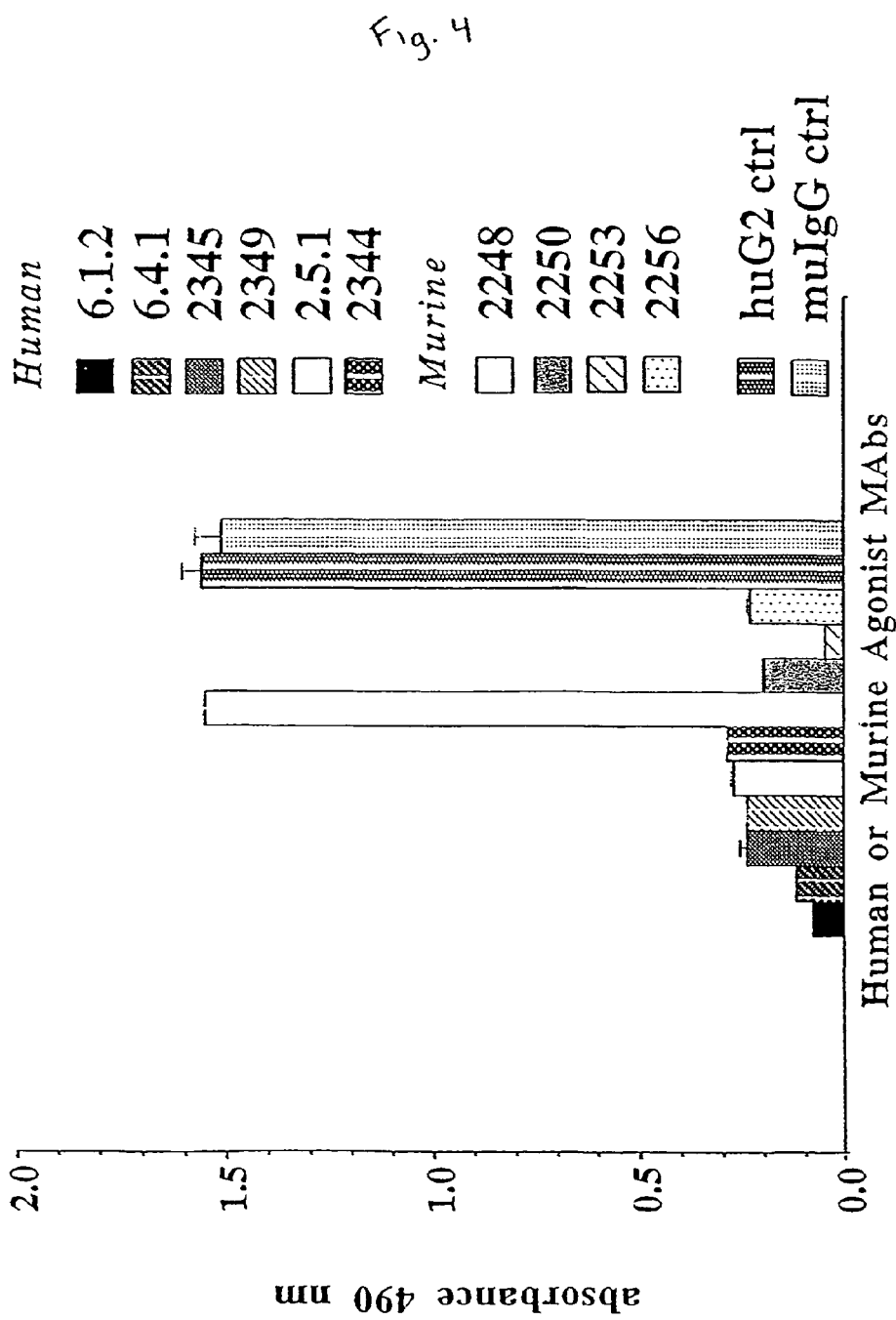
FIG. 4 shows a representative example of epitope mapping using competition ELISA. A biotinylated human anti-trkC 6.1.2 monoclonal antibody was incubated with immobilized trkC in the absence or presence of excess of various unlabeled anti-trkC monoclonal antibodies.

A competition ELISA was used to get preliminary information about various groups to which these antibodies belong depending on the epitope(s) on trkC they recognize. In this assay, trkC-gD (1 μg/ml) was used as a capture antigen to coat microtiter plate. A specific biotinylated anti-trkC monoclonal antibody (1 μg/ml) was added to the coated plate either alone or in presence of another anti-trkC monoclonal antibody that was unlabeled and used in excess (50 μg/ml) as compared to the labeled antibody. If biotinylated antibody and unlabeled antibody both recognize the same or overlapping epitope, they will compete for binding to the immobilized trkC, resulting in decreased binding of the labeled antibody. If they recognize different and non-overlapping epitopes, there will be no competition between them, and the binding of the labeled antibody to the immobilized trkC will not be affected. Unlabeled human IgG2 and mouse IgG were used as negative control. A representative data in FIG. 4 shows that all anti-trkC monoclonal antibodies, except murine anti-trkC 2248 monoclonal antibody, compete with labeled human anti-trkC 6.1.2 monoclonal antibody for binding to the immobilized trkC, suggesting that murine 2248 antibody recognizes an epitope on trkC that is different from the epitope(s) recognized by all other anti-trkC antibodies.

It is interesting to note that when unlabeled murine monoclonal antibody 2248 is bound first to immobilized trkC, none of the other (biotinylated) antibodies can access their binding site, suggesting that even though the epitopes are distinct, steric hinderance may play a role. Such pairwise comparison gives valuable information and helps in classifying antibodies directed against the same antigen into different groups based on epitope recognition. A summary of such comparison is shown in FIG. 5. The results indicate that the antibodies can be divided into two distinct groups: Group 1 encompasses all monoclonal antibodies except 2248, whereas Group 2 is composed of 2248.

Epitope Mapping with Domain Swap Mutants

Figure 6A:
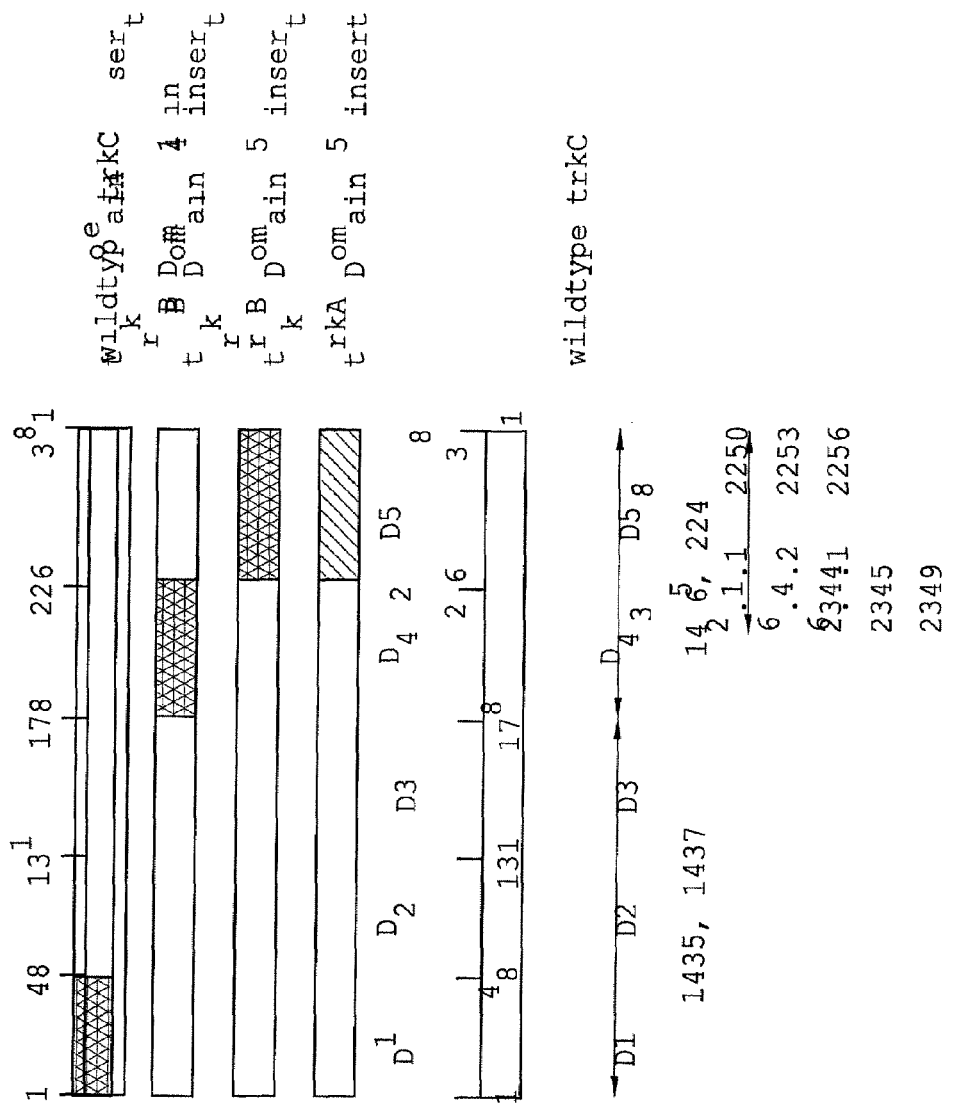
FIGS. 6A-C show a schematic diagram of various trkC chimera (A) and their use in mapping of epitopes on trkC recognized by various agonist human (B) and murine (C) anti-trkC monoclonal antibodies.

Further epitope mapping was performed utilizing chimeric trkC in which various domains were replaced with corresponding domains from trkA or trkB. This approach was made possible by the fact that anti-trkC antibodies do not significantly cross-react with trkA or trkB. The use of such domain-swap mutants has a distinct advantage over deletion mutants. The deletion of a domain might disrupt the secondary structure of protein whereas substitution of a domain with a corresponding domain, of similar size and substantially similar amino acid sequence, from a related protein in domain-swap mutants is likely to retain the secondary structure. The extracellular domain of trk receptors is composed of 5 domains as shown in FIG. 6A. D1 and D3 are cysteine-rich domains, D2 is a leucine-rich domain, and D4 and D5 are immunoglobulin-like domains. Domain-swap mutants of trkC containing replacement of D1, D4 and D5 with the corresponding domains from trkB or trkA were made (Urfer et al., EMBO J. 14:2795-2805 [1995]). Wild type trkC and wild type trkA were used as positive and negative controls respectively. The domain-swap mutants of trkC are designated according to the source of the replaced domain. For example, s1B has D1 domain from trkB, s4B has D4 domain from trkB, s5B has D5 domain from trkB, and s5A has D5 domain from trkA. All of the mutants were expressed as immunoadhesin, i.e. fused to IgG, and purified.

Figure 6B:
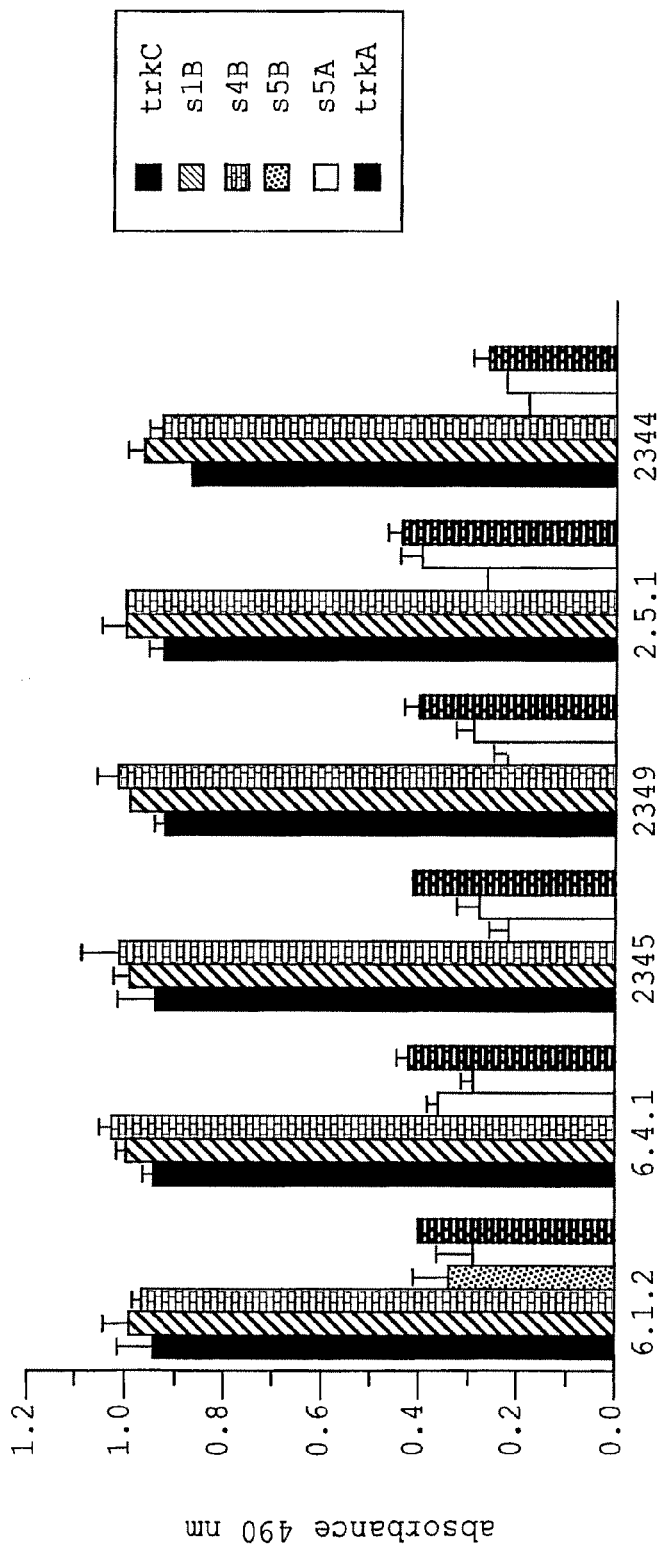
Figure 6C:
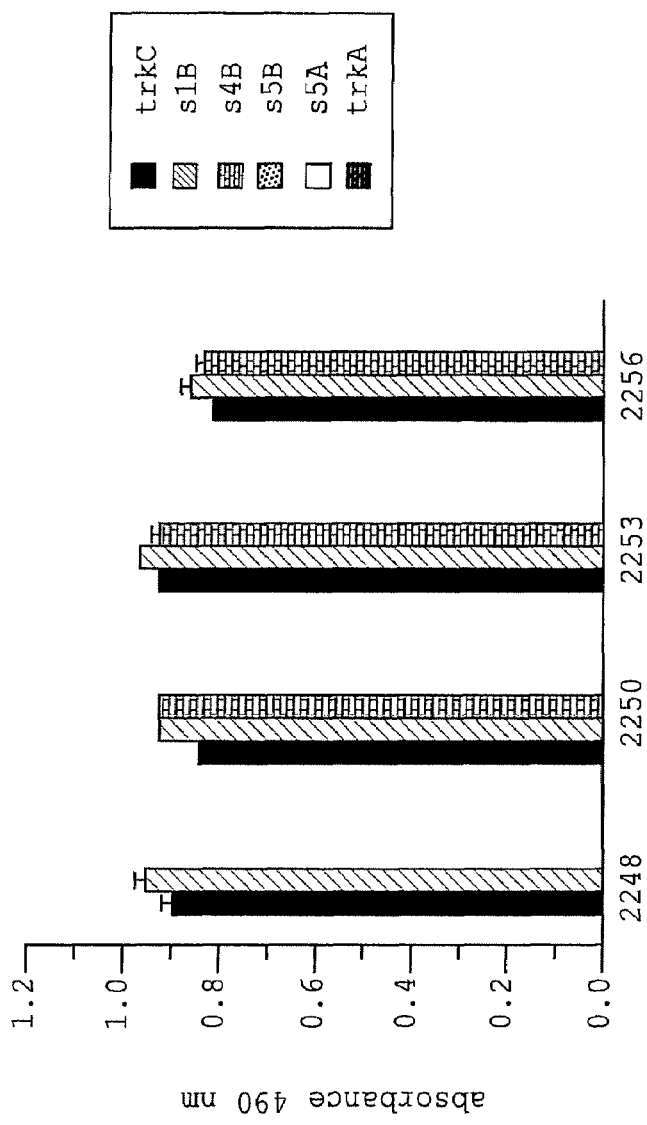

The binding of each of the agonist anti-trkC monoclonal antibody to various domain-swap mutants was evaluated by ELISA. F(ab')$_2$ fragment from goat anti-human IgG was used for coating microtiter plates to capture serial dilutions (100 μg/ml to 2.4 ng/ml, 100 μl/well, one hour at room temperature) of immunoadhesins (trkC-IgG, trkA-IgG and domain-swap mutants of trkC as immunoadhesin). Either unlabeled human or biotinylated murine anti-trkC monoclonal antibodies were added (100 μl per well; 1 μg/ml, one hour at room temperature) to the plates containing immobilized immunoadhesins, washed to remove unbound excess reagents, and incubated with goat anti-human κ or streptavidin conjugated to HRP. As shown in FIG. 6B, all human anti-trkC monoclonal antibodies were able to recognize trkC domain-swap mutants with replacement of domain D1 or D4. However, replacement of domain D5 with the corresponding domain derived from either trkB or trkA destroyed recognition by anti-trkC antibodies. The extent of binding was reduced to the same low level as that observed with a negative control, trkA. The results suggest that all the human anti-trkC monoclonal antibodies tested recognize an epitope located somewhere in domain D5.

Similar analysis was performed with murine anti-trkC monoclonal antibodies essentially the same way except the secondary antibody used was goat anti-mouse IgG Fc coupled to HRP. As with the human anti-trkC antibodies, the replacement of domain D5 abolished binding to all the murine anti-trkC monoclonal antibodies tested (FIG. 6B). Additionally, the replacement of domain D4 also destroyed the binding of 2248 murine anti-trkC antibody. The human as well as murine anti-trkC agonist monoclonal antibodies all seem to recognize an epitope in domain 5 with the exception of 2248 murine antibody, which seems to additionally recognize a determinant in domain 4. It appears that 2248 epitope may be a linear epitope overlapping the boundary of domain 4 and 5. Alternatively, 2248 antibody might recognize a secondary structure formed by discontiguous epitope with determinants derived from both domain 4 and domain 5. Interestingly, Urfer et al. (*J. Biol. Chem.* 273: 5829-5840 [1998]) have earlier established the prominent role of domain 5 in trkC receptor for mediating the interaction with NT-3. Surprisingly, the antibodies described herein also bind to an epitope of trkC which is largely overlapping with that recognized by NT-3. This is surprising because of the relative sizes and shapes of NT-3 and immunoglobulin molecules. The likely mode of action of these activators is to crosslink the extracellular domains of two trkC molecules in such a way to bring together their intracellular tyrosine kinase domains and cross phosphorylate and activate them.

In homodimeric NT-3, it has been established that the two areas of the molecule which interact with trkC are diametrically opposed on opposite sides of the molecule, 180 degrees apart from each other. The distance between these areas is on the order of 16 Å. On the other hand, the two trkC interacting sites in the immunoglobulin molecules described here are not diametrically opposed. In addition to displaying the trkC binding domains at a different angle than NT-3, immunoglobulins will have the trkC binding domains separated from each other by a much wider distance than they are in NT-3. This will vary with the exact angle of the two Fab domains, but is in the range of 50 Å to 150 Å. It would have been difficult to have foreseen that two such very different crosslinkers as NT-3 and the agonist Mabs act as agonists when bound to the same site on trkC.

Site-Directed Mutagenesis

Site-directed mutagenesis approach was used to determine the contribution of selected individual amino acid residues of domain 5 in the recognition by anti-trkC antibodies. FIG. 7 shows the amino acid sequence of human trkC domains 4 and 5. All dotted residues were mutagenized to alanine except residues L284, L286 and E287 which were changed to E, H, and K respectively (Urfer et al., *J. Biol. Chem.* 273: 5829-5840 [1998]). A total of 26 single amino acid mutations were made and evaluated for their effect on binding to anti-trkC monoclonal antibodies. The values shown in Table 5 represent the ratio of binding to anti-trkC antibody of mutant vs wildtype trkC. In order to minimize variation and provide effective comparison, EC50 values were determined for each mutant for each antibody and divided by the EC50 value obtained with wildtype trkC.

TABLE 5

| trkC Mutant | NT-3* | 2.5.1 | 6.1.2 | 6.4.1 | 2344 | 2345 | 2349 | 2248 | 2250 | 2253 | 2256 | 1436 |
|---|---|---|---|---|---|---|---|---|---|---|---|---|
| trkC | 1.0 | 1.0 | 1.0 | 1.0 | 1.0 | 1.0 | 1.0 | 1.0 | 1.0 | 1.0 | 1.0 | 1.0 |
| R275A | 1.1 | | | | | | | | | | | |
| E280A | 0.7 | | | | | | | | | | | |
| E283A | 1.7 | | | | | | | | | | | |
| L284E | 1.1 | NB | NB | NB | NB | NB | NB | 0.7 | 0.6 | 0.7 | 1.1 | 0.8 |
| R285A | 1.5 | 1.1 | 1.2 | 0.8 | 0.9 | 1.0 | 0.9 | 0.8 | 2.6 | 0.9 | NB | 0.4 |
| L286H | 1.2 | 0.6 | 1.3? | NB | 0.9 | 0.5 | 0.6 | 0.6 | 0.4 | 0.4 | 0.6 | 0.6 |
| E287K | 27.3 | NB | NB | NB | NB | NB | NB | 0.6 | 0.8 | 0.7 | 0.7 | 0.6 |
| E291A | 1.0 | | | | | | | | | | | |
| R295A | 11.6 | | | | | | | | | | | |
| Q309A | 1.0 | | | | | | | | | | | |
| R312A | 0.8 | | | | | | | | | | | |
| K315A | 0.9 | | | | | | | | | | | |
| H318A | 1.0 | 0.8 | 1.1 | 0.7 | 0.8 | 1.0 | 0.7 | 1.0 | 1.0 | 0.8 | 0.8 | 1 |

TABLE 5-continued

| trkC Mutant | NT-3* | 2.5.1 | 6.1.2 | 6.4.1 | 2344 | 2345 | 2349 | 2248 | 2250 | 2253 | 2256 | 1436 |
|---|---|---|---|---|---|---|---|---|---|---|---|---|
| E320A | 1.0 | | | | | | | | | | | |
| E324A | 1.2 | | | | | | | | | | | |
| E329A | 1.0 | | | | | | | | | | | |
| N335A | 37.8 | NB | NB | 0.3 | NB | NB | 1.5 | 0.6 | 0.5 | 0.5 | 0.5 | 0.6 |
| K336A | 0.9 | | | | | | | | | | | |
| T338A | 30.3 | | | | | | | | | | | |
| H339A | 1.7 | | | | | | | | | | | |
| K350A | 1.0 | | | | | | | | | | | |
| Q358A | 1.2 | | | | | | | | | | | |
| K366A | 0.9 | | | | | | | | | | | |
| E367A | 1.2 | | | | | | | | | | | |
| D372A | 1.2 | | | | | | | | | | | |
| E373A | 1.1 | | | | | | | | | | | |

Figure 8:
FIG. 8 shows 3-dimensional ribbon diagram of trkC in complex with anti-trkC monoclonal antibodies. Specifically shown are the amino acid residues of trkC that are likely to play an important role in recognition by CDRs of anti-trkC antibodies.

The gray areas indicate that the designated mutants did not have an initial effect on monoclonal antibody binding, and were therefore not re-assayed. Mutations that completely obliterated monoclonal antibody binding are shown as NB ("no binding observed"). The analysis indicates the major contribution of amino acid residues L284, E287 and N335 of trkC in recognition by anti-trkC agonist monoclonal antibodies tested. A model of the complex of trkC domain 5 with NT3 shows the position of these residues in close contact with CDRs of antibody (FIG. 8). This model is based on the crustal structure of the complex of trkA domain 5 wih NGF. For further details see, e.g. Urfer et al. *J. Biol. Chem.* (1998), supra, or Ultsch et al., *J. Mol. Biol.* 290:149-159 (1999).

Cloning and Sequencing of Antibody Variable Regions

In order to better understand the molecular basis of interaction between trkC and anti-trkC monoclonal antibodies, the heavy and light chain variable sequences of agonist antibodies were cloned and DNA sequence determined. Total RNA was isolated from hybridoma cells producing the human and murine anti-trkC antibodies using RNA isolation kit from Stratagene (La Jolla, Calif.). RNA was reverse transcribed into cDNA using SuperScript II system (Life Technologies, Inc., Gaithersburg, Md.) and specific 3' primers based on framework 4 sequences derived from the respective heavy or light chain subgroup (Kabat and Wu, *J. Immunol* 147: 1709-1719 [1991]). Subsequent PCR amplification was performed using AmpliTaq DNA polymerase (Perkin Elmer, Foster City, Calif.) in presence of 2.5 M DMSO with specific forward primers based on the N-terminal amino acid sequences of heavy and light chains and the same 3' primers used for cDNA synthesis. PCR products were subcloned into an F(ab)'$_2$ vector containing both human heavy and light chain constant regions (Carter et al., *Bio/Technology* 10: 163-167 [1992]). Five clones each of the $V_H$ and $V_L$ domains were sequenced and a consensus sequence was obtained.

FIG. 9 shows the deduced amino acid sequences of heavy chain of anti-trkC agonist monoclonal antibodies (2250, SEQ ID NO: 42; 2253, SEQ ID NO: 43; 2256, SEQ ID NO: 44; 6.1.2, SEQ ID NO: 45; 6.4.1, SEQ ID NO: 46; 2345, SEQ ID NO: 47; and 2349, SEQ ID NO: 48). The deduced amino acid sequences of light chain of anti-trkC agonist monoclonal antibodies are shown in FIG. 10 (2250, SEQ ID NO: 49; 2253, SEQ ID NO: 50; 2256, SEQ ID NO: 51; 6.1.2, SEQ ID NO: 53; 6.4.1, SEQ ID NO: 53; 2345, SEQ ID NO: 54; and 2349, SEQ ID NO: 55). In both FIG. 9 and FIG. 10 the Complementarity Determining Regions (CDRs) are labeled as CDR1, CDR2 and CDR3, and the corresponding amino acid residues are shown in bold face. FIG. 11 summarizes the sequences of CDRs of heavy chain as well as light chain of various anti-trkC monoclonal antibodies along with designation of respective heavy and light chain variable family to which they belong.

Based on the determined amino acid sequences of the CDRs of the heavy and light chains of the anti-trkC agonist monoclonal antibodies, it is possible to provide a general formula for several of these regions. For the murine antibodies, the heavy chain CDR1 may be represented by the formula XaaWXaaXaaWVK (SEQ ID NO:37), wherein Xaa at position 1 is F or Y, Xaa at position 3 is I or M and Xaa at position 4 is E or H. The murine heavy chain CDR2 may be represented by the formula EIXaaPXaaXaaXaaXaaTNYNEK-FKXaa (SEQ ID NO:38), wherein Xaa at position 3 is L or Y, Xaa at position 5 is G or S, Xaa at position 6 is S or N, Xaa at position 7 is D or G, Xaa at position 8 is N or R and Xaa at position 17 is G or S. The murine heavy chain CDR3 may be represented by the formula KNRNYYGNYVV (SEQ ID NO:12) or KYYYGNSYRSWYFDV (SEQ ID NO:13). For the human antibodies, the heavy chain CDR1 may be represented by the formula XaaXaaXaaYYWXaa (SEQ ID NO:39), wherein Xaa at position 1 is S or I, Xaa at position 2 is G or S and Xaa at position 3 is G, T or Y and Xaa at position 7 is S or N. The human heavy chain CDR2 may be represented by the formula XaaIXaaXaaSGSXaaTXaaNPSLKS (SEQ ID NO:40), wherein Xaa at position 1 is Y or R, Xaa at position 3 is Y or F, Xaa at position 4 is Y or T, Xaa at position 8 is S or R and Xaa at position 10 is N or Y. The human heavy chain CDR3 may be represented by DRDYDSTGDYYSYYG-MDV (SEQ ID NO:14), DGGYSNPFD (SEQ ID NO:15) or the formula ERIAAAGXaaDYYYNGLXaaV (SEQ ID NO:41) wherein Xaa at position 8 is A or T and Xaa at position 16 is D or A.

The deduced amino acid sequence of heavy and light chain variable regions was confirmed by determination of N-terminal peptide sequence of these antibodies. Electroblotting onto Millipore Immobilon-PSQ membranes was carried out for 1 hr at 250 mA constant current in a BioRad Trans-Blot transfer cell (Matsudaira, *J. Biol. Chem.* 262: 10035-10038 [1987]). The PVDF membrane was stained with 0.1% Coomassie Blue R-250 in 50% methanol, 0.5 min. and destained for 2-3 min. with 10% acetic acid in 50% methanol. The mebrane was thoroughly washed with water and allowed to dry before storage at 20° C. Automated protein sequencing was performed on model 494A Perkin-Elmer sequencer (Perkin-Elmer Corporation, Foster City, Calif.) equipped with on-line PTH analyzer. Protein electroblotted onto PVDF membrane were sequenced in 6 mm micro glass cartridge. Peaks were integrated with Justice Innovation software using Nelson Analytical 760 interfaces. Sequence interpretation was performed on a DEC Alpha (Henzel et al., *J. Chromatography* 404: 41-52 [1987]). Table 6 summarizes the classification of human and murine anti-trkC agonist monoclonal antibodies based on their N-terminal sequences.

TABLE 6

|  | Heavy chain | Light chain |
|---|---|---|
| Human anti-trkC agonist mAbs | | |
| 6.1.2 | Subgroup II | Kappa I |
| 6.4.1 | Subgroup II | Kappa I |
| 2345 | Subgroup II | Kappa III |
| 2349 | Subgroup II | Kappa III |
| 2.5.1 | Subgroup II | Kappa I |
| 2344 | Subgroup II | Kappa I |
| Murine anti-trkC agonist mAbs | | |
| 2248 | Subgroup IIA | Kappa I |
| 2250 | Subgroup IIA | Kappa I |
| 2253 | Subgroup IIA | Kappa IV |
| 2256 | Subgroup IIA | Kappa III |

Example 2

Effect of Agonist Anti-trkC Monoclonal Antibodies on Neuropathies in Experimental Animal Model The principal use of NT-3 agonists is in the treatment and/or prevention of peripheral neuropathies. It is known that large fiber myelinated sensory neurons, which are involved in mediating proprioception and vibration sense, express trkC that acts as a high affinity receptor for NT-3. Neuropathies involving these large fibers are common in diabetes and are also induced in response to certain chemotherapeutic agents particularly cisplatin and pyridoxine. NT-3 has shown efficacy in animal models of experimental diabetic neuropathy and cisplatin induced neuropathy. However, the use of NT-3 is severely hampered by its poor bioavailability as shown in a rodent model. The use of anti-trkC Monoclonal antibodies as agonist of NT-3 offers numerous advantages and obviates a number of potential problems associated with the use of NT-3.

Figure 12:
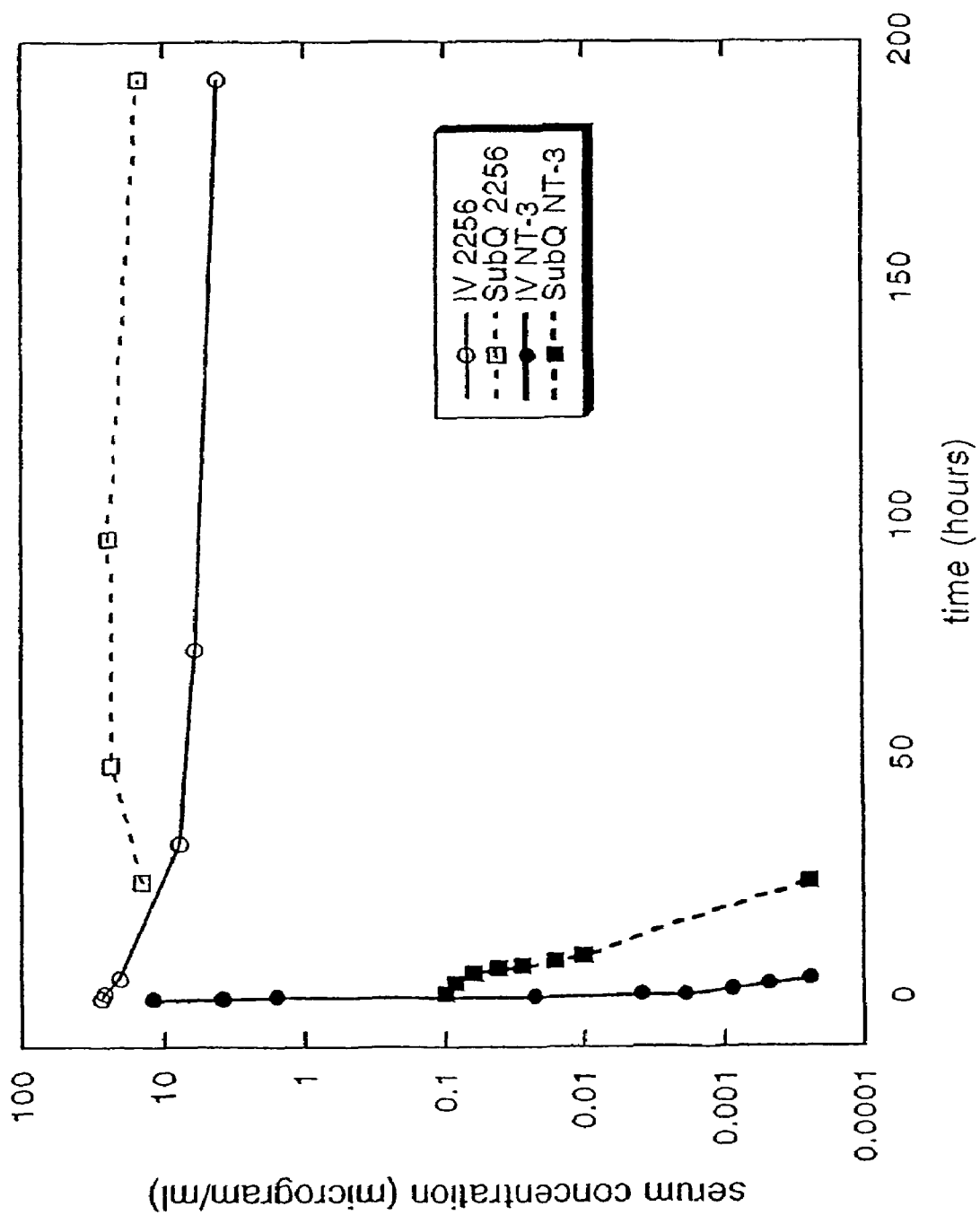
FIG. 12 shows that anti-trkC agonist monoclonal antibodies have improved half-life and bioavailability in vivo.

The in vivo half-life of agonist anti-trk monoclonal antibodies was determined by injecting either intravenously or subcutaneously in experimental animals. Shown on FIG. 12 are serum levels of monoclonal antibody 2256 at various times after intravenous (IV) injection of 1 mg/kg or subcutaneous (subQ) injection of 5 mg/kg in rats. The serum levels were determined b using the KIRA assay to measure the amount of fully functional antibody 2256 by its ability to increase tyrosine autophosphorylation of trkC. These data indicate that monoclonal antibody 2256 in the rat has a half-life of 9 days and a bioavailability of 69% after subcutaneous administration. These values are consistent with those obtained with other antibodies, and are distinctly different from those obtained with NT3. Also shown in FIG. 12 is data obtained after injection of NT-3 at the same doses and routes as shown for Mab 2256 (1 mg/kg, IV; 5 mg/kg subQ). These data indicate a serum half-life on the order of 4-5 minutes for NT-3, and a subcutaneous bioavailability of 7%. These data indicate that the antibodies are a significant improvement over NT-3 in terms of the very important properties of bioavailability and in vivo serum half-life.

It has been shown in two animal models of large fiber sensory neuropathy that NT-3 can protect or reverse the effects of chemical insult. Very high doses of NT3 have been shown to protect large fiber sensory neurons from the toxic effects of high doses of pyridoxine, and more moderate doses of NT3 have been shown to reverse the effects of cisplatinum administration. Since there might be many differences in the tissue distribution of NT-3 and the agonist Mabs described here, it is important to determine whether the in vitro activity of the Mabs translates into efficacy in animal models.

In order to create an animal model of cisplatinum induced neuropathy, adult rats were dosed with cisplatinum twice a week for sixteen weeks with 1 mg/kg intraperitoneally (IP). At this point, rats were split into four groups. All four groups continued receiving cisplatinum twice weekly. In addition to the continued cisplatinum, one group received NT-3 at a dose of 1 mg/kg, three times per week, one group received Mab 2256 at a dose of 1 mg/kg once a week, one group received Mab 6.4.1 at a dose of 1 mg/kg once a week, and one group received saline three times a week. The NT-3 doses were given subcutaneously, while the Mabs and saline were administered IV. This treatment regime was continued for an additional four weeks, for a total of twenty weeks of cisplatinum administration.

Figure 13:
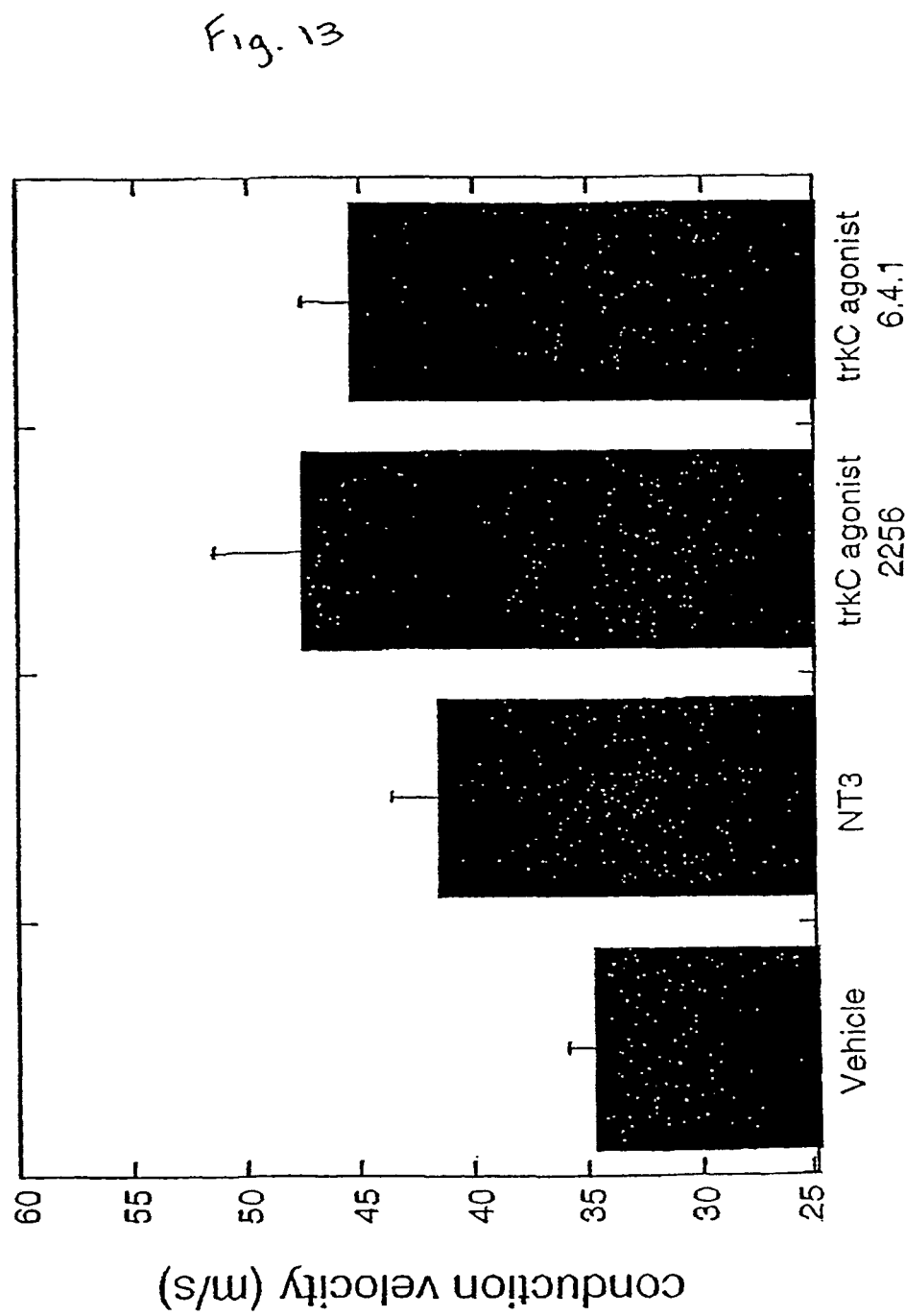
FIG. 13 shows effect of anti-trkC agonist monoclonal antibodies on cisplatin-induced neuropathy.

The function of large fiber sensory neurons was assessed in these animals electrophysiologically, by use of H-wave recording (Gao et al., *Ann. Neurol.* 38(1):30-7 [1995]) As can be seen from the data shown in FIG. 13, the sensory conducton velocity was very low in the animals treated with cisplatinum with saline alone. NT-3 treatment three times a week caused an improvement of this lowered conduction velocity, as did treatment with either Mab 2256 or Mab 6.4.1 once a week. The magnitude of the improvement seen with the monoclonal antibodies used once a week was at least as great as that seen with three times a week treament with NT-3.

Pyridoxine is also know to induce a sensory neuropathy that primarily damages the large myelinated subpopulation of sensory neurons (Helgren et al., *J. Neurosci.* 17(1):372-82 [1997]). High doses of NT3 have been shown to block the development of this neuropathy (Helgren et al., supra). Treatment of animals with two different doses of pyridoxine (either 400 mg/kg or 600 mg/kg daily, IP) for two weeks causes damage to the large neurons of the DRG. This damage can be detected by a decrease in the expression of several proteins known to be expressed either preferentially or exclusively by large neurons in the ORG. The expression level of these markers was assessed by measuring the level of the mRNA encoding them by use of the TAQMAN RT-PCR technique.

Taqman RT-PCR for trkC Agonist Effects:

A. Probes and Primers

NFL

| | | |
|---|---|---|
| F-CAGCAGAACAAGGTCCTGGAA 21MER | (SEQ ID NO: 72) |
| R-AGCGGGAAGGCTCTGAGTG 19MER | (SEQ ID NO: 73) |
| P-AGCTGTTGGTGCTGCGCCAGAA 22MER | (SEQ ID NO: 74) |

NSE

| | | |
|---|---|---|
| F-TCCATTGAAGACCCATTCGAC 21MER | (SEQ ID NO: 75) |
| R-GCCGACATTGGCTGTGAAC 19MER | (SEQ ID NO: 76) |
| P-AGGATGACTGGGCAGCTTGGTCCA 24MER | (SEQ ID NO: 77) |

TRKC

| | | |
|---|---|---|
| F-CAGCCCACTGCACCATATCA 20MER | (SEQ ID NO: 78) |
| R-CTGTATCCGGCCCAGCAT 18MER | (SEQ ID NO: 79) |
| P-CCATGGCATCACTACACCTTCATCGCT 27MER | (SEQ ID NO: 80) |

CALRET

| | | |
|---|---|---|
| F-TGGGAAAATTGAGATGGCAGA 21MER | (SEQ ID NO: 81) |
| R-GCTGCCTGAAGCACAAAAGG 20MER | (SEQ ID NO: 82) |
| P-CGCAGATCCTGCCAACCGAAGAGA 24MER | (SEQ ID NO: 83) |

PARVALB.

| | | |
|---|---|---|
| F-GACACCACTCTTCTGGAAAATGC 23MER | (SEQ ID NO: 84) |
| R-TTGCCAAACCAACACCTACCA 21MER | (SEQ ID NO: 85) |
| P-ATCGGACACCACCTGTAGGGAGGACC 26MER | (SEQ ID NO: 86) |

GAPDH

| | | |
|---|---|---|
| F-CAGTGGCAAAGTGGAGATTGT 21MER | (SEQ ID NO: 87) |
| R-AATTTGCCGTGAGTGGAGTC 20MER | (SEQ ID NO: 88) |
| P-CCATCAACGACCCCTTCATTGACCTC 26MER | (SEQ ID NO: 89) |

Probes and primers were designed using Primer Express, (ABI-Perkin-Elmer). Guidelines for primer probe selection are included in Williams and Tucker (1999) PCR applications, pp. 365-75 (Academic Press).

B. Total RNA Preparation and Quantification

L4 and L5 were dissected from phosphate buffered saline perfused rats. Left and right sides were isolated in separate tubes. For total RNA used in standard curves, all DRG were dissected from control rats. Total RNA was isolated using the Qiagen Rneasy mini columns. Tissue was homogenized as per manufacturers instructions. Total RNA was quantified utilizing the Ribogreen Quantitaion Kit (Molecular Probes) and following the manufacturers instructions.

C. RT-PCR

Twenty five nanograms of total RNA was used per 50 ul reaction, except in standard curve reactions where 500, 250, 25 or 2.5 nanograms per reaction was used. Each reaction contained 25 pmol of each oligonucleotide primer, 0.2 mM of each dNTP, 100 nM flourescently labelled oligonucleotide probe, 1×RT-PCR buffer (PE biosystems), 2.0 mM MgCl2, 20 U RNAse inhibitor, 12.5 MuLV reverse transcriptase (RT, PE biosystems) and 2.5 U Amplitaq Gold polymerase (PE biosystems). Reverse transcription was performed for 30 min at 48 degrees C. followed by 95 degrees C. for 10 min for Amplitaq Gold activation and RT inactivation, then PCR; 40 cycles of 95 degrees C. for 15 sec and 60 degrees C. for one and a half minutes.

D. Gene Expression Quantitation

Control RNA was used to generate standard curves for a housekeeping gene and the genes of interest with each taqman run. A standard curve was obtained by plotting the threshold cycle (Ct) value obtained from the Taqman run versus the log of the quantity of control total RNA added. The resultant linear equation was solved for the log RNA value. Plugging in the experimental Ct value produced the log of the experimental gene expression value. Ten raised to the power of this value gives the experimental gene expression in nanograms.

Figure 14:
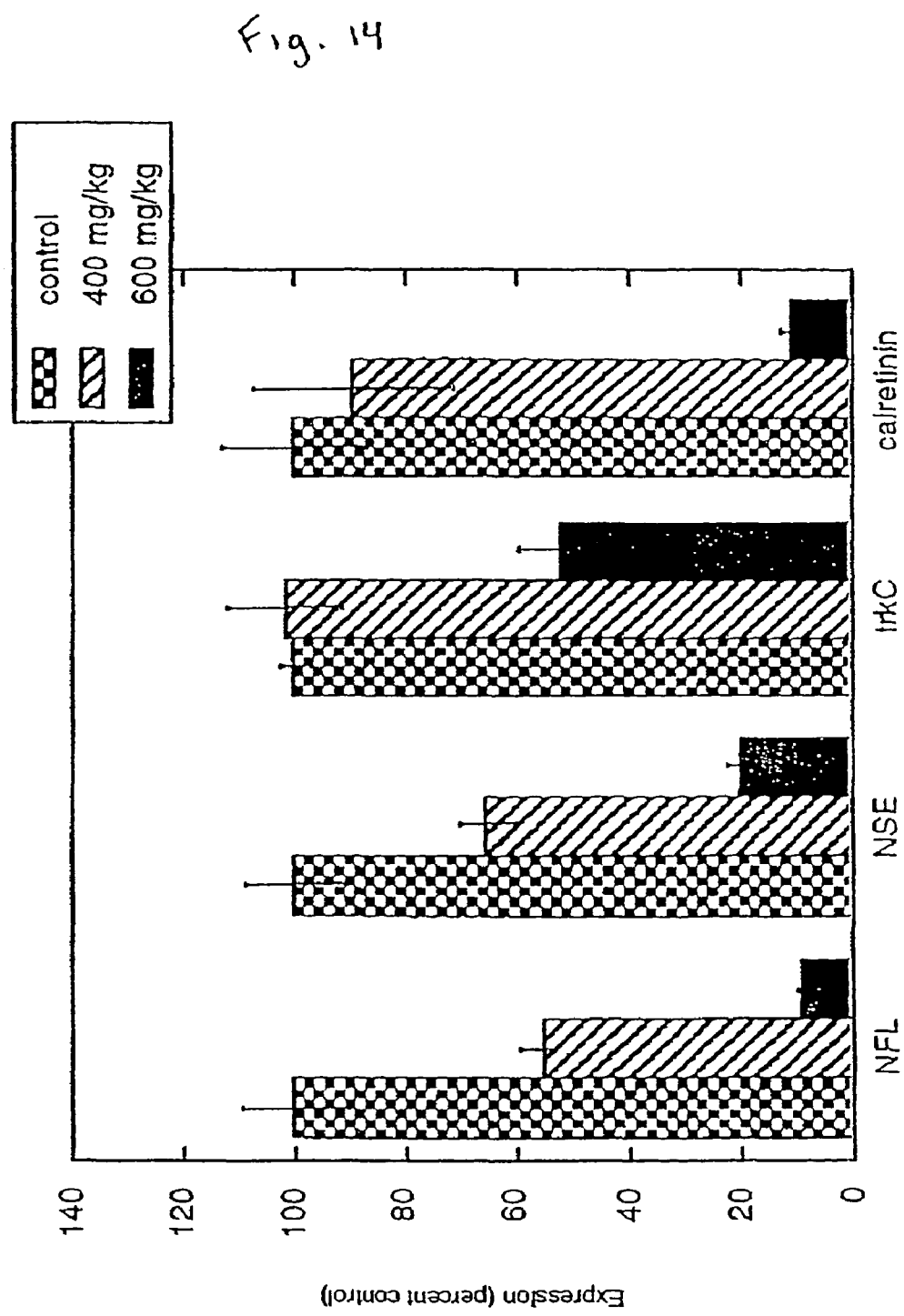
FIG. 14 shows decrease in marker expression caused by pyridoxine neuropathy.

As can be seen from FIG. 14, pyridoxine treatment for two weeks resulted in a dose dependent decrease in neurofilament light chain (NFL), neuron specific enolase (NSE), trkC, and calretinin expression. Both the dose dependency and magnitude of these decreases varies from marker to marker, indicating a differential sensitivity of these proteins as markers of the neuronal damage.

Figure 15:
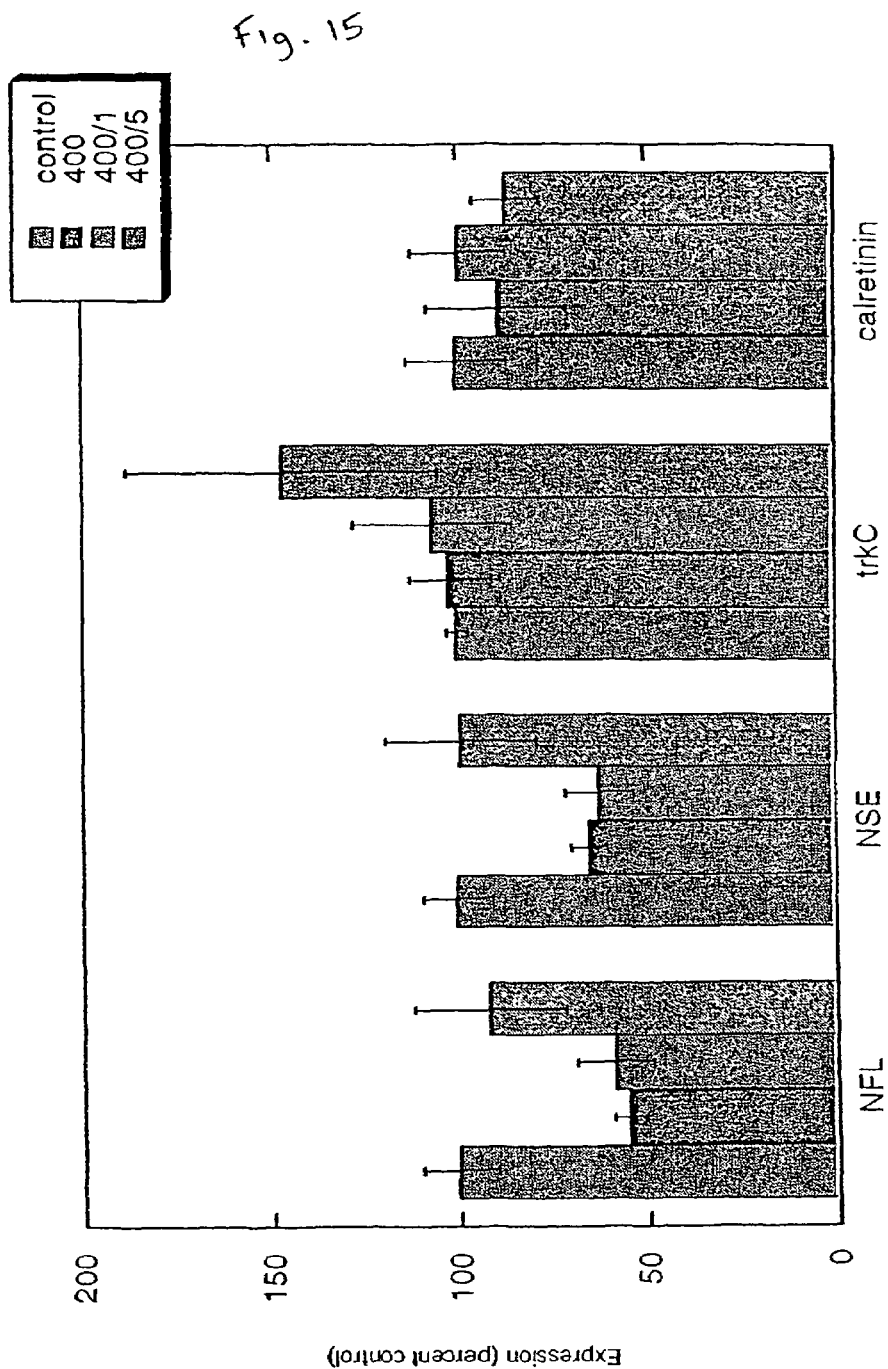
FIG. 15 shows amelioration of the effects of low doses of pyridoxine by agonist anti-trkC monoclonal antibodies.

In FIG. 15 the results of treating animals with two doses of Mab 2256 along with the low dose (400 mg/kg daily) of pyridoxine are shown. NFL and NSE show a significant decrease in expression at this level of pyridoxine treatment. Cotreatment of animals with 5 mg/kg of Mab 2256 (subQ weekly) completely blocked this decrease in expression. A Mab 2256 dose of 1 mg/kg had no appreciable effect on the expression of these proteins. Neither trkC nor calretinin expression is significantly affected by this low dose pyridoxine treatment, but treatemtn with 5 mg/kg Mab 2256 actually increases trkC expression over control level.

Figure 16:
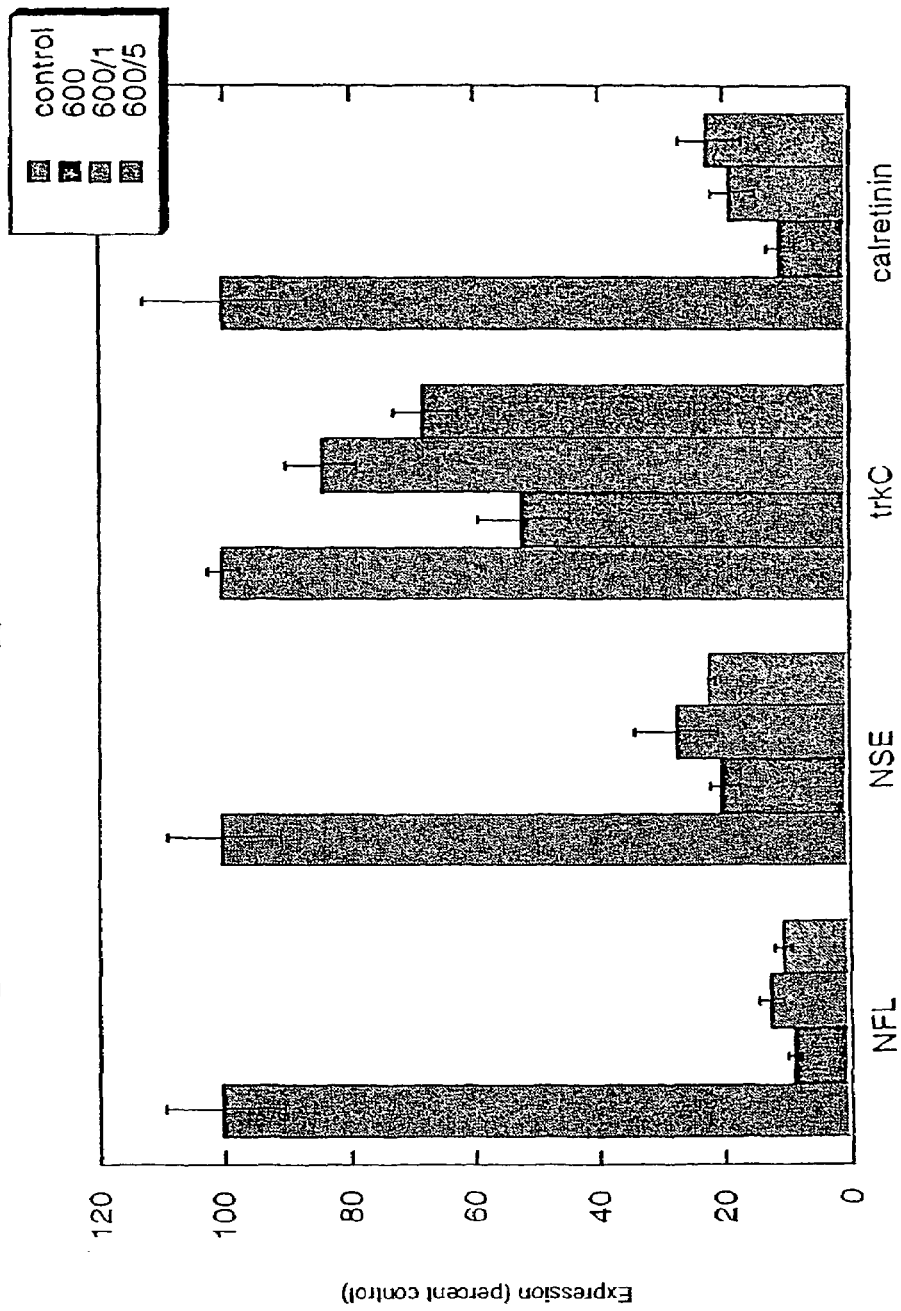
FIG. 16 shows amelioration of the effects of high doses of pyridoxine by agonist anti-trkC monoclonal antibodies.
Figure 17:
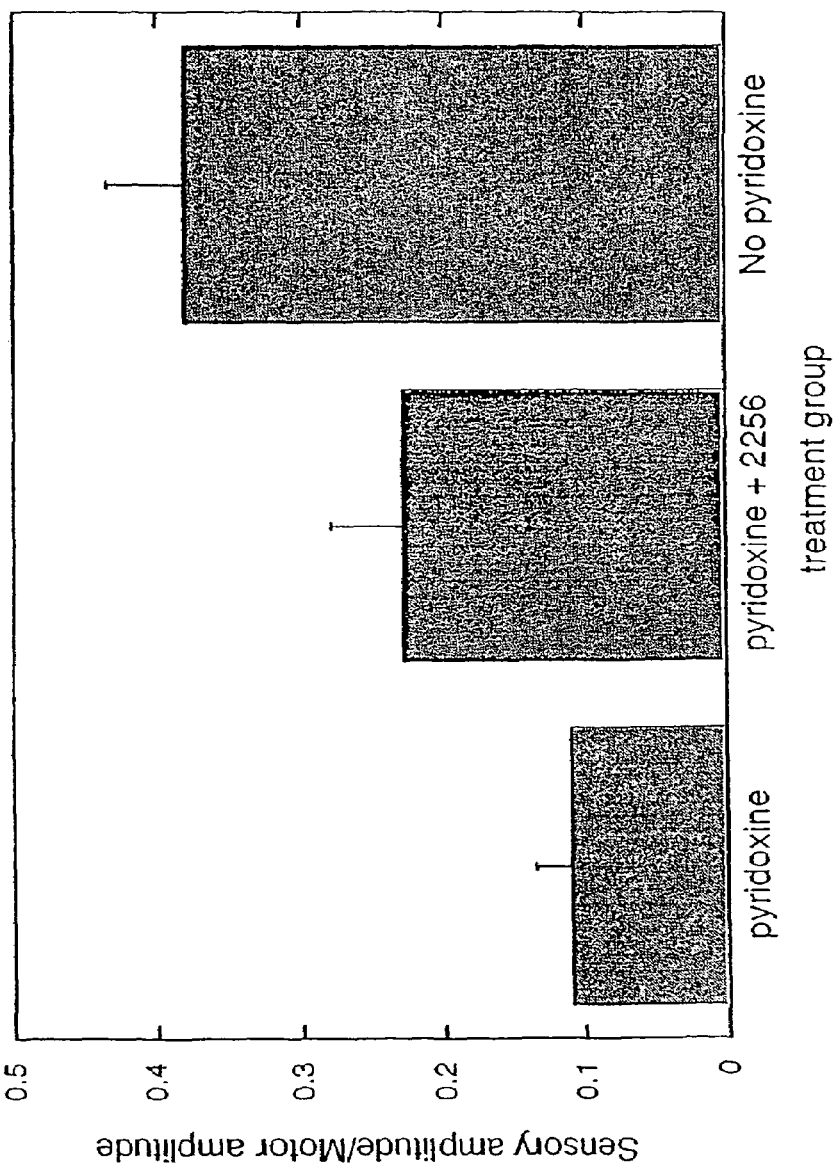
FIG. 17 shows amelioration of pyridoxine neuropathy by an anti-trkC agonist monoclonal antibody.

When animals are treated with the higher pyridoxine dose of 600 mg/kg daily, the expression of NFL, NSE and calretinin falls to very low levels, while trkC expression falls to about 50% of control values (FIG. 16). Cotreatment with Mab 2256 at either 1 mg/kg or 5 mg/kg significantly but not completely blocks the decrease in expression seen in trkC and calretinin. There is a slight trend towards protection seen with NFL and NSE expression in animals treated with Mab 2256, but it did not attain statistical significance. Thus, using multiple biochemical markers of damage to large sensory neurons, Mab 2256 is seen to be capable of ameliorating the toxicity of pyridoxine treatment.

Figure 18:
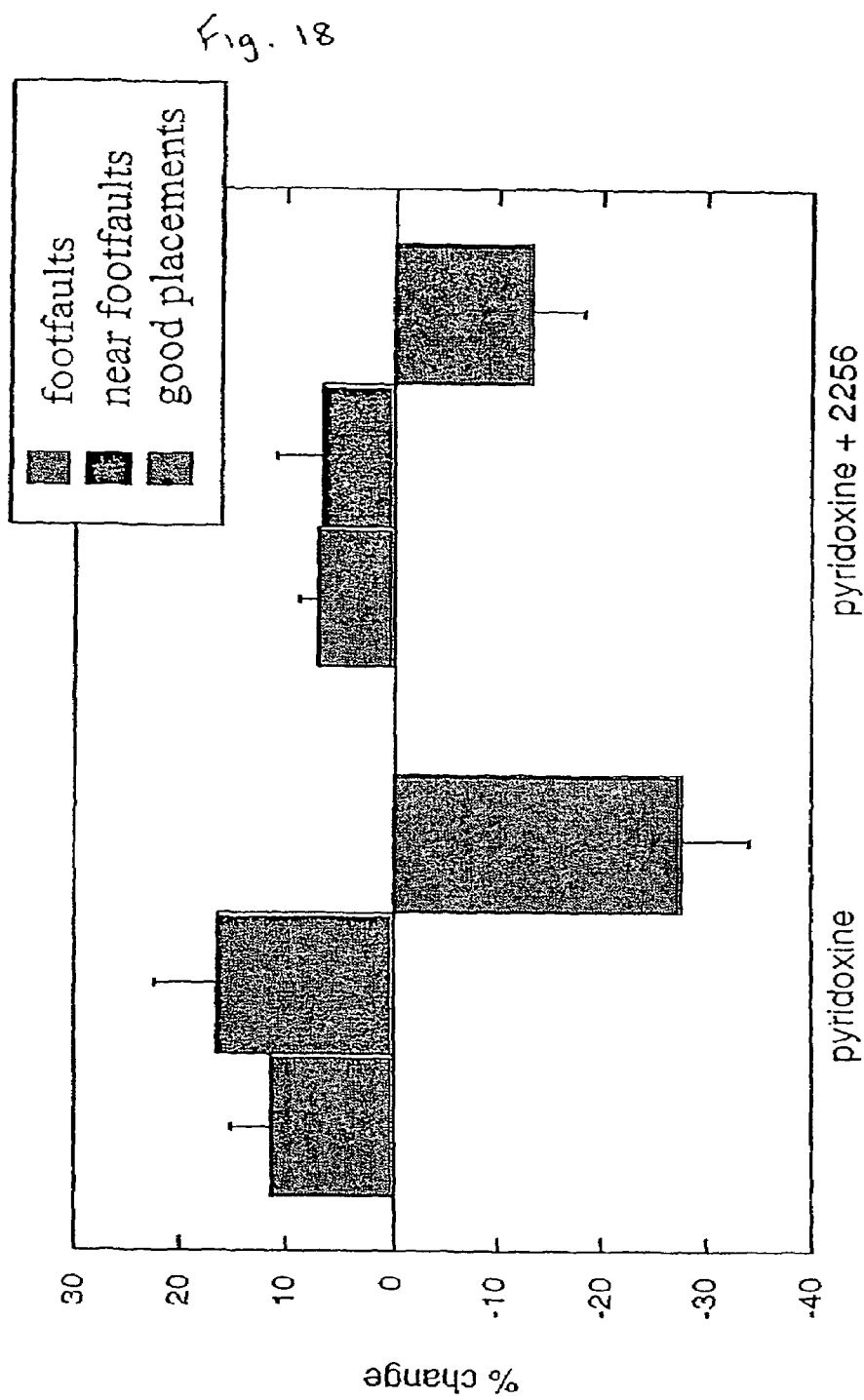
FIG. 18 shows attenuation of pyridoxine-induced deficit of ladder by agonist anti-trkC monoclonal antibodies.

In order to examine the electrophysiolgical and behavioral effects of pyridoxine neuropathy, rats were treated with twice daily injections of 400 mg/kg pyridoxine for 8 days. The function of their large diameter sensory afferents were tested electrophysiologically by recording the M-wave (direct motor) and H-wave (reflex sensory) response in the muscles of the foot after stimulation of the sciatic nerve at the thigh and the calf (Gao et al. *Ann. Neurol.* 38(1):30-7 [1995]). Treatment with pyridoxine for 8 days resulted in a large decrease in the amplitude of the sensory response compared to the motor response as seen in FIG. 18. Cotreatment with Mab 2256 significantly blocked the pyridoxine-induced decrease in the sensory amplitude. This is similar to effects published using very high doses (20 mg/kg daily) of NT3 (Helgren et al., supra).

Animals treated with this regime of pyridoxine were also behaviorally tested for their proprioceptive function. They were trained to walk across a horizontal ladder in order to escape a bright light and white noise stimulus into a dark box. The animals were videotaped from below, and the quality of the placement of their hindpaws on the rungs of the ladder was read by an observer blind to their treatment. Each paw placement was scored as a good placement (paw lands on forward part of metatarsals, immediately behind toes, with toes wrapping the rung immediately), solid landing (paw hits other than immediately behind toes, but solidly on rung, toes often not wrapping), near footfault (paw barely hits rung, either on the extreme forward part of toes or rearward aspect of heel, but does support weight) or footfault (paw either misses rung entirely or poor enough placement that foot does not support weight and falls through ladder upon weight bearing). Normal rats very quickly learn to place their hindpaws correctly, which requires an excellent proprioceptive sense of where the hindpaw is in space. After treatment with pyridoxine (400 mg/kg twice daily for 8 days), the performance on this task had declined, with an almost thirty percent decline in good placements and an increase in both footfaults and near footfaults (FIG. 18). Cotreatment of the animals with Mab 2256 during this time, allowed the animals to maintain a much higher degree of performance, with a smaller decline in good placements and smaller increases in footfaults and near footfaults.

In summary, cotreatment with Mab 2256 ameliorates the toxic effects of pyridoxine as measured biochemically, electrophysiologically, and by performance on a behavioral task.

After establishing that the trkC Mabs were therapeutically at least as effective as NT-3, the observed adverse event of hyperalgesia was examined. This side effect of NT-3 administration has been seen in rodents (see FIG. 19) and in humans (Chaudhary et al., *Muscle and Nerve* 23:189-192 [2000]). Rats were trained and tested for thermal sensitivity of the hind paws using a Hargreaves device and then administered 1 mg/kg of Mab 2256 IV, or 1 mg/kg NT-3 subcutaneously in the scruff. At two, four, and six hours after administration, the rats were again tested for their thermal withdrawal times. As can be seen from FIG. 19, NT-3 administration caused a significant heat hyperalgesia at four and six hours post dosing, while the trkC Mab 2256 was without any effect on thermal pain sensation. So, at doses known to be effective in reversing or preventing neuropathyy, NT-3 does cause an increase in sensitivity to pain, while the Mab 2256 does not.

Cisplatin, a widely used chemotherapeutic agent, induces a sensory neuropathy with selective loss of vibration sense and proprioception. Here we demonstrate that neurotrophin-3 (NT-3), a member of the nerve growth factor family of neurotrophic factors, restored to normal levels the reduced H-reflex-related sensory nerve conduction velocity induced by cisplatin in rats. NT-3 treatment corrected an abnormal cytoplasmic distribution of neurofilament protein in large sensory neurons in dorsal root ganglia and the reduction in the numbers of myelinated fibers in sural nerves caused by cisplatin. The NT-3-dependent reversal of cisplatin neurotoxicity thus suggests the possible use of NT-3 in the treatment of peripheral sensory neuropathy.

Chronic treatment of adult rats for 2-3 weeks with high doses of pyridoxine (Vitamin B6) produced a profound proprioceptive loss, similar to that found in humans overdosed with this vitamin or treated with the chemotherapeutic agent cisplatin. Pyridoxine toxicity was manifest as deficits in simple and precise locomotion and sensory nerve function and as degeneration of large-diameter/large-fiber spinal sensory neurons. As assessed quantitatively in a beam-walking task and by EMG recording of H waves evoked by peripheral nerve stimulation, coadministration of the neurotrophic factor neurotrophin-3 (NT-3; 5-20 mg/kg/day, s.c.) during chronic pyridoxine treatment largely attenuated the behavioral and electrophysiological sequelae associated with pyridoxine toxicity. Furthermore, NT-3 administration prevented degeneration of sensory fibers in the dorsal column of the spinal cord. These data are consistent with the evidence that NT-3 is a target-derived neurotrophic factor for muscle sensory afferents and suggest that pharmacological doses of NT-3 may be beneficial in the treatment of large-fiber sensory neuropathies.

Deposit of Biological Material

The following hybridoma cell lines and plasmids have been deposited with the American Type Culture Collection, 10801 University Boulevard, Manassas, Va. 20110-2209, USA (ATCC) on Jun. 21, 2000:

| Hybridoma/Plasmid Designation | ATCC No. |
| --- | --- |
| 2.5.1 | PTA-2151 |
| 6.1.2 | PTA-2148 |
| 6.4.1 | PTA-2150 |
| 2344 | PTA-2144 |
| 2345 | PTA-2146 |
| 2349 | PTA-2153 |
| 2248 | PTA-2147 |
| 2250 | PTA-2149 |
| 2253 | PTA-2145 |
| 2256 | PTA-2152 |
| DNA pXCA-2250HL | PTA-2136 |
| DNA pXCA-2253HL | PTA-2137 |
| DNA pXCA-2256HL | PTA-2138 |
| DNA pXCA-6.1.2H | PTA-2141 |
| DNA pXCA-6.4.1H | PTA-2143 |
| DNA pXCA-2345H | PTA-2142 |
| DNA pXCA-2349H | PTA-2133 |
| DNA vegf4chim-6.1.2L | PTA-2134 |
| DNA vegf4chim-6.4.1L | PTA-2135 |
| DNA vegf4chim-2345L | PTA-2139 |
| DNA vegf4chim-2349L | PTA-2140 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC)

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention.

All references cited throughout the specification and the references cited therein are hereby expressly incorporated by reference.

What is claimed is:

1. A human anti-TrkC antibody selected from the group consisting of antibodies 6.1.2 (ATCC No. PTA-2148), 6.4.1 (ATCC No. PTA-2150), 2345 (ATCC No. PTA-2146), 2349 (ATCC No. PTA-2153), 2.5.1 (ATCC No. PTA-2151), and 2344 (ATCC No. PTA-2144).

2. The antibody of claim 1 selected from the group consisting of antibodies 6.1.2 (ATCC No. PTA-2148), 6.4.1 (ATCC No. PTA-2150), 2345 (ATCC No. PTA-2146), and 2349 (ATCC No. PTA-2153).

* * * * *